(12) United States Patent
Argenta et al.

(10) Patent No.: US 8,377,016 B2
(45) Date of Patent: Feb. 19, 2013

(54) APPARATUS AND METHOD FOR WOUND TREATMENT EMPLOYING PERIODIC SUB-ATMOSPHERIC PRESSURE

(75) Inventors: Louis O. Argenta, Winston-Salem, NC (US); Michael J. Morykwas, Winston-Salem, NC (US); Lawrence X. Webb, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 669 days.

(21) Appl. No.: 11/621,728

(22) Filed: Jan. 10, 2007

(65) Prior Publication Data

US 2008/0208147 A1  Aug. 28, 2008

(51) Int. Cl.
*A61F 13/00* (2006.01)
(52) U.S. Cl. ........ 604/305; 604/289; 604/290; 604/306; 604/307; 604/308; 604/313; 604/315; 604/316; 600/573; 600/575; 424/447; 424/448; 424/449
(58) Field of Classification Search .................. 604/305, 604/306, 307, 308
See application file for complete search history.

(56) References Cited

U.S. PATENT DOCUMENTS

| | | |
|---|---|---|
| 765,746 A | 7/1904 | Miner |
| 774,529 A | 11/1904 | Nieschang |
| 843,674 A | 2/1907 | Funk |
| 1,000,001 A | 8/1911 | Holz |
| 1,355,679 A | 10/1920 | McConnell |
| 1,355,846 A | 10/1920 | Rannells |
| 1,385,346 A | 7/1921 | Taylor |
| 1,936,129 A | 11/1933 | Fisk |
| 2,025,492 A | 11/1934 | Aird |
| 2,122,121 A | 6/1938 | Tillotson |
| 2,195,771 A | 4/1940 | Estler |
| 2,221,758 A | 11/1940 | Elmquist |
| 2,232,254 A | 2/1941 | Morgan |
| 2,280,915 A | 4/1942 | Johnson |

(Continued)

FOREIGN PATENT DOCUMENTS

| | | |
|---|---|---|
| AU | 2003231870 | 4/2009 |
| DE | 372727 | 3/1923 |

(Continued)

OTHER PUBLICATIONS

The American Heritage® Dictionary of the English Language, Fourth Edition, 2000.*

(Continued)

*Primary Examiner* — Tatyana Zalukaeva
*Assistant Examiner* — Ilya Treyger
(74) *Attorney, Agent, or Firm* — Niels Haun; Dann, Dorfman, Herrell & Skillman, P.C.

(57) ABSTRACT

A tissue treatment apparatus and method are provided for treating tissue by the application of the time-varying sub-atmospheric pressure. The apparatus includes a cover adapted to cover a wound and adapted to maintain sub-atmospheric pressure the site of the wound. The apparatus further includes a source of suction configured to generate a time-varying sub-atmospheric pressure having a periodic waveform comprising a gradual change in pressure. The suction source cooperates with the cover to supply the time-varying sub-atmospheric pressure under the cover to the wound. The time-varying sub-atmospheric pressure may vary between a first pressure value below the inherent tissue tension of the wound tissue and a second pressure value above the inherent tissue tension of the wound tissue.

118 Claims, 4 Drawing Sheets

U.S. PATENT DOCUMENTS

| | | |
|---|---|---|
| 2,338,339 A | 1/1944 | LaMere |
| 2,443,481 A | 6/1948 | Sene |
| 2,547,758 A | 4/1951 | Keeling |
| 2,573,791 A | 11/1951 | Howells |
| 2,577,945 A | 12/1951 | Atherton |
| 2,632,443 A | 3/1953 | Lesher |
| 2,682,873 A | 7/1954 | Evans |
| 2,910,763 A | 11/1959 | Lauterbach |
| 2,969,057 A | 1/1961 | Simmons |
| 3,026,526 A | 3/1962 | Montrose |
| 3,026,874 A | 3/1962 | Stevens |
| 3,042,041 A | 7/1962 | Jascalevich |
| 3,115,138 A | 12/1963 | McElvenny |
| 3,115,318 A | 12/1963 | Caillette |
| 3,315,665 A | 4/1967 | MacLeod |
| 3,324,855 A | 6/1967 | Heimlich |
| 3,367,332 A | 2/1968 | Groves |
| 3,382,867 A | 5/1968 | Reaves |
| 3,429,313 A | 2/1969 | Romanelli |
| 3,478,736 A | 11/1969 | Roberts et al. |
| 3,481,326 A | 12/1969 | Schamblin |
| 3,486,504 A | 12/1969 | Austin, Jr. |
| 3,520,300 A | 7/1970 | Flower et al. |
| 3,528,416 A | 9/1970 | Chamberlain |
| 3,568,675 A | 3/1971 | Harvey |
| 3,572,340 A | 3/1971 | Lloyd et al. |
| 3,610,238 A | 10/1971 | Rich, Jr. |
| 3,648,692 A | 3/1972 | Wheeler |
| 3,682,180 A | 8/1972 | McFarlane |
| 3,713,622 A | 1/1973 | Dinger |
| 3,753,439 A | 8/1973 | Brugarolas et al. |
| 3,782,377 A | 1/1974 | Rychlik |
| 3,782,387 A | 1/1974 | Falabella |
| 3,812,972 A | 5/1974 | Rosenblum |
| 3,814,095 A | 6/1974 | Lubens |
| 3,826,254 A | 7/1974 | Mellor |
| 3,874,387 A | 4/1975 | Barbieri |
| 3,896,810 A | 7/1975 | Akiyama |
| 3,903,882 A | 9/1975 | Augurt |
| 3,908,664 A | 9/1975 | Loseff |
| 3,935,863 A | 2/1976 | Kliger |
| 3,938,540 A | 2/1976 | Holbrook et al. |
| 3,954,105 A | 5/1976 | Nordby et al. |
| 3,976,060 A | 8/1976 | Hildebrandt |
| 3,978,855 A | 9/1976 | McRae et al. |
| 3,993,080 A | 11/1976 | Loseff |
| 3,998,227 A | 12/1976 | Holbrook et al. |
| RE29,319 E | 7/1977 | Nordby et al. |
| 4,080,970 A | 3/1978 | Miller |
| 4,112,947 A | 9/1978 | Nehring |
| 4,139,004 A | 2/1979 | Gonzalez, Jr. |
| 4,149,541 A | 4/1979 | Gammons et al. |
| 4,156,066 A | 5/1979 | Gould |
| 4,157,715 A | 6/1979 | Westerhoff |
| 4,169,563 A | 10/1979 | Leu |
| 4,172,455 A | 10/1979 | Beaussant |
| 4,184,510 A | 1/1980 | Murry et al. |
| 4,191,204 A | 3/1980 | Nehring |
| 4,221,215 A | 9/1980 | Mandelbaum |
| 4,224,941 A | 9/1980 | Stivala |
| 4,224,945 A | 9/1980 | Cohen |
| 4,250,882 A | 2/1981 | Adair |
| 4,256,109 A | 3/1981 | Nichols |
| 4,261,363 A | 4/1981 | Russo |
| 4,275,721 A | 6/1981 | Olson |
| 4,297,995 A | 11/1981 | Golub |
| 4,341,209 A | 7/1982 | Schaar |
| 4,373,519 A | 2/1983 | Errede et al. |
| 4,382,441 A | 5/1983 | Svedman |
| 4,392,853 A | 7/1983 | Muto |
| 4,399,816 A | 8/1983 | Spangler |
| 4,419,097 A | 12/1983 | Rowland |
| 4,452,845 A | 6/1984 | Lloyd et al. |
| 4,457,755 A | 7/1984 | Wilson |
| 4,459,139 A | 7/1984 | vonReis et al. |
| 4,465,062 A | 8/1984 | Versaggi et al. |
| 4,465,485 A | 8/1984 | Kashmer et al. |
| 4,469,092 A | 9/1984 | Marshall et al. |
| 4,475,909 A | 10/1984 | Eisenberg |
| 4,480,638 A | 11/1984 | Schmid |
| 4,499,896 A | 2/1985 | Heinecke |
| RE31,887 E | 5/1985 | Hodgson |
| 4,525,166 A | 6/1985 | Leclerc |
| 4,527,064 A | 7/1985 | Anderson |
| 4,533,352 A | 8/1985 | Van Beek |
| 4,540,412 A | 9/1985 | Van Overloop |
| 4,543,100 A | 9/1985 | Brodsky |
| 4,553,967 A | 11/1985 | Ferguson |
| 4,569,674 A | 2/1986 | Phillips et al. |
| 4,573,965 A | 3/1986 | Russo |
| 4,576,158 A | 3/1986 | Boland |
| 4,579,555 A | 4/1986 | Russo |
| 4,605,399 A | 8/1986 | Weston et al. |
| 4,608,041 A | 8/1986 | Nielsen |
| 4,615,338 A | 10/1986 | Ilizarov |
| 4,624,656 A | 11/1986 | Clark et al. |
| 4,627,427 A | 12/1986 | Arco |
| 4,633,863 A | 1/1987 | Filips |
| 4,637,819 A | 1/1987 | Ouellette |
| 4,640,688 A | 2/1987 | Hauser |
| 4,641,643 A | 2/1987 | Greer |
| 4,655,754 A | 4/1987 | Richmond et al. |
| 4,661,093 A | 4/1987 | Beck et al. |
| 4,664,652 A | 5/1987 | Weilbacher |
| 4,664,662 A | 5/1987 | Webster |
| 4,667,666 A | 5/1987 | Fryslie |
| 4,679,590 A | 7/1987 | Hergenroeder |
| 4,710,165 A | 12/1987 | McNeil et al. |
| 4,713,052 A | 12/1987 | Beck |
| 4,717,382 A | 1/1988 | Clemens et al. |
| 4,733,659 A | 3/1988 | Edenbaum |
| 4,743,232 A | 5/1988 | Kruger |
| 4,747,166 A | 5/1988 | Kuntz |
| 4,753,231 A | 6/1988 | Lang et al. |
| 4,753,232 A | 6/1988 | Ward |
| 4,759,354 A | 7/1988 | Quarfoot |
| 4,764,167 A | 8/1988 | Tu |
| 4,765,316 A | 8/1988 | Marshall |
| 4,773,409 A | 9/1988 | Cilento et al. |
| 4,778,446 A | 10/1988 | Jensen |
| 4,778,456 A | 10/1988 | Lokken |
| 4,820,265 A | 4/1989 | DeSatnick et al. |
| 4,820,284 A | 4/1989 | Hauri |
| 4,822,278 A | 4/1989 | Oliva |
| 4,834,110 A | 5/1989 | Richard |
| 4,836,192 A | 6/1989 | Abbate |
| 4,838,883 A | 6/1989 | Matsuura |
| 4,840,187 A | 6/1989 | Brazier |
| 4,841,962 A | 6/1989 | Berg et al. |
| 4,846,162 A | 7/1989 | Moehring |
| 4,851,545 A | 7/1989 | Song et al. |
| 4,860,737 A | 8/1989 | Lang et al. |
| 4,863,449 A | 9/1989 | Therriault |
| 4,872,450 A | 10/1989 | Austad |
| 4,875,473 A | 10/1989 | Alvarez |
| 4,877,019 A | 10/1989 | Vives |
| 4,878,901 A | 11/1989 | Sachse |
| 4,890,608 A | 1/1990 | Steer |
| 4,897,081 A | 1/1990 | Poirier |
| 4,906,233 A | 3/1990 | Moriuchi et al. |
| 4,906,240 A | 3/1990 | Reed |
| 4,917,112 A | 4/1990 | Kalt |
| 4,921,492 A | 5/1990 | Schultz et al. |
| 4,925,447 A | 5/1990 | Rosenblatt |
| 4,931,519 A | 6/1990 | Song et al. |
| 4,941,882 A | 7/1990 | Ward et al. |
| 4,953,565 A | 9/1990 | Tachibana et al. |
| 4,969,880 A | 11/1990 | Zamierowski |
| 4,969,881 A | 11/1990 | Viesturs |
| 4,973,331 A | 11/1990 | Pursley |
| 4,988,336 A | 1/1991 | Kohn |
| 4,990,144 A | 2/1991 | Blott |
| 4,991,574 A | 2/1991 | Pocknell |
| 4,997,425 A | 3/1991 | Shioya |
| 5,002,528 A | 3/1991 | Palestrant |
| 5,002,529 A | 3/1991 | Cunningham |
| 5,002,543 A | 3/1991 | Bradshaw |

| Patent | Date | Name |
|---|---|---|
| 5,003,971 A | 4/1991 | Buckley |
| 5,014,389 A | 5/1991 | Ogilvie |
| 5,019,086 A | 5/1991 | Neward |
| 5,034,003 A | 7/1991 | Denance |
| 5,034,006 A | 7/1991 | Hosoda |
| 5,034,012 A | 7/1991 | Frigg |
| 5,035,884 A | 7/1991 | Song et al. |
| 5,042,978 A | 8/1991 | Quenin |
| 5,060,662 A | 10/1991 | Farnsworth, III |
| 5,071,403 A | 12/1991 | Larason |
| 5,073,172 A | 12/1991 | Fell |
| 5,086,763 A | 2/1992 | Hathman |
| 5,086,764 A | 2/1992 | Gilman |
| 5,100,396 A | 3/1992 | Zamierowski |
| 5,100,404 A | 3/1992 | Hayes |
| 5,101,808 A | 4/1992 | Kobayashi |
| 5,102,413 A | 4/1992 | Poddar |
| 5,103,806 A | 4/1992 | McLeod |
| 5,106,362 A | 4/1992 | Gilman |
| 5,106,629 A | 4/1992 | Cartmell |
| 5,113,871 A | 5/1992 | Viljanto et al. |
| 5,135,518 A | 8/1992 | Vera |
| 5,147,338 A | 9/1992 | Lang |
| 5,149,331 A | 9/1992 | Ferdman et al. |
| 5,152,757 A | 10/1992 | Eriksson |
| 5,152,794 A | 10/1992 | Davidson |
| 5,160,322 A | 11/1992 | Scheremet |
| 5,167,613 A | 12/1992 | Karami |
| 5,170,781 A | 12/1992 | Loomis |
| 5,176,663 A | 1/1993 | Svedman |
| 5,176,667 A | 1/1993 | DeBring |
| 5,178,137 A | 1/1993 | Goor |
| 5,191,880 A | 3/1993 | McLeod |
| 5,192,282 A | 3/1993 | Draenert |
| 5,215,539 A | 6/1993 | Schoolman |
| 5,217,009 A | 6/1993 | Kronberg |
| 5,224,947 A | 7/1993 | Cooper |
| 5,228,431 A | 7/1993 | Giarretto |
| 5,230,350 A | 7/1993 | Fentress |
| 5,242,448 A | 9/1993 | Pettine |
| 5,261,893 A | 11/1993 | Zamierowski |
| 5,263,922 A | 11/1993 | Sova |
| 5,263,955 A | 11/1993 | Baumgart |
| 5,298,015 A | 3/1994 | Komatsuzaki |
| 5,330,452 A | 7/1994 | Zook |
| 5,344,415 A | 9/1994 | DeBusk |
| 5,349,965 A | 9/1994 | McCarver |
| 5,356,411 A | 10/1994 | Spievack |
| 5,358,494 A | 10/1994 | Svedman |
| 5,376,065 A | 12/1994 | McLeod |
| 5,376,252 A | 12/1994 | Ekstrom |
| 5,395,315 A | 3/1995 | Griep |
| 5,415,660 A | 5/1995 | Campbell |
| 5,419,768 A | 5/1995 | Kayser |
| 5,429,638 A | 7/1995 | Muschler |
| 5,431,662 A | 7/1995 | Nicholas |
| 5,437,651 A | 8/1995 | Todd |
| 5,445,604 A | 8/1995 | Lang |
| 5,447,492 A | 9/1995 | Cartmell |
| 5,451,215 A | 9/1995 | Wolter |
| 5,456,267 A | 10/1995 | Stark |
| 5,478,333 A | 12/1995 | Asherman, Jr. |
| 5,484,399 A | 1/1996 | DiResta et al. |
| 5,484,427 A | 1/1996 | Gibbons |
| 5,487,889 A | 1/1996 | Eckert |
| 5,496,262 A | 3/1996 | Johnson, Jr. |
| 5,520,652 A | 5/1996 | Peterson |
| 5,522,901 A | 6/1996 | Thomas et al. |
| 5,527,293 A | 6/1996 | Zamierowski |
| 5,531,670 A | 7/1996 | Westby |
| 5,542,918 A | 8/1996 | Atkinson |
| 5,549,584 A | 8/1996 | Gross |
| 5,556,375 A | 9/1996 | Ewall |
| 5,578,022 A | 11/1996 | Scherson |
| 5,580,353 A | 12/1996 | Mendes et al. |
| 5,588,955 A | 12/1996 | Johnson, Jr. |
| 5,607,388 A | 3/1997 | Ewall |
| 5,626,579 A | 5/1997 | Muschler |
| 5,628,735 A | 5/1997 | Skow |
| 5,636,643 A | 6/1997 | Argenta et al. |
| 5,645,081 A | 7/1997 | Argenta et al. |
| 5,655,258 A | 8/1997 | Heintz |
| 5,656,027 A | 8/1997 | Ellingboe |
| 5,662,598 A | 9/1997 | Tobin |
| 5,662,624 A | 9/1997 | Sundstrom |
| 5,662,625 A | 9/1997 | Westwood |
| 5,678,564 A | 10/1997 | Lawrence |
| 5,697,920 A | 12/1997 | Gibbons |
| 5,716,360 A | 2/1998 | Baldwin et al. |
| 5,717,005 A | 2/1998 | Richardson |
| 5,717,030 A | 2/1998 | Dunn |
| 5,720,720 A | 2/1998 | Laske |
| 5,733,884 A | 3/1998 | Barbul |
| 5,735,833 A | 4/1998 | Olson |
| 5,738,686 A | 4/1998 | Kubein-Meesenburg et al. |
| 5,743,912 A | 4/1998 | Lahille et al. |
| 5,759,205 A | 6/1998 | Valentini |
| 5,762,640 A | 6/1998 | Kajiwara |
| 5,782,871 A | 7/1998 | Fujiwara |
| 5,807,230 A | 9/1998 | Argenta et al. |
| 5,810,840 A | 9/1998 | Lindsay |
| 5,817,145 A | 10/1998 | Augustine |
| 5,827,246 A | 10/1998 | Bowen |
| 5,876,359 A | 3/1999 | Bock et al. |
| 5,911,222 A | 6/1999 | Lawrence |
| 5,919,476 A | 7/1999 | Fischer |
| 5,921,972 A | 7/1999 | Skow |
| 5,928,174 A | 7/1999 | Gibbins |
| 5,935,136 A | 8/1999 | Hulse et al. |
| 5,941,859 A | 8/1999 | Lerman |
| 5,947,914 A | 9/1999 | Augustine |
| 5,951,295 A | 9/1999 | Lyles et al. |
| 5,954,680 A | 9/1999 | Augustine |
| 5,958,314 A | 9/1999 | Draenert |
| 5,961,480 A | 10/1999 | Augustine |
| 5,964,721 A | 10/1999 | Augustine |
| 5,964,723 A | 10/1999 | Augustine |
| 5,964,733 A | 10/1999 | Laabs et al. |
| 5,968,047 A | 10/1999 | Reed |
| 5,986,163 A | 11/1999 | Augustine |
| 6,010,527 A | 1/2000 | Augustine |
| 6,045,518 A | 4/2000 | Augustine |
| 6,045,541 A | 4/2000 | Matsumoto |
| 6,051,016 A | 4/2000 | Mesaros et al. |
| 6,053,416 A | 4/2000 | Specht |
| 6,071,254 A | 6/2000 | Augustine |
| 6,071,267 A | 6/2000 | Zamierowski |
| 6,071,304 A | 6/2000 | Augustine |
| 6,080,189 A | 6/2000 | Augustine |
| 6,080,243 A | 6/2000 | Insley |
| 6,086,587 A | 7/2000 | Hawk |
| 6,087,553 A | 7/2000 | Cohen et al. |
| 6,093,160 A | 7/2000 | Augustine |
| 6,095,148 A | 8/2000 | Shastri |
| 6,095,992 A | 8/2000 | Augustine |
| 6,110,197 A | 8/2000 | Augustine |
| 6,113,561 A | 9/2000 | Augustine |
| 6,117,111 A | 9/2000 | Fleischmann |
| 6,135,116 A | 10/2000 | Vogel |
| 6,142,982 A | 11/2000 | Hunt |
| 6,143,035 A | 11/2000 | McDowell |
| 6,143,945 A | 11/2000 | Augustine |
| 6,146,423 A | 11/2000 | Cohen et al. |
| 6,159,246 A | 12/2000 | Mendes et al. |
| 6,174,306 B1 | 1/2001 | Fleischmann |
| 6,187,047 B1 | 2/2001 | Kwan et al. |
| 6,190,391 B1 | 2/2001 | Stubbs |
| 6,203,563 B1 | 3/2001 | Fernandez |
| 6,207,875 B1 | 3/2001 | Lindqvist |
| 6,213,965 B1 | 4/2001 | Augustine |
| 6,213,966 B1 | 4/2001 | Augustine |
| 6,217,535 B1 | 4/2001 | Augustine |
| 6,235,009 B1 | 5/2001 | Skow |
| 6,235,047 B1 | 5/2001 | Augustine |
| 6,241,697 B1 | 6/2001 | Augustine |
| 6,241,698 B1 | 6/2001 | Augustine |
| 6,248,084 B1 | 6/2001 | Augustine |
| 6,254,557 B1 | 7/2001 | Augustine |

| | | |
|---|---|---|
| 6,254,580 B1 | 7/2001 | Svedman |
| 6,264,622 B1 | 7/2001 | Augustine |
| 6,264,979 B1 | 7/2001 | Svedman |
| 6,267,740 B1 | 7/2001 | Augustine |
| 6,283,931 B1 | 9/2001 | Augustine |
| 6,284,941 B1 | 9/2001 | Cox |
| 6,290,685 B1 | 9/2001 | Insley |
| 6,293,917 B1 | 9/2001 | Augustine |
| 6,323,146 B1 | 11/2001 | Pugh |
| 6,325,788 B1 * | 12/2001 | McKay ............ 604/506 |
| 6,344,061 B1 | 2/2002 | Leitao et al. |
| 6,345,623 B1 | 2/2002 | Heaton et al. |
| 6,355,215 B1 | 3/2002 | Poggie et al. |
| 6,359,189 B1 | 3/2002 | Fleischmann |
| 6,377,653 B1 | 4/2002 | Lee et al. |
| 6,394,948 B1 | 5/2002 | Borst et al. |
| 6,398,767 B1 | 6/2002 | Fleischmann |
| 6,430,427 B1 | 8/2002 | Lee et al. |
| 6,458,109 B1 | 10/2002 | Henley |
| 6,484,716 B1 | 11/2002 | Leininger |
| 6,485,503 B2 * | 11/2002 | Jacobs et al. ............ 606/215 |
| 6,488,643 B1 | 12/2002 | Tumey |
| 6,491,693 B1 | 12/2002 | Lytinas |
| 6,520,982 B1 | 2/2003 | Boynton |
| 6,551,317 B2 | 4/2003 | Berish et al. |
| 6,553,998 B2 | 4/2003 | Heaton et al. |
| 6,555,729 B1 | 4/2003 | Fleischmann |
| 6,557,487 B1 | 5/2003 | Fleischmann |
| 6,641,604 B1 | 11/2003 | Adelman |
| 6,648,862 B2 | 11/2003 | Watson |
| 6,663,349 B1 | 12/2003 | Discenzo |
| 6,673,028 B1 | 1/2004 | Argenta et al. |
| 6,682,491 B2 | 1/2004 | Johnson |
| 6,685,681 B2 | 2/2004 | Lockwood |
| 6,695,823 B1 | 2/2004 | Lina |
| 6,712,851 B1 | 3/2004 | Lemperle et al. |
| 6,749,592 B2 | 6/2004 | Lord |
| 6,752,794 B2 | 6/2004 | Lockwood |
| 6,755,807 B2 | 6/2004 | Risk, Jr. |
| 6,764,462 B2 | 7/2004 | Risk, Jr. |
| 6,767,334 B1 | 7/2004 | Randolph |
| 6,770,794 B2 | 8/2004 | Fleischmann |
| 6,793,633 B2 * | 9/2004 | Douglas et al. ............ 600/583 |
| 6,800,074 B2 | 10/2004 | Henley |
| 6,814,079 B2 | 11/2004 | Heaton et al. |
| 6,824,533 B2 | 11/2004 | Risk, Jr. |
| 6,840,960 B2 | 1/2005 | Bubb |
| 6,855,135 B2 | 2/2005 | Lockwood |
| 6,856,821 B2 | 2/2005 | Johnson |
| 6,863,022 B2 | 3/2005 | Fleischmann |
| 6,878,119 B2 | 4/2005 | Johnson |
| 6,887,246 B2 | 5/2005 | Bhatnagar et al. |
| 6,936,037 B2 | 8/2005 | Bubb |
| 6,951,553 B2 | 10/2005 | Bubb |
| 6,988,423 B2 | 1/2006 | Bolam |
| 6,994,702 B1 | 2/2006 | Johnson |
| 7,004,915 B2 | 2/2006 | Boynton |
| 7,022,113 B2 | 4/2006 | Lockwood |
| 7,066,960 B1 | 6/2006 | Dickman |
| 7,070,584 B2 | 7/2006 | Johnson |
| 7,077,832 B2 | 7/2006 | Fleischmann |
| 7,108,683 B2 | 9/2006 | Zamierowski |
| 7,117,869 B2 | 10/2006 | Heaton |
| 7,128,735 B2 * | 10/2006 | Weston ............ 604/543 |
| 7,144,390 B1 | 12/2006 | Hannigan |
| 7,169,151 B1 | 1/2007 | Lytinas |
| 7,175,625 B2 | 2/2007 | Culbert |
| 7,198,046 B1 | 4/2007 | Argenta |
| 7,216,651 B2 | 5/2007 | Argenta |
| 7,276,051 B1 | 10/2007 | Henley et al. |
| 7,279,612 B1 | 10/2007 | Heaton et al. |
| 7,520,872 B2 | 4/2009 | Biggie |
| 7,753,894 B2 | 7/2010 | Blott |
| 7,931,651 B2 | 4/2011 | Webb et al. |
| 2001/0029956 A1 | 10/2001 | Argenta et al. |
| 2001/0043943 A1 | 11/2001 | Coffey |
| 2002/0065494 A1 | 5/2002 | Lockwood et al. |
| 2002/0082567 A1 | 6/2002 | Lockwood et al. |
| 2002/0115952 A1 | 8/2002 | Johnson et al. |
| 2002/0120185 A1 | 8/2002 | Johnson |
| 2002/0143286 A1 | 10/2002 | Tumey |
| 2002/0143344 A1 | 10/2002 | Taylor |
| 2002/0143403 A1 | 10/2002 | Vaidyanathan et al. |
| 2002/0161317 A1 | 10/2002 | Risk et al. |
| 2002/0161346 A1 | 10/2002 | Lockwood et al. |
| 2002/0198503 A1 | 12/2002 | Risk, Jr. et al. |
| 2002/0198504 A1 | 12/2002 | Risk, Jr. et al. |
| 2003/0040687 A1 | 2/2003 | Boynton |
| 2003/0050594 A1 | 3/2003 | Zamierowski |
| 2003/0108587 A1 | 6/2003 | Orgill et al. |
| 2003/0130599 A1 | 7/2003 | Restle et al. |
| 2003/0187367 A1 | 10/2003 | Odland |
| 2003/0208149 A1 | 11/2003 | Coffey |
| 2003/0219469 A1 | 11/2003 | Johnson |
| 2003/0225347 A1 | 12/2003 | Argenta |
| 2003/0225441 A1 | 12/2003 | Boynton |
| 2004/0006319 A1 | 1/2004 | Lina |
| 2004/0024351 A1 | 2/2004 | Greter |
| 2004/0030304 A1 | 2/2004 | Hunt |
| 2004/0039391 A1 | 2/2004 | Argenta |
| 2004/0039415 A1 | 2/2004 | Zamierowski |
| 2004/0064111 A1 | 4/2004 | Lockwood et al. |
| 2004/0064132 A1 | 4/2004 | Boehringer |
| 2004/0073151 A1 | 4/2004 | Weston |
| 2004/0122434 A1 | 6/2004 | Argenta |
| 2004/0127845 A1 * | 7/2004 | Renz et al. ............ 604/74 |
| 2004/0167482 A1 | 8/2004 | Watson |
| 2004/0225178 A1 | 11/2004 | Kriewall |
| 2004/0225208 A1 | 11/2004 | Johnson |
| 2004/0249353 A1 | 12/2004 | Risks, Jr. et al. |
| 2004/0260230 A1 | 12/2004 | Randolph |
| 2004/0267265 A1 | 12/2004 | Kyle |
| 2005/0020955 A1 | 1/2005 | Sanders |
| 2005/0028828 A1 | 2/2005 | Heaton et al. |
| 2005/0043659 A1 | 2/2005 | Challis et al. |
| 2005/0065484 A1 | 3/2005 | Watson, Jr. |
| 2005/0090787 A1 | 4/2005 | Risk, Jr. et al. |
| 2005/0101940 A1 | 5/2005 | Radl |
| 2005/0124966 A1 | 6/2005 | Karpowicz |
| 2005/0131327 A1 | 6/2005 | Lockwood et al. |
| 2005/0148913 A1 | 7/2005 | Weston |
| 2005/0165350 A1 | 7/2005 | Greter |
| 2005/0177190 A1 | 8/2005 | Zamierowski |
| 2005/0182445 A1 | 8/2005 | Zamierowski |
| 2005/0197645 A1 | 9/2005 | Karpowicz |
| 2005/0203452 A1 | 9/2005 | Weston |
| 2005/0209574 A1 | 9/2005 | Boehringer |
| 2005/0222527 A1 | 10/2005 | Miller |
| 2005/0222528 A1 | 10/2005 | Weston |
| 2005/0222544 A1 | 10/2005 | Weston |
| 2005/0228329 A1 | 10/2005 | Boehringer |
| 2005/0234510 A1 | 10/2005 | Zamierowski |
| 2005/0240220 A1 | 10/2005 | Zamierowski |
| 2005/0261615 A1 | 11/2005 | Weston |
| 2005/0261642 A1 | 11/2005 | Weston |
| 2005/0283105 A1 | 12/2005 | Heaton et al. |
| 2006/0025727 A1 | 2/2006 | Boehringer |
| 2006/0029650 A1 | 2/2006 | Coffey |
| 2006/0029675 A1 | 2/2006 | Ginther |
| 2006/0079852 A1 | 4/2006 | Bubb |
| 2006/0100586 A1 | 5/2006 | Karpowicz |
| 2006/0149170 A1 | 7/2006 | Boynton |
| 2006/0149171 A1 | 7/2006 | Vogel |
| 2006/0149176 A1 | 7/2006 | Bolam |
| 2006/0173253 A1 | 8/2006 | Ganapathy |
| 2006/0189910 A1 | 8/2006 | Johnson |
| 2006/0213527 A1 | 9/2006 | Argenta et al. |
| 2006/0286076 A1 | 12/2006 | Fleischmann |
| 2007/0005028 A1 | 1/2007 | Risk, Jr. et al. |
| 2007/0014837 A1 | 1/2007 | Johnson |
| 2007/0021697 A1 | 1/2007 | Ginther |
| 2007/0021698 A1 | 1/2007 | Fleischmann |
| 2007/0032754 A1 | 2/2007 | Walsh |
| 2007/0071790 A1 | 3/2007 | Ameer et al. |
| 2007/0219585 A1 | 9/2007 | Cornet et al. |
| 2007/0233022 A1 | 10/2007 | Henley et al. |
| 2007/0260226 A1 | 11/2007 | Jaeb et al. |

| | | | |
|---|---|---|---|
| 2009/0187259 A1 | 7/2009 | Argenta et al. | |
| 2009/0254120 A1 | 10/2009 | Argenta et al. | |
| 2010/0121229 A1 | 5/2010 | Argenta et al. | |

FOREIGN PATENT DOCUMENTS

| | | |
|---|---|---|
| DE | 561757 | 10/1932 |
| DE | 847475 | 6/1952 |
| DE | 847475 | 8/1952 |
| DE | 1963258 | 6/1971 |
| DE | 2809828 | 9/1978 |
| DE | 3102674 | 9/1982 |
| DE | 3539533 | 5/1987 |
| DE | 4111122 | 4/1993 |
| DE | 29504378 | 9/1995 |
| DE | 19722075 | 10/1998 |
| DK | 64055 | 10/1945 |
| EP | 0117632 | 9/1984 |
| EP | 0424165 | 4/1991 |
| EP | 0485657 | 5/1992 |
| EP | 0547496 | 6/1993 |
| EP | 0620720 | 10/1994 |
| EP | 0620720 B2 | 10/1994 |
| EP | 0688189 | 12/1995 |
| EP | 0777504 | 6/1997 |
| EP | 0821929 | 2/1998 |
| EP | 0853950 | 7/1998 |
| EP | 0880953 | 12/1998 |
| EP | 1023872 A2 | 8/2000 |
| EP | 0688189 | 9/2000 |
| EP | 1064958 | 1/2001 |
| EP | 1088569 | 4/2001 |
| EP | 1023872 A3 | 8/2002 |
| EP | 1452191 | 9/2004 |
| EP | 0688189 B2 | 6/2005 |
| FR | 500253 | 3/1920 |
| FR | 1303238 | 9/1962 |
| GB | 190203090 | 6/1902 |
| GB | 114754 | 4/1918 |
| GB | 641061 | 8/1950 |
| GB | 1273342 | 5/1972 |
| GB | 1457164 | 12/1976 |
| GB | 1549756 | 8/1979 |
| GB | 2 195 255 | 4/1988 |
| GB | 2195255 | 4/1988 |
| GB | 2329127 | 3/1999 |
| GB | 2333965 | 8/1999 |
| GB | 2336546 | 10/1999 |
| GB | 2342584 | 4/2000 |
| GB | 2344531 | 6/2000 |
| GB | 2351025 | 12/2000 |
| JP | 2000237219 | 9/2000 |
| SE | 84485 | 10/1935 |
| SU | 587941 | 1/1978 |
| SU | 1416108 | 7/1985 |
| SU | 1251912 | 8/1986 |
| SU | 1268175 | 11/1986 |
| WO | 80/01139 | 6/1980 |
| WO | 87/00439 | 1/1987 |
| WO | 87/04626 | 8/1987 |
| WO | WO 87/04626 | 8/1987 |
| WO | WO 89/04158 | 5/1989 |
| WO | 90/10424 | 9/1990 |
| WO | WO 90/10424 | 9/1990 |
| WO | 9011795 | 10/1990 |
| WO | 9100718 | 1/1991 |
| WO | 9116030 | 10/1991 |
| WO | 9219313 | 11/1992 |
| WO | 9220299 | 11/1992 |
| WO | 93/09725 | 5/1993 |
| WO | 94/00090 | 1/1994 |
| WO | 94/20041 | 9/1994 |
| WO | WO 94/20041 | 9/1994 |
| WO | 96/05873 | 2/1996 |
| WO | 96/15745 | 5/1996 |
| WO | 99/13793 | 3/1999 |
| WO | 99/51164 | 10/1999 |
| WO | 00/07653 | 2/2000 |
| WO | 00/15277 | 3/2000 |
| WO | 00/21586 | 4/2000 |
| WO | 00/26100 | 5/2000 |
| WO | 00/30567 | 6/2000 |
| WO | 00/32247 | 6/2000 |
| WO | 00/38552 | 7/2000 |
| WO | 00/38755 | 7/2000 |
| WO | 00/42958 | 7/2000 |
| WO | 00/59418 | 10/2000 |
| WO | 00/59424 | 10/2000 |
| WO | 00/61206 | 10/2000 |
| WO | 00/64394 | 11/2000 |
| WO | 01/34223 | 5/2001 |
| WO | 01/37922 | 5/2001 |
| WO | 01/49233 | 7/2001 |
| WO | 01/85248 | 11/2001 |
| WO | WO 01/89431 | 11/2001 |
| WO | WO 02/43634 | 6/2002 |
| WO | 03/005943 | 1/2003 |
| WO | 03/101385 | 12/2003 |
| WO | WO 03/101508 | 12/2003 |
| WO | 2005/102234 | 11/2005 |
| WO | 2006114637 | 11/2006 |
| WO | 2008063281 | 5/2008 |
| WO | 2009/049058 | 4/2009 |
| WO | 2009/089435 | 7/2009 |
| WO | 2010009294 | 1/2010 |

OTHER PUBLICATIONS

*Innovative Therapies, Inc.*, v. *Kinetic Concepts, Inc., et al.*, Case No. 07-cv-00589 in the United States District Court for the District of Delaware, Complaint filed with jury demand, cover sheet and acknowledgement of consent form, filed by ITI on Sep. 25, 2007. DED-001.

*ITI* v. *KCI*, Case No. 07-589, Motion to dismiss for lack of jurisdiction over the subject matter, proposed order, opening brief in support of motion, and declarations, filed by KCI on Oct. 15, 2007. DED-002.

*ITI* v. *KCI*, Case No. 07-589, Plaintiff's answering brief in opposition to defendants' motion to dismiss, with exhibits, filed by ITI on Nov. 14, 2007. DED-004.

*Kinetic Concepts, Inc., et al.* v. *Medela AG et al.*, Case No. 2:07cv187 in the United States District Court Eastern District of Texas Marshall Division, Complaint with request for jury trial with cover sheet, filed by KCI on May 15, 2007. MDIV187-001.

*KCI* v. *Medela*, Case No. 2:07cv187, Answer to complaint and counterclaim, filed by Medela Inc. on Jul. 10, 2007. MDIV187-002.

*KCI* v. *Medela*, Case No. 2:07cv187, Motion to change venue, with proposed order and exhibits, filed by Medela, Inc. on Jul. 10, 2007. MDIV187-003.

*KCI* v. *Medela*, Case No. 2:07cv187, Motion to dismiss for lack of personal jurisdiction, with proposed order and exhibits A-C, filed by Medela AG on Jul. 11, 2007. MDIV187-004.

*KCI*v. *Medela*, Case No. 2:07cv187, Response to motion to change venue, with proposed order and exhibits, filed by KCI on Aug. 1, 2007. MDIV187-005.

*KCI* v. *Medela*, Case No. 2:07cv187, Answer to Counterclaim, filed by KCI on Aug. 2, 2007. MDIV187-006.

*KCI* v. *Medela*, Case No. 2:07cv187, Response in opposition to motion to dismiss for lack of personal jurisdiction, with proposed order, index, and exhibits, filed by KCI on Aug. 2, 2007. MDIV187-007.

*KCI* v. *Medela*, Case No. 2:07cv187, Reply to response to motion to change venue, with exhibit, filed by Medela, Inc. on Aug. 13, 2007. MDIV187-008.

*KCI* v. *Medela*, Case No. 2:07cv187, Reply to motion to dismiss for lack of personal jurisdiction, with exhibits, filed by Medela AG on Aug. 13, 2007. MDIV187-009.

*KCI* v. *Medela*, Case No. 2:07cv187, Surreply to reply to response to motion to change venue, filed by KCI on Aug. 23, 2007. MDIV187-010.

*KCI* v. *Medela*, Case No. 2:07cv187, Surreply to reply to response to motion to dismiss for lack of personal jurisdiction, with exhibits, filed by KCI on Aug. 23, 2007. MDIV187-011.

*Kinetic Concepts, Inc., et al. v. Blue Sky Medical Corporation, et al.*, Case No. 2:07cv188 in the United States District Court Eastern District of Texas Marshall Division, Complaint with request for jury trial, with cover sheet, filed by KCI on May 15, 2007. MDIV188-001.
*KCI v. Blue Sky*, Case No. 2:07cv188, Amended Complaint with request for jury trial and Request for Declaratory Judgment, with exhibit A, filed by KCI on May 15, 2007. MDIV188-002.
*KCI v. Blue Sky*, Case No. 2:07cv188, Answer to Amended Complaint, with Counterclaim, filed by Blue Sky on Jul. 10, 2007. MDIV188-003.
*KCI v. Blue Sky*, Case No. 2:07cv188, Motion to dismiss for lack of jurisdiction, with proposed order, corrected proposed order and exhibits A-E, filed by Smith & Nephew Holdings, Inc, Smith & Nephew, PLC on Jul. 13, 2007. MDIV188-004.
*KCI v. Blue Sky*, Case No. 2:07cv188, Motion to change venue, with proposed order, corrected proposed order and exhibits 1, 4-9, 11, 12, filed by Blue Sky on Jul. 23, 2007. MDIV188-005.
*KCI v. Blue Sky*, Case No. 2:07cv188, Answer to counterclaim filed by KCI on Aug. 2, 2007. MDIV188-006.
*KCI v. Blue Sky*, Case No. 2:07cv188, Response in opposition to motion to dismiss for lack of jurisdiction, with proposed order and exhibits 1-7, filed by KCI on Aug. 6, 2007. MDIV188-007.
*KCI v. Blue Sky*, Case No. 2:07cv188, Response in opposition to motion to change venue, filed by KCI on Aug. 7, 2007. MDIV188-008.
*KCI v. Blue Sky*, Case No. 2:07cv188, Reply in support of motion to dismiss for lack of perosnal jurisdiction, filed by Smith & Nephew Holdings, Inc., Smith & Nephew, PLC on Aug. 16, 2007. MDIV188-009.
*KCI v. Blue Sky*, Case No. 2:07cv188, Response to motion to change venue, with exhibits 13-15, filed by Blue Sky on Aug. 16, 2007. MDIV188-010.
*KCI v. Blue Sky*, Case No. 2:07cv188, Surreply to reply to response to motion to dismiss for lack of jurisdiction, filed by KCI on Aug. 28, 2007. MDIV188-011.
*KCI v. Blue Sky*, Case No. 2:07cv188, Surreply to reply to response to motion to change venue, filed by KCI on Aug. 28, 2007. MDIV188-012.
*Medela, Inc. v. Kinetic Concepts, Inc., et al.*, Case No. 7cv449 in the United States District Court Western District of Texas San Antonio Division, Complaint for Declaratory Judgment, filed by Medela Inc. on May 22, 2007. SA449-001.
*Medela v. KCI*, Case No. 7cv449, Opposed motion to dismiss, or in the alternative, motion to transfer case, with exhibits 2-4 and proposed order, filed by KCI on Jul. 13, 2007. SA449-002.
*Medela v. KCI*, Case No. 7cv449, Answer to Complaint for Declaratory Judgment, filed by KCI on Jul. 13, 2007. SA449-003.
*Medela v. KCI*, Case No. 7cv449, Response to motion to dismiss, with Declaration and Exhibits B-G, filed by Medela, Inc. on Aug. 3, 2007. SA449-004.
*Medela v. KCI*, Case No. 7cv449, Reply to response to motion to transfer, filed by KCI on Aug. 17, 2007. SA449-005.
*Medela v. KCI*, Case No. 7cv449, Order staying defendants' motion entered Oct. 11, 2007. SA449-006.
*Blue Sky Medical Group, Inc., et al. v. Kinetic Concepts, Inc. et al.*, Case No. 7cv454 in the United States District Court Western District of Texas San Antonio Division, Complaint for Declaratory Judgment and cover sheet, filed by Blue Sky on May 23, 2007. SA454-001.
*Blue Sky v. KCI*, Case No. 7cv454, First Amended and Supplemental Complaint for Declaratory Judgment, filed by Blue Sky on Jul. 12, 2007. SA454-002.
*Blue Sky v. KCI*, Case No. 7cv454, Motion to dismiss, or in the alternative, motion to transfer case, with proposed order and exhibits 2-4, filed by KCI on Aug. 1, 2007. SA454-003.
*Blue Sky v. KCI*, Case No. 7cv454, Answer to first amended complaint with jury demand, filed by KCI on Aug. 1, 2007. SA454-004.
*Blue Sky v. KCI*, Case No. 7cv454, Response in opposition to motion to dismiss, or in the alternative motion to transfer case, with exhibits A-G and proposed order, filed by Blue Sky on Aug. 16, 2007. SA454-005.
*Blue Sky v. KCI*, Case No. 7cv454, Reply to response to motion, filed by KCI on Aug. 30, 2007. SA454-006.

*Blue Sky v. Kci*, Case No. 7cv454, Order staying defendant's motion pending the outcome of Blue Sky's motion regarding opposed motion to dismiss or in the alternative, motion to transfer case, entered Oct. 11, 2007. SA454-007.
M. Gosta Arturson, The Pathophysiology of Severe Thermal Injury, *JBCR*, 6(2):129-146 Mar.-Apr. 1985. NPL-020.
R. A.F. Clark et al., The Molecular and Cellular Biology of Wound Repair, Chapter 1 (1988) NPL-085.
Jeter, K.F. et al. (eds.), "Managing Draining Wounds and Fistulae: New and Established Methods," Chronic Wound Care: Health Management Publications, 1990, pp. 240-246. NPL-223.
Aeros, "Moblvac II." NPL-004.
Aeros, Aeros Instruments, Inc. 1111 Lakeside Drive, Gurnee, IL 60031. Aug. 1993. "Care-E-Vac." NPL-005.
Emerson, Series 55. J. H. Emerson Co., 22 Cottage Park Ave., Cambridge, MA 02140. "Emerson Post-Operative Suction Pumps." NPL-139.
Emerson, J. H. Emerson Co., (address: same as above). "Emerson Transport Suction Unit." NPL-138.
Aeros, Aeros Instruments, Inc. 3411 Commercial Ave., Northbrook, IL 60062. Oct. 1988. Part No. 1504-02 7M. "Instavac Aspirator." NPL-006.
"Pleur-evac. Adult-Pediatric, Non-Metered." Code No. A-4000. Control Number: F7961J. NPL-333.
Instruction Manual, Creative Medical Laboratories, Inc. P.O. Box 6347, Rochester, Minn. 55903. "TUGS" (Transportable Universal Gradient Suction). NPL-221.
Deknatel, Div. of Howmedica, Inc. Quenns Village, NY 11429. "Pleur-evac." NPL-111.
Sparta Instrument Corp. 26602 Corporate Ave., Hayward, CA 94545. "Power Source Multi-Purpose Surgical Aspirator." NPL-383.
Wells Johnson Company, 2045 N. Forbes Blvd., Suite 106, Tucson, AZ. "Point 5 Aspirator." NPL-433.
Microtek Heritage, Inc. P.O. Box 2487, Columbus, MS 39704. "Wound-Evac ET." NPL-284.
Fleischmann, W. *Wund Forum Spezial*. IHW '94. "Vakuumversiegelung zur Behandlung von Probelmwunden" (with English translation: "Vacuum sealing for Treatment of Problematical Wounds." NPL-160.
Fleischmann, W. *Acta Orthopaedica Belgica*. vol. 58, Suppl. I-1992 "Treatment of Bone and Soft Tissue Defects in Infected Nonunion." NPL-159.
Fleischmann, W. Strecker W, Bombelli M, Kinzl L. *Unfall Chirurg*. Springer-Variag 1993. 96:488-92 "Vakuumversiegelung zur Behandlung des Weichteilschadens bei offenen Frakturen." with English translation [Vacuum sealing as treatment of soft tissue damage in open fractures]. [German] NPL-157.
Valenta, A.L. *American Journal of Nursing*. Apr. 1994. "Using the Vacuum Dressing Alternative for Difficult Wounds." 94:44-5 NPL-414.
Bier, A., "Hyperemia by Suction Apparatus" Chapter VIII, Hyperemia as a Therapeutic Agent, Chicago, IL, Roberts Publishing, 74-85, (1905). NPL-216.
Saunders, J. W., The Lancet, pp. 1286-1287, Jun. 28, 1952, "Negative-Pressure Device for Controlled Hypotension during Surgical Operations" NPL-356.
Landis, et al., Robinette Foundation of the Hospital of the University of Pennsylvania, "The Effects of Alternate Suction and Pressure on Blood Flow to the Lower Extremities" (Sep. 1933). NPL-249.
Hargens et al., Space Physiology Laboratory, Life Science Division, NASA Ames Research Center, "Control of Circulatory Function in Altered Gravitational Fields" (Feb. 1992). NPL-189.
Wolthuis et al, Physiological Reviews, 54: 566-595, Jul. 1974, "Physiological Effects of Locally Applied Reduced Pressure in Man" NPL-441.
Viljanto et al., Br. J. Surg., 63: 427-430, 1976, "Local Hyperalimentation of Open Wounds" NPL-419.
Dillon, R. Angiology—The Journal of Vascular Diseases, pp. 47-56, Jan. 1986, "Treatment of Resistant Venous Stasis Ulcers and Dermatitis with the End-Diastolic Pneumatic Compression Boot" NPL-118.

Lundvall et al., Acta Physiol Scand, 136: 403-409, accepted Jan. 28, 1989, "Transmission of externally applied negative pressure to the underlying tissue. A study on the upper arm of man" NPL-262.

Klemp et al., The Journal of Investigative Dermatology, pp. 725-726 (1989), "Subcutaneous Blood Flow in Early Male Pattern Baldness" NPL-236.

A. Harle, Z. Orthop., 127: 513-517 (1989), "Schwachstellen herkommlicher Drainagen"with English Translation. NPL-192.

Dunlop et al., Br. J. Surg., 77: 562-563 (1990), "Vacuum drainage of groin wounds after vascular surgery: a controlled trail". NPL-125.

Maddin et al., International Journal of Dermatology, 29: 446-450 (1990), "The Biological Effects of a Pulsed Electrostatic Field with Specific Reference to Hair: Electrotrichogenesis" NPL-263.

Nakayama et al., Ann. Plast. Surg., 26:499-502 (1991), "A New Dressing Method for Free Skin Grafting in Hands" NPL-307.

Hargens et al., Aviation, Space and Environmental Medicine, pp. 934-937, Oct. 1991, "Lower Body Negative Pressure to Provide Load Bearing in Space" NPL-188.

Author unknown, Science, Sep. 1992, p. 42, "The Not-So-Bald-Truth" NPL-022.

Techno Takatsuki Co., Ltd., 8-16 Hatchonishimachi, Takatsuki City, Osaka, Japan, "HiBlow Air Pump" NPL-399.

Wells Johnson Company, 2045 N. Forbe Blvd., Suite 106, Tucson, AZ, "Suction Tips" NPL-432.

Industrial Equipment News, P.O. Box 1158, Skokie, IL 60076-9786, "Miscellaneous Equipment" NPL-218.

Letsou et al. "Stimulation of Adenylate Cyclase Activity in Cultured Endothelial Cells Subjected to Cyclic Stretch." Cardiovascular Surgery 3. Toronto. Sep. 1989. 634-639. NPL-253.

Bucalo et al. "Inhibition of Cell Proliferation by Chronic wound Fluid." Wound Repair and Regeneration. 181-186 Jul. 1993 NPL-065.

Falanga, Vincent. "Growth Factors and Chronic Wounds: The need to Understand the Microenvironment." Journal of Dermatology, Bol. 19: 667-672. 1992. NPL-148.

Urschel et al. "The Effect of Mechanical Stress on Soft and Hard Tissue Repair; a Review." British Journal of Plastic Surgery. 41, 182-186. 1988. NPL-411.

Gogia, Prem P. "The Biology of Wound Healing." Ostomy/Wound Management. Nov.-Dec. 1992. pp. 12, 14-16, 18-20, 22 NPL-172.

Wysocki et al. "Wound Fluid from Chronic Leg Ulcers Contains Elevated Levels of Metalloproteinases MMP-2 and MMP-9." The Society for Investigative Dermatology, Inc. Jul. 1993. 64-68 NPL-450.

Olenius et al. "Mitotic Activity in Expanded Human Skin." Plastic and Reconstructive Surgery. Feb. 1993. 213-216. NPL-318.

Mulder, G. D. et al. (eds.), *Clinicians' Pocket Guide to Chronic Wound Repair*, (Spartanburg, SC: Wound Healing Publications), 1991, pp. 54-55. NPL-317.

Chariker, M. E. et al. (eds), "Effective Management of Incisional and Cutaneous Fistulae with Closed Suction Wound Drainage," Contemporary Surgery, vol. 34, Jun. 1989, pp. 59-63. NPL-073.

Rastgeldi, S.: I. Pressure Treatment of Peripheral Vascular Diseases. II. Intermittent Pressure Treatment of Peripheral Vascular Diseases. Opuscula Medica, Suppl. XXVII, 1972. NPL-343.

OP-Journal Nr. 3, Jahr. 6, Dec. 1990, pp. 31-35 W. Fleischmann, M. Mentzel, L. Kinzl "BWS, Gefahren and Komplikationen der Therapie" with English Trans. NPL-156.

Zumtobel et al., (1991) "Wunddrainage in der Elektiveund Notfallchirurgie" Wolfgang Pabst Verlag, relevant p. 12, left column. English Translation attached. NPL-455.

Saechtling, Kunststoff-Taschenbuch, 24. Ausgabe 1989, S. 439, 477. English Translation attached. NPL-350.

Mutschler, W. Bakker D. J., "Temporarer Hautersatz", ZFA 1989, Heft 24, S. 714-720 als Sonderdruck. English Translation attached. NPL-305.

W. Fleischmann, U. Becker, M. Bischoff, H. Hoekstra, "Vacuum sealing: indication, technique, and results", Eur. J. Orthop & Traumato (1995) 5:37-40. NPL-158.

Argenta LC, Morykwas MJ. Vacuum-assisted closure: a new method for wound control and treatment: clinical experience. Ann Plast Surg 1997;38: 563-577 WFU-31.

Morykwas MJ, Argenta LC, Shelton-Brown EI, McGuirt W. Vacuum-assisted closure: a new method for wound control and treatment: animal studies and basic foundation. Ann Plast Surg 1997; 38:553-62 WFU-29.

Davydov IA, Larichev AB, Smirnov AP, Flegontov VB. Vakuumterapiia v lechenii ostrykh gnoinykh zabolevanii miagkikh tkanei I gnoinykh ran. [Vacuum therapy of acute suppurative diseases of soft tissues and suppurative wounds]. Russian Vestnik Khirurgii Imeni I—I—Grekova 1988; 141: 43-6 with Eng.Trans. DV10.

Davydov IA, Abramov AI, Larichev AB. Vakuum-terapiia v preduprezhdenii posleopératsionnoi ranevoi infektsii. [Vacuum therapy in the prevention of postoperative wound infection]. Russian Vestnik Khirurgii Imen I—I—Grekova 1991; 147:91-5, with English Translation. DV12.

Iankov NI. Simuliatsiia konsolidatsii perelomov nizhnei cheliusti vaktuumnoi terapiei. [Stimulation of consolidation of mandibular fractures by means of vacuum therapy] Russian. Stomatologiia 1971; 50: 86, with Eng. Trans. NPL-217.

Inoiatov IM, Aleksandrov VB. Lechenie promezhnostnoi rany posle amputatsii priamoi kishki vakuum-aspiratsiei. [Vacuum aspiration in the treatment of the perineal wound following extirpation of the rectum]. Russian. Khirurgiia 1971; 47: 74-8, with English Translation. NPL-220.

Kochnev VA. Primenenie vakuum-drenazhnoi sistemy dlia profilaktiki posleopératsionnykh ranevykh oslozhnenii u bol'nykh opukholiami. [The use of a vacuum drainage system in the prevention of postoperative wound complications in tumor patients]. Russian. Voprosy Onkologii 1967; 13:102-5, w/Eng. Trans. NPL-239.

Mirazimov BM. Svobodnaia Kozhnaie plastika stopy s podgotovkoi ranevoi poverkhnosti vakumiravaniem [Free skin graft of the foot with vacuum preparation of the wound surface]. Russian. Orthopediia Travmatologiia I Protezirovanie 1966;27:19-22, with English Translation. NPL-291.

Mirazimov BM, Vasina TA, Mezhericher MI. Mikroflora dlitel'no nekazhivaiushchikh ran i effektivnost' metoda vakuumirovaniia. [Microflora of prolonged non-healing wounds and the effectiveness of the vacuum evaporative method]. Russian. Khirurgiia 1967; 43: 40-3, with English Translation. NPL-290.

Mirazimov BM. Vorbereitung von Wunden und Geschwuren zur Hautplastik unter Anwendung der Vakuumierung [Preparation of wounds and abcesses for dermatoplasty by means of a vacuum device]. German. Beitrage zur Orthopadie und Traumatologie 1967; 14:224-30, with Eng. Translation. NPL-292.

Netudykhatka O. Vliianie nizkogo dozirovannogo vakuuma na techenie reparativnogo protsessa v kostnoi tkani [Effect of low vacuum on the course of the reparative process in bone tissue]. Russian. Voprosy Kurortologii, Fizioterapii i Lechebnoi Fizicheskoi Kultury 1972; 37:411-5, w/Eng. Trans. NPL-311.

Volkov LA. Isporzovanie vakuum-drenazhnoi sistemy v khirurgicheskoi praktike. [Use of vacuum-drainage system in surgical practice]. Russian. Klinicheskaia Khirurgiia. 1973;7:54-5, with English Translation. NPL-423.

Teder H, Sanden G, Svedman P. Continuous Wound Irrigation in the Pig. J Invest Surg 1990;3:399-407 NPL-400.

Nakayama Y, Tomotari I, Soeda S. A New Method for the Dressing of Free Skin Grafts. Plast Reconstr Surg 1990;86:1216-1219 NPL-308.

Brock WB, Barker DE, Burns RP. Temporary Closure of open abdominal wounds: the vacuum pack. Amer Surg 1995;61:30-5 NPL-059.

Shein M, Saadia R, Jameson JR, Decker GAG. The "sandwich technique" in the Management of the Open Abdomen. Br J Surg 1986;73:369-70 NPL-363.

Broome A. Hansson L, Lundgren F, Smedberg S. Open Treatment of Abdominal Septic Catastrophies. World J. Surg 1983;7:792-6 NPL-061.

Vatanasapt V, Areemit S, Jeeravipoolvarn P, et al. Red rubber bulb, cheap and effective vacuum drainage. Journal of the Medical Association of Thailand 1989;72:193-7 NPL-417.

Brummelkamp WH, Taat CW, Slors JF. High-vacuum drainage and primary perineal wound closure in abdominoperineal excision of the rectum. Netherlands Journal of Surgery 1991;43:236-9 NPL-063.

Morykwas J, Argenta LC. Nonsurgical modalities to enhance healing and care of soft tissue wounds. Journal of the Southern Orthopaedic Association 1997;6:279-88 WFU-04.

Sames CP. Sealing of wounds with vacuum drainage [letter] Br Med J 1977;2:1123 NPL-353.

Greer SE, Longaker MT, Margiotta M. Preliminary Results from a Multicenter, Randomized, Controlled, Study of the Use of Subatmospheric Pressure Dressing for Pressure Ulcer Healing. Wound Repair and Regeneration 1999;7:255 NPL-087.

Greer SE, Longaker MT, Margiotta M, Matthews AJ, Kasabian A. The Use of Subatmospheric Pressure Dressing for the Coverage of Radial Forearm Free Flap Donor-Site Exposed Tendon Complications. Ann Plast Surg 1999;43:551-554 NPL-179.

Greer SE, Duthie E, Cartolano B, Koehler KM, Maydick-Youngberg D, Longaker MT. Techniques for Applying Subatmospheric Pressure Dressing to Wounds in Difficult Regions of Anatomy. JWOCN 1999;26:250-3 NPL-177.

Greer SE, Kasabian A, Thorne C, Borud L, Sims CD, Hsu M. The Use of Subatmospheric Pressure Dressing to Salvage a Gustilo Grade IIIb Open Tibia Fracture with Concomitant Osteomyelitis and Avert a Free Flap. Ann Plast Surg 1998;41:687 NPL-178.

Genecov DG, Schneider AM, Morykwas MJ, et al. A Controlled subatmospheric pressure dressing increases the rate of skin graft donor site reepithelialization. Ann Plast Surg 1998;40:219-25 WFU-28.

Mendez-Eastman S. Negative pressure wound therapy. Plastic Surgical Nursing 1998;18:27-9, 33-37 NPL-277.

Banwell P. Withey S, Holten I. The use of negative pressure to promote healing [letter; comment]. Brit J Plast Surg 1998;51:79 NPL-033.

Blackburn J H Boemi L, Hall WW. et al. Negative-pressure dressings as a bolster for skin grafts. Ann Plast Surg 1998;40:453-7 NPL-049.

Smith LA, Barker DE, Chase CW, et al. Vacuum Pack Technique of Temporary Abdominal Closure: A Four-Year Experience. Amer Surg 1997;63:1102-8 NPL-378.

McCulloch JM, Kemper CC. Vacuum-Compression Therapy for the Treatment of an Ischemic Ulcer. Physical Therapy 1993;73:165-9 NPL-270.

Mullner T, Mrkonjic L, Kwasny O, Vecsei V. The use of negative pressure to promote the healing of tissue defects: a clinical trial using the vacuum sealing technique [see comments]. Brit J Plast Surg 1997;50:194-9 NPL-302.

Mirazimov, B.M.: Free Skin Grafting of Wounds and Ulcers using the "Vacuum Treatment" Method. [Orthop. Travmatol. Protez., 28(1):54-58.] with English Trans. 1967 NPL-293.

Greer, Steven E., "Whither Subatmospheric Pressure Dressing?" The Institute of Reconstructive Plastic Surgery, The New York University Medical Center, New York, NY April Issue of Annals of Plastic Surgery 2000. NPL-180.

Registration No. 1982349. Owner, KCI Inc., 3440 E. Houston Street San Antonio Texas 78219. Source: United States Patent and Trademark Office official website. Filing date May 1, 1995 Registration Date Jun. 25, 1996 NPL-344.

Hidden Interest—A Special Report.; When Physicians Double as Entrepreneurs. The New York Times. 11pp. Nov. 30, 1999 NPL-133.

Defranzo, Anthony J., et al., "Vacuum-Assisted Closure for the Treatment of Degloving Injuries." Plastic and Reconstructive Surgery 104 (7) 2145-48: (1999). WFU-35.

Morykwas, Michael J., et al., "Use of Subatmospheric Pressure to Prevent Progression of Partial-Thickness Burns in a Swine Model". Journal of Burn Care & Rehabilitation 20 (1 Part 1): 15-21 (1999) WFU-03.

Morykwas, Michael J., et al., "Use of Subatmospheric Pressure to Prevent Doxorubicin Extravasation Ulcers in a Swine Model". Journal of Surgical Oncology 72:14-17 (1999). WFU-33.

Molnar, Joseph A., et al., "Single-Stage Approach to Skin Grafting the Exposed Skull". Plastic and Reconstructive Surgery 105(1): 174-177 (2000). WFU-32.

Schneider, Andrew M., et al., "A New and Reliable Method of Securing Skin Grafts to the Difficult Recipient Bed". Plastic and Reconstructive Surgery 102(4) 1195-98 (1998). WFU-30.

Rosser, Charles J., et al., "A New Technique to Manage Perineal Wounds". Infections in Urology 13(2) 45-47, 56 (2000). WFU-34.

Philbeck, Thomas E., et al., "The Clinical and Cost Effectiveness of Externally Applied Negative Pressure Wound Therapy in the Treatment of Wounds in Home Healthcare Medicare Patients". Ostomy/Wound Management 45(11) 41-44, 46-50 (1999). NPL-330.

Meara, John G., et al., "Vacuum-Assisted Closure in the Treatment of Degloving Injuries". Annals of Plastic Surgery 42(6) 589-594 (1999). NPL-273.

Obdeijn, Miryam C., et al., "Vacuum-Assisted Closure in the Treatment of Poststernotomy Mediastinitis". Ann Thorac Surgery 68 2358-60 (1999). NPL-315.

Mendez-Eastman, Susan., "When wounds won't heal". RN 20-24 (1998) NPL-282.

Hartnett, Jacqueline M., "Use of Vacuum-Assisted Wound Closure in Three Chronic Wounds". JWOCN 25 (6) 281-290 (1998). NPL-195.

Mendez-Eastman, Susan., "Use of Hyperbaric Oxygen and Negative Pressure Therapy in the Multidisciplinary Care of a Patient with Nonhealing Wounds". JWOCN 26(2) 67-76 (1999). NPL-281.

Wooding-Scott, Margaret et al., "No-Wound is Too Big for Resourceful Nurses". RN, Dec. 22-25, 1988, NPL-444.

Davydov, et al., "Pathenogenic mechanism of the effect of vacuum therapy on the course of the wound process". Khirurgiia, Jun. 1990 (with English translation). DV13.

Davydov, et al., "Vacuum therapy in the treatment of suppurative lactation mastitis". Vestn. Khir., Nov. 1986 (with English translation). DV8.

Davydov, et al., "Bacteriological and cytological evaluation of the vacuum therapy of suppurative wounds". Vestn. Khir., Oct. 1988 (with English translation). DV2.

Davydov, et al., "Basis of the use of forced early secondary suture in the treatment of suppurative wounds by the vacuum therapy method". Vestn. Khir., Mar. 1990 (with English translation). DV1.

Borzov, et al., "Vacuum therapy of some skin diseases". Vestn. Dermatol. Venerol., Aug. 1965 (with English translation). NPL-055.

M.J. Morykwas and L.C. Argenta, "Techniques in Use of V.A.C. Treatment (in English)", Acta Chir. Austriaca Supplement Nr. 150, 1998, p. 3-4 of 2-28. WFU-02.

Garcia-Rinaldi, et al., "Improving the Efficiency of Wound Drainage Catheters", J. Surg., 1975, pp. 372-373. NPL-169.

Raffl, et al. "The Five Year Survival Rate for Gastric Cancer: Statistical Study from Syracuse Medical Center", Cancer, 6:756-759, Jul. 1953. NPL-339.

Raffl, et al., The Use of Negative Pressure Under Skin Flaps After Radical Mastectomy, Ann. Surg. 136: 1048, Dec. 1952. NPL-340.

Marie Knight, "A Second Skin for Patients with Large Drainage Wounds," Nursing 6(1) p. 37, 1976. NPL-238.

Oscar Ramirez, "Optimal Wound Healing under Op-Site Dressing" Plas. & Recon. Surg., 73(3): 474-475; 1984. NPL-341.

Helen Bibleheiner, "Dealing with a Wound that Drains 1.5 Liters per Day," RN Aug. 1986. NPL-046.

Peter Schwab, "Primary Closure of the Perineal Wound After Proctectomy" Mayo Clin. Proc., Mar. 1974, vol. 49. NPL-362.

Interlocutory Decision in Opposition proceedings in favor of patentee (Wake Forest-Argenta, et al.) dated Feb. 17, 2003 EPOPWH2-06.

Letter Supplemental to Notice of Opposition to European Patent No. 0688189 dated Nov. 12, 2002. EPOPWH2-05.

Notice of Opposition to European Patent No. 0688189 dated Jun. 12, 2001. EPOPWH2-02.

Opposer's Appeal from Interlocutory Decision—dated Jun. 27, 2003. EPOPWH2-08.

Communication from EPO, Summons to Attend Oral Proceedings Pursuant to Rule 71(1) EPC, European Patent 0,620,720, 6 pages, Aug. 12, 2003. EPOPWHI-08.

Avery, C., et al., "Negative pressure wound dressing of the radial forearm donor site", International Journal of Oral Maxillofacial Surgery, 2000; 29, pp. 198-200. NPL-024.

Armstrong, David G., et al., "Outcomes of Subatmospheric Pressure Dressing Therapy on Wounds of the Diabetic Foot", Ostomy/Wound Management 2002; 48(4): 64-68. NPL-019.

Brown, Karen M., et al., "Vacuum-Assisted Closure in the Treatment of a 9-Year-Old Child with Severe and Multiple Dog Bite Injuries of the Thorax", Society of Thoracic Surgeons, 2001; 72:1409-1410. NPL-062.

Catarino, Pedro A., et al., "High-Pressure Suction Drainage via a Polyurethane Foam in the Management of Poststernotomy Mediastinitis", Ann Thorac Surg 2000; 70:1891-5. NPL-071.

Mendez-Eastman, Susan, RN, CPSN, CWCN, Clinical Management Extra, Guidelines for Using Negative Pressure Wound Therapy, Advances in Skin & Wound Care, Nov./Dec. 2001, vol. 14, No. 6, p. 314-323. NPL-278, NPL-686.

Cooper, Susan Mary, "Topical negative pressure in the treatment of pressure ulcers", Letters posted in the Journal of the American Acad of Dermatology, August, Part 1, 1999, p. 280. NPL-099.

Davydov, I.A., et al., "Concept of clinico-biological control of the wound", Vestnik khirurgii imeni I.I. Grekova, v. 146, issue 2, 1991, 132-6 (with English translation). DV5.

de la Torre, Jorge I., MD, et al., "Healing a Wound with an Exposed Herrington Road: A Case Study", Ostomy Wound Management, pp. 18-19, May 2002, vol. 48, Issue 5. NPL-108.

de Lange, M.Y., et al., "Vacuum-assisted closure: indications and clinical experience", Eur J Plast Surg (2000) 23:178-182. NPL-109.

Deva, Anand, K., et al., "Topical negative pressure in wound management", MJA, Vo. 173, pp. 128-131, Aug. 7, 2000. NPL-113.

Elwood, Eric T., et al., "Negative-Pressure Dressings in the Treatment of Hidradenitis Suppurativa", Ann Plast Surgery Jan. 2001; 46:49-51. NPL-136.

Evans, D. and Land, L., "Topical negative pressure for treating chronic wounds: a systematic review", British Journal of Plastic Surgery (2001), 54, 238-242. NPL-144.

Fabian, Thaddeus S., MD, "The Evaluation of Subatmospheric Pressure and Hyperbaric Oxygen in Ischemic Full-Thickness Wound Healing", The American Surgeon, Dec. 2000, vol. 66, 1136-1143. NPL-146.

Fenn, C.H. and Butler, P.E.M., "Abdominoplasty wound-healing complications: assisted closure using foam suction dressing", British Journal of Plastic Surgery (2001), 54, 348-351. NPL-150.

Giovannini, Uberto M., MD, "Negative Pressure for the Management of an Exposed Vascular Dacron Polyester Patch", Annals of Plastic Surgery, 47(5): 577-578, 2001. NPL-171.

Gustafsson, Ronny, MD, "Vacuum-assisted closure therapy guided by C-reactive protein level in patients with deep sternal wound infection", The Journal of Thoracic and Cardiovascular Surgery, vol. 123, No. 5, pp. 895-900, May 2002. NPL-181.

Gwan-Nulla, Daniel N., MD and Casal, Rolando S., MD, "Toxic Shock Syndrome Associated with the Use of the Vacuum-Assisted Closure Device", Ann Plastic Surgery 2001;47:552-554. NPL-183.

Hersh, Robert E., MD, et al., "The Vacuum-Assisted Closure Device as a Bridge to Sternal Wound Closure", Ann Plast Surg. 2001; 46: 250-254. NPL-203.

Heugel, Judson R., et al., "Treatment of the Exposed Achilles Tendon Using Negative Pressure Wound Therapy: A Case Report", Journal of Burn Care and Rehabilitation, May/Jun. 2002, vol. 23, No. 3, pp. 167-171. NPL-205.

Joseph, Emmanuella, MD, et al., "A Prospective Randomized Trial of Vacuum-Assisted Closure Versus Standard Therapy of Chronic Nonhealing Wounds", WOUNDS 2000: 12(3): 60-67. NPL-228.

Josty, I.C., et al., "Vacuum-assisted closure: an alternative strategy in the management of degloving injuries of the foot", British Journal of Plastic Surgery (2001), 54, pp. 363-365. NPL-229.

Kostiuchenok, B.M., et al., "Vacuum Treatment in the Surgical Management of Suppurative Wounds", Izdatelstvo Meditsina, St. Petersburg, Sep. 1986; 137(9): 18-21 (with English Translation). NPL-241.

Kovacs, Laszlo H., MD, "Necrotizing Fasciitis", Annals of Plastic Surgery, vol. 47, No. 6, Dec. 2001, pp. 680-682. NPL-242.

Kranser, Diane L., "Managing Wound Pain in Patients with Vacuum-Assisted Closure Devices", Ostomy Wound Management 2002; 48(5): 38-43. NPL-243.

Mendez-Eastman, Susan, RN, CPSN, CWCN, "wound therapy", Nursing2002, vol. 32, No. 5, May, pp. 59-63 and 1 sheet of quiz. NPL-280.

Mooney, James F., III., "Treatment of Soft Tissue Defects in Pediatric Patients Using the V.A.C. TM System", Clinical Orthopedics and Related Research, No. 376, pp. 26-31, Jul. 2000. WFU-26.

Scheufler, O., et al., "Problem-adapted application of vacuum occlusion dressings: case report and clinical experience", Eur J. Plast Surg (2000) 23: 386-390. NPL-360.

Sposato, G., et al., "Ambulant vacuum-assisted closure of skin-graft dressing in the lower limbs using a portable mini-VAC device", British Journal of Plastic Surgery (2001), 54, 235-237. NPL-385.

Tang, Augustine T.M., et al., "Novel application of vacuum assisted closure technique to the treatment of sternotomy wound infection", European Journal of Cardio-Thoracic Surgery 17 (2000) 482-484. NPL-396.

Wu, S.H., et al., "Vacuum therapy as an intermediate phase in wound closure: a clinical experience", Eur J Surg (2000) 23:174-177. NPL-449.

Zhivotaev VM. Vacuum therapy of postoperative infected wounds of the urinary bladder, Klinicheskaia Khiurgiia. 1970;5:36-39. (in Russian) (and 1 sheet printout from PubMed). NPL-453.

The Kremlin Papers... perspectives in wound care, "A collection of published studies complementing the research and innovation of wound care", Russian Medical Journal "Vestnik Khirurgii", 5 Russian Articles from 1986-1991, translated by BlueSky Medical Group Inc. © 2004. NPL-244.

Interlocutory decisions in Opposition proceedings in favor of patentee (Wake Forest-Argenta, et al.) dated May 19, 2004. EPOPWH1-13.

*Kinetic Concepts, Inc., et al.* vs. *Bluesky Medical Corporation, et al.*; Civil Action No. S 03 C 0832: Plaintiff's Original Complaint dated Aug. 28, 2003. BS-120.

*Kinetic Concepts, Inc., et al.* vs. *Bluesky Medical Corporation, et al.*; Civil Action No. SA 03 CA 0832: Plaintiffs' First Amended Complaint dated Sep. 8, 2003. BS-121.

*Kinetic Concepts, Inc., et al.* vs. *Bluesky Medical Corporation, et al.*; Civil Action No. SA 03 CA 0832: Defendant BlueSky Medical Corporation's Original Answer to Plaintiff's First Amended Complaint dated Sep. 30, 2003. BS-122.

*Kinetic Concepts, Inc., et al.* vs. *Bluesky Medical Corporation, et al.*; Civil Action No. SA 03 CA 0832: Answer, Additional Defenses, Counterclaims and Jury Demand of Medela, Inc. (Response due: Oct. 27, 2003—20 days after service) dated Oct. 6, 2003. BS-123.

*Kinetic Concepts, Inc., et al.* vs. *Bluesky Medical Corporation, et al.*; Civil Action No. SA 03 CA 0832: Plaintiff's Reply to Defendant BlueSky Medical Corporation's Counterclaim dated Oct. 23, 2003. BS-124.

*Kinetic Concepts, Inc., et al.* vs. *Bluesky Medical Corporation, et al.*; Civil Action No. SA 03 CA 0832: Summary of Appendix in Support of Medela AG's Motion to Dismiss for Lack of Personal Jurisdiction or, Alternatively, to Dismiss for Failure to State a Claim and for Partial Summary Judgment dated Oct. 24, 2003. BS-125.

*Kinetic Concepts, Inc., et al.* vs. *Bluesky Medical Corporation, et al.*; Civil Action No. SA 03 CA 0832: Original Answer of Defendant Patient Care Systems, Inc., dated Oct. 7, 2003. BS-126.

*Kinetic Concepts, Inc., et al.* vs. *Bluesky Medical Corporation, et al.*; Civil Action No. SA 03 CA 0832: Medela AG's Motion to Dismiss for Lack of Personal Jurisdiction or Alternatively, to Dismiss for Failure to State a Claim and for Partial Summary Judgment dated Oct. 24, 2003. BS-127.

*Kinetic Concepts, Inc., et al.* vs. *Bluesky Medical Corporation, et al.*; Civil Action No. SA 03 CA 0832: Plaintiff's Reply to Defendant Medela, Inc.'s Counterclaim dated Oct. 27, 2003. BS-128.

*Kinetic Concepts, Inc., et al.* vs. *Bluesky Medical Corporation, et al.*; Civil Action No. SA 03 CA 0832: Plaintiff's Response to Medela AG's Motion to Dismiss for Lack of Personal Jurisdiction, Motion to Dismiss for Failure to State a Claim, and Motion for Partial Summary Judgment, dated Nov. 10, 2003. BS-129.

3M™, Tegaderm Family of Transparent Dressings for Chronic Wounds, pp. 1-8 (2002). NPL-002.

Alper, Joseph C., et al., "The In Vitro Response of Fibroblasts to the Fluid that Accumulates Under a Vapor-Permeable Membrane". Journal of Investigative Dermatology, 84:513-515, 1985. NPL-013.

Alper, Joseph C., et al., "Use of the Vapor Permeable Membrane for Cutaneous Ulcers: Details of application and side effects", Journal of the American Academy of Dermatology, vol. 11, No. 5, Part I, Nov., 1984, pp. 858-866. (NPL-014).

Angermeier, Marla C., et al., "Vapor-Permeable Membrane Therapy for Ulcers of Osteomyelitis", J. Dermatol. Surg. Oncol 10:May 5, 1984, pp. 384-388. NPL-016.

Bourke, et al., "Comparison Between Suction and Corrugated Drainage After Simple Mastectomy: Report on Controlled Trial", Br. J. Surg., vol. 63, 1976, pp. 67-69. NPL-056.

ConstaVac™ Closed Wound Drainage System, Stryker Instruments, 2 pages. NPL-092.

Eaglstein, William H., "Experiences with Biosynthetic Dressings", Journal of the American Academy of Dermatology, vol. 12, No. 2, Part 2, Feb. 1985, pp. 434-440. NPL-129.

Falanga, Vincent, et al., "A Therapeutic Approach to Venous Ulcers", Journal of the American Academy of Dermatology, vol. 14, No. 5, Part 1, May 1986, pp. 777-784. NPL-147.

Friedman, S., et al., "Treatment of Dermabrasion Wounds with a Hydrocolloid Occlusive Dressing", Arch Dermatol, vol. 121, Dec. 1985, pp. 1486-1487. NPL-166.

Friedman, Stephen J., et al., "Management of Leg Ulcers with Hydrocolloid Occlusive Dressing", Arch. Dermatol., vol. 120, Oct. 1984, pp. 1329-1336. NPL-167.

Holland, K.T., et al., "A Comparison of the In Vivo Antibacterial Effects of OpSite, Tegaderm and Ensure dressings", Journal of Hospital Infection, 1985, 6, pp. 299-303. NPL-209.

Jeter, Katherine F., et al., "Wound Dressings of the Nineties: Indications and Contraindications", Clinics in Podiatric Medicine and Surgery, vol. 8, No. 4, Oct. 1991, pp. 799-816. NPL-224.

Katz, Stuart, et al., "Semipermeable Occlusive Dressings", Arch Dermatol., vol. 122, Jan. 1986, pp. 58-62. NPL-231.

Lewis, R.T., "Knitted Polypropylene (Marlex) Mesh in the Repair of Incisional Hernias", The Canadian Journal of Surgery, vol. 27, No. 2, Mar. 1984, pp. 155-157. NPL-256.

Lower Extremity Ulcers, Chapter 9, pp. 47-57. NPL-259.

Microtek Medica, Inc. "The Microtek Complete Closed Wound Drainage System", 6 pages. NPL-285.

Rovee, David T., et al., "Effect of Local Wound Environment on Epidermal Healing", Dept. of Skin Biology, Johnson & Johnson Research, New Brunswick, NJ, pp. 159-181 (1972). NPL-348.

Satas, Donatas, "Handbook of Pressure-Sensitive Adhesive Technology", Silicone Release Coatings, Van Nostand Reinhold Company, 1982, pp. 384-403. NPL-355.

Turner, T.D., "A Look at Wound Dressings", Health and Social Service Journal, May 4, 1979, pp. 529-531. NPL-405.

Turner, T.D., "Recent Advances in Wound Management Products", pp. 3-6 NPL-406.

Turner, T.D., "Semipermeable Films as Wound Dressings", Welsh School of Pharmacy, University of Wales, Great Britain (Jul. 31, 1984). NPL-407.

Turner, T.D., "The Development of Wound Management Products", Chronic Wound Care, pp. 31-46. NPL-408.

Turner, T.D., et al., "Wound Management Product Selection", Journal of Sterile Services Management, Apr. 1985, pp. 3-6. NPL-409.

Varghese, Mathew C., et al., "Local Environment of Chronic Wounds Under Synthetic Dressings", Arch. Dermatol, vol. 122, Jan. 1986, pp. 52-57. NPL-416.

Viljanto, J., "Cellstic: A Device for Wound Healing Studies in Man. Description of the Method", Journal of Surgical Research, 20, 1976, pp. 115-119. NPL-420.

Wagner, S.A., et al., "An individualized Plastic Intraoral Device for the Collection of Human Parotid Saliva", International Journal of Clinical Pharmacology, Therapy and Toxilogy, Vo. 22, No. 5, 1984, pp. 236-239. NPL-425.

Wilson, John L., et al., "Loss of Blood Volume in Spinal Surgery with Use of Closed Wound Suction: An Experimental Study", Southern Medical Journal, Jul. 1968, pp. 761-763, read before the Section on Orthopaedic and Traumatic Surgery, Southern Medical Association, 61st Annual Meeting, Miami Beach, FL, (Nov. 13-16, 1967). NPL-437.

Winter, G.D., "Healing of Skin Wounds and the Influence of Dressings on the Repair Process", pp. 46-60 of "Surgical dressings and wound healing: proceedings of a symposium held on Jul. 7-8, 1970 at the University of Bradford," Crosby Lockwood for Bradford University Press, (1971). NPL-439.

Kohlman, P., et al., "Pouching Procedure to Collect Drainage From Around a Biliary Drainage Catheter", Ostomy/Wound Management, Nov./Dec. 1991, pp. 47-50, V. 37. NPL-240.

Alper, J., "Recent Advances in Moist Wound Healing", Southern Medical Journal, Nov. 1986, pp. 1398-1404, V. 79, N.11. NPL-011.

Reid, D., "Information on Cupping or Using Suction Cups on Wounds and for Healing Purposes", from Chines Herbal Medicine (2 pages). NPL-345.

Sheppard, M.D., "Sealed drainage of wounds," The Lancet, Jun. 14, 1952, pp. 1174-1176 NPL-410.

Putney, F., "The Use of Continuous Negative Pressure After Laryngectomy and Radical Neck Dissection", Surgery, Gynecology & Obstetrics, Aug. 1956, pp. 244-246. NPL-336.

Pleupump MK II, printouts from websites, www.xenamedical.se and www.landstinget.sormland.se, Aug. 14, 2001 (12 pages). NPL-332.

Brummelkamp, W., et al., "High-vacuum Drainage and Primary Perineal Wound Closure in Abdominoperineal Excision of the Rectum", The Netherland Journal of Surgery, 1991, pp. 236-239, V. 43, No. 6. NPL-063.

"Wound Suction; Better Drainage With Fewer Problems", Nursing75, October, pp. 52-55 (1975). NPL-447.

Grams Aspirator, et al., Grams Medical, catalog pp. (3 pages) (prices as of Aug. 1991 and Sep. 1992). NPL-175.

Medela Dominant promotional literature (2 pages of photos) (labeled circa 1984-1985). NPL-274.

Engdahl, O., et al., "Quantification of Aspirated Air Volume Reduces Treatment Time in Pneumothorax", Eur Respir J., 1990, 3, pp. 649-652. NPL-140.

Usage Manual Pleurasug TDR (2 pages of diagrams with descriptions). NPL-412.

Spengler, M., et al., "Performance of Filtered Sump Wound Drainage Tubes", Surgery, Gynecology & Obstetricsq, Mar. 1982, pp. 333-336, vol. 154. NPL-384.

Hallstrom, B., et al., "Postoperative Course After Total Hip Arthroplasty: Wound Drainage Versus No Drainage", Orthopaedic Review, Jul. 1992, pp. 847-851. NPL-185.

Miles, W., et al., "A Method of Performing Abdominoperineal Excision for Carcinoma of the Rectum and of the Terminal Portion of the Pelvic Colon", The Lancet, Dec. 19, 1908, pp. 1812-1813. NPL-287.

Benjamin, P., "Faeculent Peritonitis: A Complication of Vacuum Drainage", Br. J. Surg., 1980, pp. 453-454, vol. 67. NPL-042.

Sagi, A., et al., "Burn Hazard From Cupping—An Ancient Universal Medication Still in Practice", Burns, 1988, pp. 323-325, vol. 14, No. 4. NPL-351.

Agrama, H., et al., "Functional Longevity of Intraperitoneal Drains", The American Journal of Surgery, Sep. 1976, pp. 418-421, vol. 132. NPL-009.

Magee, C., et al., "Potentiation of Wound Infection by Surgical Drains", The American Journal of Surgery, May 1976, pp. 547-549, vol. 131. NPL-264.

Birdsell, D., et al., "The Theoretically Ideal Donor Site Dressing",Annals of Plastic Surgery, Jun. 1979, pp. 535-537, vol. 2, No. 6. NPL-048.

Cruse, P., et al., "A Five-Year Prospective Study of 23,649 Surgical Wounds", Surgical Wounds/Cruse and Foord, Aug. 1973, pp. 206-210, vol. 107. NPL-105.

Aubrey, D., et al., "Treatment of the Perineal Wound After Proctectomy by Intermittent Irrigation", Arch. Surg., Oct. 1984, pp. 1141-1144, vol. 119. NPL-021.

Mayo, C., "The One-Stage Combined Abdominoperineal Resection for Carcinoma of the Rectum, Rectosigmoid and Sigmoid", Surgical Clinics of North America, Aug. 1939, pp. 1011-1019. NPL-268.

Draper, J., "Make the dressing fit the wound", Nursing Times, Oct. 9, 1985, pp. 32-35. NPL-122.

Schumann, D., et al., "Preoperative Measures to Promote Wound Healing", Nursing Clinics of North America, Dec. 1979, pp. 683-699, vol. 14, No. 4. NPL-361.

Besst, J., et al., "Wound Healing—Intraoperative Factors", Nursing Clinics of North America, Dec. 1979, pp. 701-712, vol. 14, No. 4. NPL-044.

Cooper, D., et al., "Postsurgical Nursing Intervention as an Adjunct to Wound Healing", Nursing Clinics of North America, Dec. 1979, pp. 713-726, Nursing Clinics of North America, vol. 14, No. 4 NPL-097.

O'Byrne, C., "Clinical Detection and Management of Postoperative Wound Sepsis", Nursing Clinics of North America, Dec. 1979, pp. 727-741, vol. 14, No. 4. NPL-316.

Keith, C., "Would Management Following Head and Neck Surgery", Nursing Clinics of North America, Dec. 1979, pp. 761-778, vol. 14, No. 4. NPL-233.

Tenta, L., et al., "Suction Drainage of Wounds of the Head and Neck", Surgery, Gynecology. & Obstetrics, Dec. 1989, p. 558, vol. 169. NPL-401.

Firlit, C., et al., "Surgical Wound Drainage: A Simple Device for Collection", journal of Urology, Aug. 1972, pp. 327, vol. 108. NPL-153.

Moloney, G., "Apposition and Drainage of Large Skin Flaps", Oxford, England, pp. 173-179 (Feb. 1957). NPL-296.

Worth, M., et al., "The Effectiveness of Bacterial Filtration in Vented Wound Drains", Journal of Surgical Research, 1979, pp. 405-407, 27. NPL-446.

Flynn, M., et al., "Promoting Wound Healing: Wound Healing Mechanisms", American Journal of Nursing, Oct. 1982, pp. 1544-1558. NPL-162.

Miles, W., "Technique of the Radical Operation for Cancer of the Rectum", The British Journal of Surgery, 1914-1915, pp. 292-305. NPL-286.

Hilton, P., "Surgical Wound Drainage: A Survey of Practices Among Gynaecologists in the British Isles", British Journal of Obstetrics and Gynaecology, Oct. 1988, pp. 1063-1069, vol. 95. NPL-207.

Milsom, I., et al., "An Evaluation of a Post-Operative Vacuum Drainage System", Current Medical Research and Opinion, 1979, pp. 160-164, vol. 6, No. 2. NPL-289.

Fox, J., et al., "The Use of Drains in Subcutaneous Surgical Procedures", The American Journal of Surgery, Nov. 1976, pp. 673-674, vol. 132. NPL-164.

Hilsabeck, J., "The Presacral Space as a Collector of Fluid Accumulations Following Rectal Anastomosis", American Society of Colon and Rectal Surgeons, (Oct. 1982), pp. 680-684, vol. 25, No. 7. NPL-206.

Hulten, L., et al., "Primary Closure of Perineal Wound After Protocolectomy or Rectal Excision", Acta Chir Scand 137, 1971, pp. 467-469. NPL-215.

Landes, R., "An Improved Suction Device for Draining Wounds", Arch. Surg., May 1972, pp. 707, vol. 104. NPL-248.

Hugh, T., "Abdominal Wound Drainage", The Medical Journal of Australia, May 4, 1987, pp. 505. NPL-214.

Etsenbud, D., "Modern Wound Management", Adadem Publishing, pp. 109-116 (Jan. 1999). NPL-134.

Eaglstein, W., et al., "Wound Dressings: Current and Future", Clinical and Experimental Approaches to Dermal and Epidermal Repair; Normal and Chronic Wounds, Progress in Clinical and Biological Research, vol. 365, © 1991 Wiley-Liss, Inc., pp. 257-265. NPL-128.

Bruno, P., "The Nature of Wound Healing", Nursing Clinics of North America, Dec. 1979, pp. 667-682, vol. 14, No. 4. NPL-064.

Bar-El, Y., et al., "Potentially Dangerous Negative Intrapleural Pressures Generated by Ordinary Pleural Drainage Systems", Chest, Feb. 2001, pp. 511-514, vol. 119, No. 2. NPL-036.

Agarwala, S., et al., "Use of Mini-Vacuum Drains in Small Surgical Wounds", Plastic and Reconstructive Surgery, Apr. 1998, pp. 1421-1422, vol. 101, n. 5. NPL-008.

Nasser, A., "The Use of the Mini-Flap Wound Suction Drain in Maxillofacial Surgery", Annals of the Royal College of Surgeons of England, 1986, pp. 151-153, vol. 68. NPL-309.

Hunt, T.K., et al. eds., "Dead Space" and "Drainage", Fundamentals of Wound Management, pp. 416-447 (1979). NPL-186.

Lumley, J., et al., "The Physical and bacteriological Properties of Disposable and Non-Disposable Suction Drainage Units in the Laboratory", Br. J. Surg, 1974, pp. 832-837, vol. 61. NPL-261.

Britton, B., et al., "A Comparison Between Disposable and Non-disposable Suction Drainage Units: A Report of a Controlled Trial", Br. J. Surg., 1979, pp. 279-280, vol. 66. NPL-057.

McFarlane, R., "The use of Continuous Suction Under Skin Flaps", British Journal of Plastic Surgery, pp. 77-86 (1958-1959). NPL-271.

Fay, M., "Drainage Systems: Their Role in Wound Healing", AORN Journal, Sep. 1987, pp. 442-455, vol. 46, No. 3. NPL-149.

Taylor, V., "Meeting the Challenge of Fistulas & Draining Wounds", Nursing80, June, pp. 45-51. NPL-398.

Orgill, D., "Curent Concepts and Approaches to Would Healing", Critical Care Medicine, Sep. 1988, pp. 899-908, vol. 16, No. 9. NPL-320.

Part III. Resolving Selected Clinical Dilemmas, pp. 17-20. NPL-328.

"Making Sense of Wound Drainage", Nursing Times, Jul. 5, 1989, pp. 40-42, vol. 85, No. 27. NPL-265.

Manualectric Breastpump, Catalog pages (4 pages), diagrams and descriptions. NPL-266.

Harkiss, K., "Leg Ulcers Cheaper in the Long Run", Community Outlook, Aug. 1985, pp. 19, 21, 22, 24 & 26 NPL-190, NPL-601.

Westaby, S. (Editor), "Wound Care No. 43; Which Dressing and Why", Nursing Times Jul. 21, 1982, pp. 41-44. NPL-434.

OpSite Wound Dressings, "Do Your Pressure Sore Dressings Shape Up to the OpSite Standard", 2 pages of advertisements. NPL-319.

Dow Corning Silastic® Foam Dressing: A New Concept in the Management of Open Granulating Wounds, 2 pages of advertisements. NPL-121.

Cobb, J., "Why Use Drains", The Journal of Bone and Joint Surgery, Nov. 1990, pp. 993-995, vol. 72-B, No. 6. NPL-088.

Garcia-Rinaldi, R., "Improving the Efficiency of Wound Drainage Catheters", The Journal of Surgery, Sep. 1975, pp. 372-373, vol. 130. NPL-169.

$PLEUR_X$ Pleural Catheter, Denver Biomedical, 4 pages of brochure. NPL-334.

Silvis, R., et al., "The Use of Continuous Suction Negative Pressure Instead of Pressure Dressing", Annals of Surgery, Aug. 1955, pp. 252-256, vol. 142, No. 2. NPL-374.

Van Way, C., "Prevention of Suction-Induced Gastric Mucosal Damage in Dogs", Gastric Suction, 1987, pp. 774-777, vol. 15, No. 8. NPL-415.

Moserova, J., "The Healing and Treatment of Skin Defects", pp. 103-151 (1989) NPL-299.

Rabkin, J., et al., "Infection and Oxygen", Problem Wounds: The Role of Oxygen, pp. 1-15 (1987). NPL-338.

Paradise Valley Hospital, The Center for Wound Healing and Hyperbaric Medicine, 3 pages of brochure. NPL-326.

DuoDERM Hydroactive™ Dressing, "In wound management—Now, a proven environment for fast healing", 1 page advertisement. NPL-126.

Howmedica porto-vac®, "Gentle, Steady Wound Drainage", 1 page advertisement. NPL-212.

Silicone from CUI (Cox-Uphoff International), "Flexability", 1 page advertisement. NPL-371.

Curtin, L., "Wound Management: Care and Cost—An Overview", Nursing Management, Feb. 1984, pp. 22-25, vol. 15. NPL-106.

Grabowski, S., "Leczenie ran z zastosowaniem podcisnienia", article, pp. 19-21, English abstract on p. 21 and 1 sheet printout from PubMed, (Jan. 1, 1964). NPL-174.

Royle, G., et al., "Disposable Drains", Annals of the Royal College of Surgery of England, 1984, 1 page, vol. 66. NPL-349.

Meehan, P., "Open Abdominal Wounds: A Creative Approach to a Challenging Problem", Pregressions, 1992, pp. 3-8, 11, vol. 4, No. 2. NPL-276.

Stansby, G., et al., "Vacuum Drainage of Groin Wounds After Vascular Surgery", Br. J. Surg., Oct. 1990, pp. 1194-1195, vol. 77, No. 10. NPL-391.

Edlich, R., et al., "Evaluation of a New, Improved Surgical Drainage System", The American Journal of Surgery, Feb. 1985, pp. 295-298, vol. 149. NPL-130.

Broader, J., et al., "Management of the Pelvic Space After Proctectomy", Br. J. Surg., 1974, pp. 94-97, vol. 61. NPL-058.

Ayoub, M., et al., "A study of cutaneous and intracompartmental limb pressures associated with the combined use of tourniquets and plaster casts", May 1986, pp. 497, vol. 68-B, No. 3. NPL-025.

Cooper, D., "Optimizing Wound Healing: A Practice Within Nursing's Domain", Nursing Clinics of North America, Mar. 1990, pp. 165-180, vol. 25, No. 1. NPL-095.

Cooper, D., "Wound Healing", Nursing Clinics of North America, pp. 163-164 (Mar. 1990). NPL-096.

Hollis, H., et al., "A Practical Approach to Wound Care in Patients With Complex Enterocutaneous Fistulas", Surgery, Gynecology & Obstetrics, Aug. 1985, pp. 178-180, vol. 161. NPL-210.

Fingerhut, A., "Passive vs. Closed Suction Drainage After Perineal Would Closure Following Abdominoperineal Rectal Excision for Carcinoma", Dis Colon Rectum, Sep. 1995, pp. 926-932, vol. 38, No. 9. NPL-152.
Cook Pneumothorax Catheter Set, Wayne Pneumothorax Catheter Set, Emergency Medicine, Videotape advertisement. NPL-094.
Schaffer, D., "Closed Suction", Nursing97, Nov., http://www.springnet.com, pp. 62-64. NPL-357.
Carroll, P., "The Principles of Vacuum and Its Use in the Hospital Environment", Ohmeda, pp. 1-30 and cover sheet. NPL-070.
Morykwas, M.J., et al., "Use of Negative Pressure to Increase the Rate of Granulation Tissue Formation in Chronic Open Wounds", The FASEB Journal, (799-800), Feb. 19, 1993. WFU-13.
Orringer, J.S., et al., "Management of Wounds in Patients with Complex Enterocutaneous Fistulas", Surgery, Gynecology & Obstetrics, Jul. 1987, vol. 165. NPL-323.
Kinetic Concepts, Inc., et al., v. Bluesky Medical Corporation, et al., Civil Action No. SA-03-CA-0832-RF, U.S. Dist. Count, W. Dist. of TX San Antonio Div., Report of Katherine F. Jeter, Nov. 28, 2004. BS-11.
Swearingen, P.L., "The Addison-Wesley Photo-Atlas of Nursing Procedures", 9 pages, © 1984. NPL-393.
Mulder, G.D, et al., Clinicians' Pocket Guide to Chronic Wound Repair, Wound Healing Publications Second Edition, 1992, pp. 1-107. NPL-300.
Opposition to EP 0,620,720, Appeal of Opponent Paul Hartmann AG, dated Sep. 20, 2004 (with English translation). EPOPWII1-15.
Opposition EP to 0,620,720, Patentee's Grounds of Appeal dated Sep. 29, 2004, 31 pages. EPOPWH1-18.
Peacock, E.E., Jr., Wound Repair:, Repair of Skin Wounds, 1984, pp. 172-175. NPL-329.
Murray, J., et al., "On the Local and General Influence on the Body if Increased and Diminished Atmospheric Pressure", The Lancet, V. 1, 1834-1835, pp. 909-917. NPL-303.
Herrmann, L., et al., "The Conservative Treatment of Arteriosclerotic Peripheral Vascular Diseases", pp. 750-760 (Oct. 1934). NPL-199.
Versatile 1 Wound Vacuum System™ for the Promotion of Wound Healing, Wound Application instructions, 1 page advertisement. NPL-418.
Bluesky Medical "The Versatile One!™", Wound Drainage and More, 1 page advertisement. (Labeled Spring 2003). NPL-050.
Chariker-Jeter® Wound Sealing Kit, Would Application Instructions, 1 page advertisement. NPL-078.
Kinetic Concepts, Inc., et al., v. Bluesky Medical Corporation, et al., Civil Action No. SA-03-CA-0832-RF, U.S. District Court, W. Dist. of Texas San Antonio Div., Plaintiffs' Brief on Claim Construction dated Mar. 7, 2005. BS-151.
Kinetic Concepts, Inc., et al., v. Bluesky Medical Corporation, et al., Civil Action No. SA-03-CA-0832-RF, U.S. District Court, W. Dist. of Texas San Antonio Div., Medela AG and Medela, Inc's Opening Memorandum Regarding Construction of the Patent Claims dated Mar. 7, 2005. BS-152.
Kinetic Concepts, Inc., et al., v. Bluesky Medical Corporation, et al., Civil Action No. SA-03-CA-0832-RF, U.S. District Court, W. Dist. of Texas San Antonio Div., BlueSky Medical Group Incorporated Opening Markman Brief Regarding U.S. Patent Nos. 4,969,880 and 5,636,643. BS-153.
Kinetic Concepts, Inc., et al., v. Bluesky Medical Corporation, et al., Civil Action No. SA-03-CA-0832-RF, U.S. District Court, W. Dist. of Texas San Antonio Div., Plaintiffs' Responsive Claim Construction Brief dated Mar. 28, 2005. BS-148.
Kinetic Concepts, Inc., et al., v. Bluesky Medical Corporation, et al., Civil Action No. SA-03-CA-0832-RF, U.S. District Court, W. Dist. of Texas San Antonio Div., Declaration of Michael J. Morykwas in Support on Plaintiffs' Responsive Claim Construction Brief dated Mar. 24, 2005. BS-149.
Kinetic Concepts, Inc., et al., v. Bluesky Medical Corporation, et al., Civil Action No. SA-03-CA-0832-RF, U.S. District Court, W. Dist. of Texas San Antonio Div., Declaration of Wilson C. Hayes in Support on Plaintiffs' Responsive Claim Construction Brief dated Mar. 25, 2005. BS-150.
Johnson, Frank E., "An Improved Technique for Skin Graft Placement Using a Suction Drain", pp. 585-586 (Dec. 1984). NPL-226.

Dewan, P.A., et al., "An Alternative Approach to Skin Graft Donor Site Dressing", Aust. N.Z.J. Surg. 1986, 56, 509-510. NPL-116.
Kinetic Concepts, Inc., et al., v. Bluesky Medical Corporation, et al., Civil Action No. SA-03-CA-0832-RF, U.S. District Court, W. Dist. of Texas San Antonio Div., Plaintiffs' Reply Brief on Claim Construction dated Apr. 18, 2005. BS-147.
Kinetic Concepts, Inc., et al., v. Bluesky Medical Corporation, et al., Civil Action No. SA-03-CA-0832-RF, U.S. District Court, W. Dist. of Texas San Antonio Div., Medela AG and Medela, Inc.'s Response on Claim Construction dated Mar. 28, 2005. BS-154.
Kinetic Concepts, Inc., et al., v. Bluesky Medical Corporation, et al., Civil Action No. SA-03-CA-0832-RF, U.S. District Court, W. Dist. of Texas San Antonio Div., Bluesky Medical Group Incorporated's Opposition Markman Brief Regarding U.S. Patent Nos. 4,969,880 and 5,636,643. BS-155.
Opposition EP to 0,620,720, Third Party Observations dated Feb. 15, 2005. EPOPWH1-19.
Kinetic Concepts, Inc., et al., v. Bluesky Medical Corporation, et al., Civil Action No. SA-03-CA-0832-RF, U.S. District Court, W. Dist. of Texas San Antonio Div., Plaintiffs' Markman Presentation of May 12, 2005. BS-156.
Kinetic Concepts, Inc., et al., v. Bluesky Medical Corporation, et al., Civil Action No. SA-03-CA-0832-RF, U.S. District Court, W. Dist. of Texas San Antonio Div., Blue Sky Medical Corp.'s Markman Presentation dated May 12, 2005. BS-157.
Kinetic Concepts, Inc., et al., v. Bluesky Medical Corporation, et al., Civil Action No. SA-03-CA-0832-RF, U.S. District Court, W. Dist. of Texas San Antonio Div., Medela's Markman Presentation dated May 12, 2005. BS-158.
Opposition EP to 0,620,720, Response of Opponent Paul Hartmann AG dated Apr. 25, 2005 (with English translation). EPOPWH1-17.
Davies , J.W.L, "Synthetic materials for covering burn wounds: Progress towards perfection. Part I. Short term dressing materials", Burns, Nov. 1983;10(2), 94-103. NPL-107.
Lamke, L.O., et al., "The evaporative water loss from burns and the water-vapour permeability of grafts and artificial membranes used in the treatment of burns", Burns, 3, 159-165, 1977. NPL-247.
Barnett, A., et al., "Comparison of Synthetic Adhesive Moisture Vapor Permeable and Fine Mesh Gauze Dressings for Split-Thickness Skin Graft Donor Sites", The American Journal of Surgery, vol. 145, Mar. 1983, pp. 379-381. NPL-038.
Alper, J., et. al., "Moist wound healing under a vapor permeable membrane", Journal of the American Academy of Dermatology, vol. 8, No. 3, Mar. 1983, pp. 347-353. NPL-012.
James, J.H., et. al., "The use of Opsite, A Vapour Permeable Dressing, on Skin Donor Sites", British Journal of Plastic Surgery (1975), 28, 107-110. NPL-222.
Nahas, L.F., et al., "Use of Semipermeable Polyurethane Membrane for Skin Graft Dressings", Plastic and Reconstructive Surgery, Jun. 1981, pp. 791-792. NPL-306.
Edlich, R.F., et al., "Surgical Devices in Wound Healing Management", Wound Healing Biochemical & Clinical Aspects, W.B. Saunders Company, © 1992, pp. 581-599. NPL-131.
Orr, RK, et al., "Early Discharge After Mastectomy. A Safe Way of Diminishing Hospital Cost", Am Surg. Mar. 1987; 53(3) Abstract. NPL-322.
Otolaryngology, Head and Neck Surgery, The C.V. Mosby Company, © 1986, pp. 1716, 1724 and 2521. NPL-324.
Otolaryngology, vol. III, Head and Neck, W.B. Saunders Company, © 1980, pp. 2963. NPL-325.
Lore, Jr., J.M., "An Atlas of Head and Neck Surgery", Second Edition, vol. II, W.B. Saunders.Company, © 1973. NPL-258.
Kinetic Concepts, Inc., et al., v. Bluesky Medical Corporation, et al., Civil Action No. SA-03-CA-0832-RF, U.S. District Court, W. Dist. of Texas San Antonio Div., Letter Brief from BlueSky Medical dated May 31, 2005. BS-159.
Kinetic Concepts, Inc., et al., v. Bluesky Medical Corporation, et al., Civil Action No. SA-03-CA-0832-RF, U.S. District Court, W. Dist. of Texas San Antonio Div., Plaintiff's First Letter Brief from Markman hearing dated May 26, 2005. BS-160.

*Kinetic Concepts, Inc., et al.*, v. *Bluesky Medical Corporation, et al.*, Civil Action No. SA-03-CA-0832-RF, U.S. District Court, W. Dist. of Texas San Antonio Div., Plaintiffs Second Letter Brief from Markman hearing dated May 31, 2005. BS-161.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Transcription of Videotaped Deposition of Louis C. Argenta, M.D., Apr. 29, 2005. BS-68.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Transcription of Videotaped Deposition of Michael Allan Batalia, PhD. Jan. 12, 2005. BS-69.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Transcription of Videotaped Deposition of Michael John Morykwas, PhD. Jan. 13, 2005. BS-70.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Defendents Medela AG and Medela, Inc.'s Motion for Leave to Amend Designation of Expert Witnesses dated May 18, 2005. BS-162.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Plaintiffs' Answer to Defendant Bluesky Medical.Group Incorporated's Crossclaim dated Jun. 1, 2005. BS-163.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Plaintiffs' Answer to Defendant Richard Weston's Counterclaim dated Jun. 1, 2005. BS-164.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Plaintiffs' Answer to Defendant Medela Inc.'s Amended Counterclaims dated Jun. 1, 2005. BS-165.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Plaintiffs' Answer to Defendant Medela AG's Amended Counterclaims dated Jun. 1, 2005. BS-166.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Objections and Answers to Medela's Supoena in a Civil Case for Production of Documents and Deposition on Written Questions to Wake Forest University Baptist Medical Center dated Jun. 1, 2005. BS-167.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Medela, Inc. and Medela AG's Reply in Support of.Motion for Leave to File Amended Answers to Third Amended Complaint, Additional Defenses, Second Amended Counterclaims and Jury Demands dated Jun. 1, 2005. BS-168.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Plaintiffs' Opposition to Medela AG and Medela, Inc.'s Motion for Leave to Amend Designation of Expert Witnesses and Request for Hearing dated Jun. 1, 2005. BS-169.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Objections and Answers to Medela, Inc.'s Supoena in a Civil Case and Deposition on Written Questions to Dr. Joseph Molnar and Dr. Lawrence Webb dated Feb. 24, 2005. BS-170.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Deposition transcript with Exhibits of Shelly Taylor dated Nov. 23, 2004. BS-71.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Deposition transcript with Exhibits of Michael Miller, D.O. dated Mar. 8, 2005. BS-72.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Medela AG's First Supplemental Response to Plaintiffs' First Interrogatories to Defendant Medela AG dated Jul. 13, 2005. BS-179.

*Kinetic Concepts, Inc., et al.*, v. *Bluesky Medical Corporation, et al.*, Civil Action No. SA-03-CA-0832-RF, U.S. District Court, W. Dist. of Texas San Antonio Div., Medela Inc.'s First Supplemental Response to Plaintiffs' First Interrogatories to Defendant Medela, Inc. dated Aug. 16, 2005. BS-180.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Deposition transcript with Exhibits of Matthew C. Dairman, Feb. 3, 2005. BS-73.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Deposition transcript with Exhibits of Ronald C. Hamaker, May 26, 2005. BS-74.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Deposition transcript with Exhibits of Mordechai Twena, Jan. 25, 2005. BS-75.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Plaintiffs' Preliminary Proposed Constructions of Newly Asserted Claims From the '643 and '081 Patents dated Sep. 12, 2005. BS-181.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Plaintiffs' Opposition to Defendant Bluesky Medical Group Incorporated's and Richard Weston's Motion for Summary Judgment on the '643 Patent, including Declaration of Wilson C. Hayes in Support Thereof including Exhibits. BS-182.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Plaintiffs' Opposition to Defendant Bluesky Medical Group Incorporated's and Richard Weston's Motion for Summary Judgment on the '880 Patent, including Declaration of Wilson C. Hayes in Support Thereof including Exhibits. BS-183.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Answer to Fourth Amended Complaint, Additional Defenses, Third Amended Counterclaims and Jury Demand of Defendant Medela AG, Jul. 18, 2005. BS-184.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Answer to Fourth Amended Complaint, Additional Defenses, Third Amended Counterclaims and Jury Demand of Defendant Medela, Inc., Jul. 18, 2005. BS-185.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Expert Report with Exhibits of Valery Gilevich (Dec. 14, 2004). BS-49.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Medela, Inc., and Medela AG's Motion for Entry of Amended Protective Order with Exhibits dated Oct. 7, 2005. BS-186.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Videotaped Deposition transcript of Carr Lane Quackenbush dated Oct. 6, 2004. BS-79.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Defendant Medela AG's Answers to Plaintiffs' Second Interrogatories dated Oct. 7, 2005. BS-187.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Medela AG's Affidavit of Mitchell D. Lukin Pursuant to Local Rule CV-33(a) dated Oct. 7, 2005. BS-188.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Defendant Medela AG's Response to Plaintiffs' Second Request for Production of Documents dated Oct. 7, 2005. BS-189.

*Kinetic Concepts, Inc., et al., v. Bluesky Medical Corporation, et al.*, Civil Action No. SA-03-CA-0832-RF, U.S. District Court, W. Dist. of Texas San Antonio Div., Defendant Medela Ag's Response to Plaintiffs' Third Request for Production of Documents dated Oct. 7, 2005. BS-190.

*Kinetic Concepts, Inc., et al., v. Bluesky Medical Corporation, et al.*, Civil Action No. SA-03-CA-0832-RF, U.S. District Court, W. Dist. of Texas San Antonio Div., Defendant Medela, Inc.'s Response to Plaintiffs' Second Request for Production of Documents dated Oct. 7, 2005. BS-191.

*Kinetic Concepts, Inc., et al., v. Bluesky Medical Corporation, et al.*, Civil Action No. SA-03-CA-0832-RF, U.S. District Court, W. Dist. of Texas San Antonio Div., Plaintiffs' Opening Brief on Claim Construction of Disputed Claim Terms From the '643 and '081 Patents with Exhibits dated Oct. 6, 2005. BS-192.

*Kinetic Concepts, Inc., et al., v. Bluesky Medical Corporation, et al.*, Civil Action No. SA-03-CA-0832-RF, U.S. District Court, W. Dist. of Texas San Antonio Div., Medela, Inc.'s Second Set of Interrogatories to Wake Forest University Health Sciences dated Oct. 7, 2005. BS-193.

*Kinetic Concepts, Inc., et al., v. Bluesky Medical Corporation, et al.*, Civil Action No. SA-03-CA-0832-RF, U.S. District Court, W. Dist. of Texas San Antonio Div., Medela, Inc.'s Eighth Set of Requests for Production To Plaintiffs Kinetic Concepts, Inc., KCI Licensing, Inc., KCI USA, Inc., and Wake Forest University Health Sciences dated Oct. 7, 2005. BS-194.

*Kinetic Concepts, Inc., et al., v. Bluesky Medical Corporation, et al.*, Civil Action No. SA-03-CA-0832-RF, U.S. District Court, W. Dist. of Texas San Antonio Div., Order Grating Joint Motion to Extend Deadlines dated Sep. 30, 2005. BS-195.

*Kinetic Concepts, Inc., et al., v. Bluesky Medical Corporation, et al.*, Civil Action No. SA-03-CA-0832-RF, U.S. District Court, W. Dist. of Texas San Antonio Div., BlueSky Medical Group Inc.'s Additional Supplemental Discovery Production with Bates Labels and Cover Letter dated Sep. 30, 2005. BS-224.

*Kinetic Concepts, Inc., et al., v. Bluesky Medical Corporation, et al.*, Civil Action No. SA-03-CA-0832-RF, U.S. District Court, W. Dist. of Texas San Antonio Div., Joint Motion for Entry of Order Adopting the Parties' Stipulated Claim Term Constructions dated Oct. 6, 2005. BS-196.

*Kinetic Concepts, Inc., et al., v. Bluesky Medical Corporation, et al.*, Civil Action No. SA-03-CA-0832-RF, U.S. District Court, W. Dist. of Texas San Antonio Div., Order Adopting the Parties' Stipulated Claim Term Constructions. BS-197.

*Kinetic Concepts, Inc., et al., v. Bluesky Medical Corporation, et al.*, Civil Action No. SA-03-CA-0832-RF, U.S. District Court, W. Dist. of Texas San Antonio Div., Promotional Slide Presentation BlueSky Medical.Negative Pressure Wound Care with Versatile 1 Presentation Presented by Penny Campbell and Shelly Burdette-Taylor 27 page (dated Oct. 14, 2005). NPL-067.

*Kinetic Concepts, Inc., et al., v. Bluesky Medical Corporation, et al.*, Civil Action No. SA-03-CA-0832-RF, U.S. District Court, W. Dist. of Texas San Antonio Div., Defendant Bluesky Medical Group Inc. and Richard Weston's Reply to Plaintiffs Opposition to Defendant Bluesky Medical Group Inc. and Richard Weston's Motions for Partial Summary Judgment dated Sep. 28. 2005. BS-198.

*Kinetic Concepts, Inc., et al., v. Bluesky Medical Corporation, et al.*, Civil Action No. SA-03-CA-0832-RF, U.S. District Court, W. Dist. of Texas San Antonio Div., Order Granting Plaintiffs' Unopposed Motion to Supplement the Record for its response to Bluesky's Motion for Partial Summary Judgment dated Oct. 13, 2005. BS-200.

*Kinetic Concepts, Inc., et al., v. Bluesky Medical Corporation, et al.*, Civil Action No. SA-03-CA-0832-RF, U.S. District Court, W. Dist. of Texas San Antonio Div., Order Granting Medela, Inc. and Medela AG's Unopposed Motion to Extend Deadlines for Markman Briefing dated Oct. 13, 2005. BS-201.

*Kinetic Concepts, Inc., et al., v. Bluesky Medical Corporation, et al.*, Civil Action No. SA-03-CA-0832-RF, U.S. District Court, W. Dist. of Texas San Antonio Div., Plaintiffs' Unopposed Motion to Supplement the Record in Support of Their Response to Bluesky's Motion for Partial Summary Judgment on Counts Twelve, Thirteen, and Fifteen dated Oct. 10, 2005. BS-202.

Barillo, D., et al., "Management of Burns to the Hand", Wounds 15,(1):4-9, 2003 Health Management.Publications, Inc., Posted Feb. 12, 2003. NPL-037.

Medical Technology & Innovation, "Medical Technology is Extending Life, Reducing Costs", vol. 1, Issue 46, Dec. 4, 2000. NPL-275.

Wu, Lisa C., et al., "Vacuum-Assisted Closure for the Treatment of Sternal Wounds: The Bridge Between Debridement and Definitive Closure", printout from www.plasticsurgery.org., 3 pages (printout dated Apr. 20, 2005). NPL-448.

*Kinetic Concepts, Inc., et al., v. Bluesky Medical Corporation, et al.*, Civil Action No. SA-03-CA-0832-RF, U.S. District Court, W. Dist. of Texas San Antonio Div., Joint Claim Construction and Prehearing Statement dated Sep. 16, 2005. BS-204.

*Kinetic Concepts, Inc., et al., v. Bluesky Medical Corporation, et al.*, Civil Action No. SA-03-CA-0832-RF, U.S. District Court, W. Dist. of Texas San Antonio Div., Defendants' Opening Brief Regarding Claim Construction for the '081 Patent and Certain Claims of the '643 Patent dated Oct. 5, 2005. BS-203.

Bertone, A., "Management of Exuberant Granulation Tissue", Wound Management, pp. 551-562 (Dec. 1989). NPL-043.

Taber's Cyclopedic Medical Dictionary, Edition 18, pp. 937, 942 and 1375. NPL-394.

Harris, Ann, et al., "Hypergranulation Tissue: A Nontraumatic Method of Management", Ostomy/Would Management, vol. 40, No. 5, Jun. 1994. NPL-193.

Opposition EP to 0620720, Patentee Response to Grounds of Appeal Filed by Opponent, Paul Hartmann AG, with Exhibits dated Apr. 25, 2005. EPOPWH1-16.

Opposition EP to 0620720, Opponents Response to Grounds of Appeal Filed by Patentee (with translation), dated Apr. 25, 2005. EPOPWH1-17.

Opposition EP to 0620720, Patentees' Grounds of Appeal, dated Sep. 29, 2004. EPOPWH1-18.

Opposition EP to 0620720, Third-Party Communication dated Feb. 15, 2005 (R.G.C. Jenkins & Co.) EPOPWH1-19.

Opposition EP to 0620720, Interlocutory Decision dated May 19, 2004. EPOPWH1-13.

Opposition EP to 0620720, Communication of Patentee dated Nov. 25, 2003. EPOPWH1-12.

Opposition EP to 0620720, Third-Party Communication dated Nov. 12, 2003 (R.G.C. Jenkins & Co.) EPOPWH1-11.

Opposition EP to 0620720, Third-Party Communication dated Aug. 14, 2003. (R.G.C. Jenkins & Co.) EPOPWH1-09.

Opposition EP to 0620720, Communication of Patentee dated Nov. 9, 2003. EPOPWH1-10.

Webster's New Universal Unabridged Dictionary Deluxe Second Edition, p. 631. NPL-431.

Opposition EP to 0620720, Communication of Opponent Mondomed dated Aug. 8, 2001. (Margot MullerGerbes) EPOPWH1-07.

Opposition EP to 0620720, Communication of Opponent Mondomed dated May 3, 2001. (Margot MullerGerbes) EPOPWH1-06.

Opposition EP to 0620720, Communication of Patentee dated Sep. 22, 2000. EPOPWH1-05.

*Kinetic Concepts, Inc., et al., v. Bluesky Medical Corporation, et al.*, Civil Action No. SA-03-CA-0832-RF, U.S. District Court, W. Dist. of Texas San Antonio Div., Defendant Bluesky Medical Group Incorporated's and Richard Weston's Motion for Summary Judgment on the '643 Patent with Exhibits dated Aug. 10, 2005.. BS-205.

*Kinetic Concepts, Inc., et al., v. Bluesky Medical Corporation, et al.*, Civil Action No. SA-03-CA-0832-RF, U.S. District Court, W. Dist. of Texas San Antonio Div., Defendant Bluesky Medical Group Incorporated's and Richard Weston's Motion for Summary Judgment on the '880 Patent with Exhibits dated Aug. 10, 2005. BS-206.

Bier, A., et al., Bier's Hyperemic Treatment, "Hyperemia by suction apparatus", Hyperemia as a Therapeutic Agent, Chicago, IL, Roberts Publishing; 1905: 74-85. NPL-216.

*Kinetic Concepts, Inc., et al.*, v. *Bluesky Medical Corporation, et al.*, Civil Action No. SA-03-CA-0832-RF, U.S. District Court, W. Dist. of Texas San Antonio Div., Plaintiffs' Surreply Further Opposing Defendant Bluesky Medical Group Incorporated's and Richard Weston's Motions for Summary Judgment on the '643 and '880 Patents with Exhibits dated Oct. 14, 2005. BS-133.
Chariker-Jeter Technique Tutorial by Penny E. Campbell, Wound Care Solutions, 1 page tutorial chart. NPL-075.
Bluesky Medical, Negative Pressure Wound Therapy, Product Catalog Fall 2005, "Finally a choice . . . " 8 pages. NPL-053.
Chariker-Jeter Status Link from NPL-074 the website www.trademark.com/cbi-bin/tmlist, Oct. 14, 2005, 1 page. NPL-074.
Bluesky Medical Support, printout of webpages www.woundvacuum.com/Standard%20Pages/support_htm, Oct. 11, 2005, pp. 1-3. NPL-051.
*KCI et al.* v. *Blue Sky Medical Group et al.*, 2007-1340, 2007-1341, 2007-1342, Federal Circuit Court of Appeals, Case No. 2007-1340, Appellants Brief, with addendum, filed by Blue Sky on Oct. 19, 2007. CAFC1340-001.
*KCI et al.* v. *Blue Sky Medical Group et al.*, Case No. 2007-1340, -1341, -1342, Plaintiff-Cross Appellant's (Patent Owner's) Brief, with addendum chart, filed on Mar. 3, 2008. CAFC1340-002.
Healing of Full Thickness Defects in Swine NPL-197.
Opposition EP to 0,620,720, Summons to Oral Proceedings Appeal dated Dec. 21, 2005. EPOPWH1-20.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Plaintiffs Letter to Honorable Royal Furgeson dated Jan. 3, 2006. BS-130.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Defendants Letter to Honorable Royal Furgeson dated Jan. 3, 2006. BS-131.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Plaintiffs' Reply Claim Construction Brief with Exhibits dated Nov. 11, 2005. BS-132.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Plaintiffs' Surreply Further Opposing Defendant Bluesky Medical Group Incorporated's and Richard Weston's Motions for Summary Judgment on the '643 and '880 Patents with Exhibits dated Oct. 14, 2005. BS-133.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Plaintiffs' Opposition to Defendant Bluesky Medical Group. Incorporated's and Richard Weston's Motion for Summary Judgment on the '880 Patent with Exhibits dated Sep. 12, 2005. BS-134.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Defendant Bluesky and Richard Weston's First Amended Crossclaims and Answer to Plaintiffs' Fourth Amended Complaint, Counterlclaims, and Joinder of Wake Forest University dated Nov. 15, 2005. BS-135.
Webster, J.G., "Prevention of Pressure Sores", © IOP Publishing Ltd 1991, The Adam Hilger Series on Biomedical Engineering, pp. 199-223. NPL-430.
Garcia-Velasco, M., et al., "Compression Treatment of Hypertrophic Scars in Burned Children", The Canadian Journal of Surgery, V.21, No. 5, Sep. 1978, pp. 450-452. NPL-170.
Rose, M.P., et al., "The Clinical Use of a Tubular Compression Bandage, Tubigrip, for Burn-Scar Therapy: A Critical Anaylis", Burns (1985) 12, 58-64. NPL-347.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Defendant Bluesky and Richard Weston's Objections and.Responses to Plaintiffs' Fifth Request for Production dated Dec. 9, 2005. BS-136.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Defendants' Response Brief Regarding Second Claim Construction Hearing ('081 Patent and Certain Claims of the '643 Patent) with Exhibits dated Oct. 25, 2005. BS-137.
*Kinetic Concepts, Inc., et al.*, v. *Bluesky Medical Corporation, et al.*, Civil Action No. SA-03-CA-0832-RF, U.S.District Court, W. Dist. of Texas San Antonio Div., Defendant Medela, Inc.'s Objections and Responses to Plaintiffs' Sixth Request for Production of Documents dated Dec. 9, 2005. BS-138.
*Kinetic Concepts, Inc., et al.*, v. *Bluesky Medical Corporation, et al.*, Civil Action No. SA-03-CA-0832-RF, U.S.District Court, W. Dist. of Texas San Antonio Div., Defendant Bluesky and Richard Weston's First Amended.Crossclaim and Answer to Plaintiffs' Fourth Amended Complaint, Counterclaims, and Joinder of Wake Forest University dated Nov. 15, 2005. BS-139.
*Kinetic Concepts, Inc., et al.*, v. *Bluesky Medical Corporation, et al.*, Civil Action No. SA-03-CA-0832-RF, U.S.District Court, W. Dist. of Texas San Antonio Div., Plaintiffs' Responsive Claim Construction Brief on the Disputed Claim Terms from the '6443 and '081 Patents with Exhibits dated Oct. 25, 2005. BS-140.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Markman Hearing Medela Presentation, pp. 1-78. BS-245.
Opposition EP to 0,618,189 New European Patent Specification EP 0688189B2. EPOPWH2-01.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Supplemental Expert Report of Wilson C. Hayes, Ph.D. Concerning Infringement of Newly Asserted Claims of U.S. Patent Nos. 5,636,643 and 5,645,081 dated Dec. 19, 2005. BS-55.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Expert Report of Dennis P. Orgill, M.D., Ph.D. with Exhibits dated Dec. 29, 2005. BS-1.
Opposition EP to 0,618,189 Decision to Maintain the European Patent in Amended Form (Article 102(3) EPC) dated Apr. 22, 2005, 1 page. EPOPWH2-10.
Opposition EP to 0,618,189 Letter relating to Appeal Procedure dated Mar. 5, 2004, 10 pages. EPOPWH2-09.
Opposition EP to 0,618,189 Letter relating to Appeal Procedure dated Jun. 27, 2003. EPOPWH2-08.
Opposition EP to 0,618,189 Interlocutory Decision in Opposition Proceedings with Grounds for the Decision dated Feb. 17, 2003. EPOPWH2-06.
Opposition EP to 0,618,189 Minutes of the Oral Proceedings, Documents for the Maintenance of the Patent as Amended, Annex to the Communication dated Feb. 17, 2003. EPOPWH2-07.
Opposition EP to 0,618,189 Letter Pursuant to Rule 71a EPC and all Other Letter during Oral Proceedings dated Nov. 11, 2002. EPOPWH2-04.
Opposition EP to 0,618,189 Reply of the Patent Proprietor to the Notice(s) of Opposition dated Mar. 15, 2002. EPOPWH2-03.
Opposition EP to 0,618,189 Notice of Opposition dated Jun. 12, 2001. EPOPWH2-02.
Murray, Y., "Tradition Rather Than Cure", Wound Care, Nursing Times, Sep. 21, vol. 84, No. 38, 1988. NPL-304.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Plaintiffs Response to Claim Construction Reply Letter dated Jan. 6, 2006. BS-142.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Defendants Medela Claim Construction Letter dated Jan. 5, 2006. BS-143.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Expert Report of Harriet W. Hopf, M.D. On New Claims dated Jan. 4, 2006. BS-2.
*Kinetic Concepts, Inc., et al.*, v. *Bluesky Medical Corporation, et al.*, Civil Action No. SA-03-CA-0832-RF, U.S.District Court, W. Dist. of Texas San Antonio Div., Expert Report of Lydia Razran Stone, Ph.D. dated Dec. 29, 2005 with CV. BS-3.

*Kinetic Concepts, Inc., et al.*, v. *Bluesky Medical Corporation, et al.*, Civil Action No. SA-03-CA-0832-RF, U.S.District Court, W. Dist. of Texas San Antonio Div., Plaintiffs Fourth Amended Complaint with Declaration of.Trang Tran with Exhibits dated Jun. 30, 2005. BS-144.

*Kinetic Concepts, Inc., et al.*, v. *Bluesky Medical Corporation, et al.*, Civil Action No. SA-03-CA-0832-RF, U.S.District Court, W. Dist. of Texas San Antonio Div., Transcript Deposition of Michael John Morykwas dated Dec. 6, 2005 with Exhibits. BS-64.

Spurlock, Gareth, "The Management of Open Joint Injuries", Wound Management, Veterinary Clinics of North American Equina Practice, vol. 5, No. 3, Dec. 1989. NPL-386.

Tittel, K., et al., "VariDyne—new standards in postoperative wound drainge", Jahrgang 14 (1988), Nr. 2, April, vol. 14 (1988), No. 2, April, pp. 104-107. NPL-403.

Queen, D., et al., "The preclinical evaluation of the Water Vapour Transmission Rate Through Burn Wound Dressings", Biomaterials 1987 vol. 8, September, pp. 367-371. NPL-337.

Wood, R.A.B., et al., "Foam Elastomer Dressing in the Management of Open Granulating Wounds: Experience with 250 Patients", Br. J. Surg., vol. 64 (1977), pp. 554-557. NPL-443.

Waymack, J.P., et al., "An Evaulation of Aquaphor Gauze Dressing in Burned Children", Burns (1986) 12, 443-448. NPL-428.

Winter, George D., "Epidermal Wound Healing Under a New Polyurethane Foam Dressing (Lyofoam)", Plastic & Reconstructive Surgery, Nov. 1975, Vo. 56, No. 5, pp. 531-537. NPL-438.

*Kinetic Concepts, Inc., et al.*, v. *Bluesky Medical Corporation, et al.*, Civil Action No. SA-03-CA-0832-RF, U.S.District Court, W. Dist. of Texas San Antonio Div., Deposition Transcript of Doris Ritter-Wiegand with Exhibits dated Dec. 15, 2005. BS-65.

*Kinetic Concepts, Inc., et al.*, v. *Bluesky Medical Corporation, et al.*, Civil Action No. SA-03-CA-0832-RF, U.S.District Court, W. Dist. of Texas San Antonio Div., Transcript of Videotaped Deposition of Katherine Jeter with Exhibits dated Nov. 29, 2005. BS-66.

*Kinetic Concepts, Inc., et al.*, v. *Bluesky Medical Corporation, et al.*, Civil Action No. SA-03-CA-0832-RF, U.S.District Court, W. Dist. of Texas San Antonio Div., Supplemental Expert Report of Mark Chariker, M.D. dated Dec. 19, 2005. BS-24.

*Kinetic Concepts, Inc., et al.*, v. *Bluesky Medical Corporation, et al.*, Civil Action No. SA-03-CA-0832-RF, U.S.District Court, W. Dist. of Texas San Antonio Div., Expert Report of Vincent B. Pizziconi, Ph.D. with Exhjbits dated Dec. 23, 2005. BS-5.

*Kinetic Concepts, Inc., et al.*, v. *Bluesky Medical Corporation, et al.*, Civil Action No. SA-03-CA-0832-RF, U.S.District Court, W. Dist. of Texas San Antonio Div., Amended Order Construing Patent '643 Claims Terms dated Jan. 25, 2006. BS-145.

*Kinetic Concepts, Inc., et al.*, v. *Bluesky Medical Corporation, et al.*, Civil Action No. SA-03-CA-0832-RF, U.S.District Court, W. Dist. of Texas San Antonio Div., Order Construing Patents '643 and '081 Claim Terms dated Jan. 24, 2006. BS-146.

*Kinetic Concepts, Inc., et al.*, v. *Bluesky Medical Corporation, et al.*, Civil Action No. SA-03-CA-0832-RF, U.S.District Court, W. Dist. of Texas San Antonio Div., Expert Report of Michael A. O'Neil dated Jan. 4, 2006. BS-6.

*Kinetic Concepts, Inc., et al.*, v. *Bluesky Medical Corporation, et al.*, Civil Action No. SA-03-CA-0832-RF, U.S.District Court, W. Dist. of Texas San Antonio Div., Partial Transcript of Videotaped Deposition James Spahn dated May 4, 2005. BS-67.

*Kinetic Concepts, Inc., et al.*, v. *Bluesky Medical Corporation, et al.*, Civil Action No. SA-03-CA-0832-RF, U.S.District Court, W. Dist. of Texas San Antonio Div., Report of Professor Thomas K. Hunt, M.D., pp. 1-14, (with exhibits) Jan. 13, 2005. BS-29.

*Kinetic Concepts, Inc., et al.*, v. *Bluesky Medical Corporation, et al.*, Civil Action No. SA-03-CA-0832-RF, U.S.District Court, W. Dist. of Texas San Antonio Div., Report of Mark Chariker, M.D., pp. 1-8, Jan. 13, 2005. BS-8.

*Kinetic Concepts, Inc., et al.*, v. *Bluesky Medical Corporation, et al.*, Civil Action No. SA-03-CA-0832-RF, U.S.District Court, W. Dist. of Texas San Antonio Div., Report of James Spahn, M.D., pp. 1-6 and Exhibit C pp. 9-10, Jan. 6, 2005. BS-9.

*Kinetic Concepts, Inc., et al.*, v. *Bluesky Medical Corporation, et al.*, Civil Action No. SA-03-CA-0832-RF, U.S.District Court, W. Dist. of Texas San Antonio Div., Expert Report of Michael H. Baniak, pp. 1-79 and Exhibit D pp. 1-3 including un-published materials listed therein and Exhibit E pp. 1-5, Jan. 7, 2005. BS-10.

*Kinetic Concepts, Inc., et al.*, v. *Bluesky Medical Corporation, et al.*, Civil Action No. SA-03-CA-0832-RF, U.S. Dist. Count, W. Dist. of TX San Antonio Div., Report of Wilson C. Hayes, Ph.D, Nov. 29, 2004, pp. 1-15, and Exhibit C (2 pages). BS-12.

Banwell, P., et al., "Topical Negative Pressure TNP Focus Group Meeting", Proceedings, London, UK 2003, pp. 1-111. WFU-24.

Proceedings from the 2003 National V.A.C.® Education Conference, supplement to the Apr. 2004 Wounds, 40 pages. NPL-335.

Dieu, T., et al., "Too Much Vacuum-Assisted Closure", Anz J. Surg. 2003; 73: 1057-1060 NPL-117.

Chester, D., et al., "Adverse Alteration of Wound Flora with Topical Negative-Pressure Therapy: A Case Report", British Journal of Plastic Surgery, 2002, pp. 510-511. NPL-082.

Alvarez, A., et al., "Vacuum-Assisted Closure for Cutaneous Gastrointestinal Fistula Management", Gynecologic Oncology, 80, 413-416 (2001). NPL-015.

Nienhuijs, S.W., et al., "Can Topical Negative Pressure Be Used to Control Complex Enterocutaneous Fistulae?", Journal of Wound Care, V. 12, No. 9, Oct. 2003, pp. 343-345. NPL-313.

Erdmann, D., et al., "Abdominal Wall Defect and Enterocutaneous Fistula Treatment with the Vacuum-Assisted Closure (V.A.C.) System", Plastic and Reconstructive Surgery, vol. 108, No. 7, pp. 2066-2068 (Dec. 2001). NPL-141.

Maddin, W. Stuart, et al., "The Biological Effects of a Pulsed Electrostatic Field with Specific Reference to Hair", Pharmacology and Therapeutics, Jul.-Aug. 1990, V. 29, No. 6, pp. 446-450. NPL-263.

Morykwas, M. and Argenta, L., "Use of Negative Pressure to Increase the Rate of Granulation Tissue Formation in Chronic Open Wounds", The FASEB Journal, Experimental Biology '93, New Orleans, Louisiana, Mar. 28-Apr. 1, 1993, 800 (Feb. 19, 1993). WFU-13.

Orringer, Jay, et al., "Management of Wounds in Patients with Complex Enterocutaneous Fistulas", Surgery, Gynecology & Obstetrics, Jul. 1987, V. 165, pp. 79-80. NPL-323.

Lohman, R., et al., "Discussion: Vacuum Assisted Closure: Microdeformations of Wounds and Cell Proliferation", Plastic and Reconstructive Surgery, Oct. 2004, pp. 1097-1098. NPL-257.

Defranzo, A.J., et al., "109: Use of Sub-Atmospheric Pressure for Treatment of Gunshot Injuries", Plastic Surgical Forum, V. XXIII, Los Angeles, CA, Oct. 14-18, 2000, pp. 180-181. WFU-05.

Marks, M., et al., "Management of Complex Soft Tissue Defects in Pediatric Patients Using the V.A.C. Wound Closure", Plastic Surgical Forum, V. XXI, Boston, MA, Oct. 3-7, 1998, pp. 215-216. WFU-09.

Morykwas, M. and Argenta, L., "Use of Negative Pressure to Prevent Progression of Partial Thickness Burns", American Burn Association, V. 26, 26th Annual Meeting, Apr. 20-23, 1994, Orlando, Florida, pp. 157. WFU-14.

Morykwas, M. and Argenta, L., "Vacuum Assisted Closure (VAC Therapy) for Secondary Closure of Dehisced and Infected Wounds", Wound Repair and Regeneration, Jul.-Sep. 1995, pp. 361. WFU-11.

Morykwas, M. and Argenta, L., "Treatment of Burned Extremities Using Vacuum Therapy (The V.A.C.)", Wound Repair and Regeneration, V. 3, N. 3, Jul.-Sep. 1995, pp. 367. WFU-15.

Webb, L. and Morykwas, M., et al., "The Use of Vacuum-Assisted Closure in Composite Wound Management", The Third Riva Congress, Current Perspectives in Fracture Management and Orthopaedic Reconstruction, May 10-14, 2000, Italy, pp. 137. WFU-20.

Morykwas, M. and Webb, L., "Sub-Atmospheric Pressure for the Treatment of Lower Extremity Wounds", The Third Riva Congress, Current Perspectives in Fracture Management and Orthopaedic Reconstruction, May 10-14, 2000, Italy, pp. 135-136. WFU-18.

Argenta, L., et al., "Use of V.A.C. For Treatment of Dehisced Sternal Incisions", Plastic Surgical Forum, V. XXIII, Los Angeles, CA, Oct. 14-18, 2000, pp. 172-174. WFU-06.

Morykwas, M., et al., "Isolated Muscle Flap Survival with Complete Venous Occlusion: Varying Delay in External Application of Sub-atmospheric Pressure", Plastic Surgical Forum, V. XXI, Boston, MA, Oct. 3-7, 1998, pp. 237. WFU-16.

Morykwas, M., et al., "Vacuum-Assisted Closure: A New Method for Wound Control and Treatment: Animal Studies and Basic Foundation", Annals of Plastic Surgery, V. 38, N. 6, Jun. 1997, pp. 553-562. WFU-29.

Argenta, L. and Morykwas, M., "Vacuum-Assisted Closure: A New Method for Wound Control and Treatment: Clinical Experience", Annals of Plastic Surgery, V. 38, N.6, Jun. 1997, pp. 563-577. WFU-31.

Morykwas, M. and Argenta, L., "V.A.C. Experience and Difficult Wounds", des Journees Regionales des Plaies et Cicatrisations, Sep. 22-23, 1997, pp. 76-90. WFU-01.

Genecov, D., et al., "A Controlled Subatmospheric Pressure Dressing Increases the Rate of Skin Graft Donor Site Reepithelialization", Annals of Plastic Surgery, V. 40, N. 3, Mar. 1998, 219-225. WFU-28.

Morykwas, M. and Argenta, L., "Techniques in Use of V.A.C.™ Treatment", ACA-Acta Chir. Austriaca, Supplement Nr. 150, 1998, pp. 3-4 of 2-28. WFU-02.

Morykwas, M. and Argenta, L., "Use of the V.A.C.™ for Treatment of a Traumatic Left Hip Disarticulation",ACA-Acta Chir. Austriaca, Supplement Nr. 150, 1998, pp. 24-25 and cover sheet. WFU-12.

Morykwas, M., et al., "Use of Subatmosperic Pressure to Prevent Progression of PartialpThickness Burns in a Swine Model", Journal of Burn Care & Rehabilitation, Jan./Feb. 1999, pp. 15-21. WFU-03.

Banwell, P., et al., "Application of Topical Sub-Atmospheric Pressure Modulates Inflammatory Cell Extravasation in Experimental Partial Thickness Burns", Wound Repair and Regeneration, Jul./Aug. 1999, V. 7, N. 4, pp. A286-287. WFU-08.

Morykwas, M., et al., "Use of Subatomospheric Pressure to Prevent Doxorubicin Extravasation Ulcers in a Swine Model", Journal of Surgical Oncology, 1999; 72:14-17. WFU-33.

Banwell, P., et al., "Dermal Perfusion in Experimental Partial Thickness Burns: The Effect of Topical Subatmospheric Pressure", Jan./Feb. 2000, V. 21, N. 1, Part 2, Burn Care & Rehabilitation. WFU-07.

Mooney, J., et al., "Treatment of Soft Tissue Defects in Pediatric Patients Using the V.A.C.™ System", Clinical Orthopaedics and Related Research, No. 376, Jul. 2000, pp. 26-31. WFU-26.

Morykwas, M., et al., "The Effect of Externally Applied Subatmospheric Pressure on Serum Myoglobin Levels After a Prolonged Crused/Ischemia Injury", The Journal of TRAUMA Injury, Infection and Critical Care, Sep. 2002, V. 53, n. 3, pp. 537-540. WFU-19.

Molnar, J., et al., "Acceleration of Integra Incorporation in Complex Tissue Defects with Subatmospheric Pressure", Plastic and Reconstructive Surgery, Apr. 15, 2004, pp. 1339-1346. WFU-10.

Morykwas, M. and Argenta, L., "Nonsurgical Modalities to Enhance Healing and Care of Soft Tissue Wounds", Journal of the Southern Orthopaedic Association, V. 6, N. 4, 1997, pp. 279-288. WFU-04.

Schneider, A., et al., "A New and Reliable Method of Securing Skin Grafts to the Difficult Recipient Bed", Plastic and Reconstructive Surgery, Sep. 1998, pp. 1195-1198. WFU-30.

Rosser, C., et al., "A New Technique to Manage Perineal Wounds", Infections in Urology, Mar./Apr. 2000, V. 13, N.2, pp. 45-47 & 56. WFU-34.

Defranzo, A.J., et al., "The Use of Vacuum-Assisted Closure Therapy for the Treatment of Lower-Extremity Wounds with Exposed Bone", Plastic and Reconstructive Surgery, Oct. 2001, V. 108, N. 5, pp. 1184-1191. WFU-25.

Morykwas, M., "The Use of the V.A.C. Wound Treatment System for Acute and Subacute Wounds", Plaies & Cicatrices, Would Closure Healing, Apr. 21, 22 and 23, 1999. WFU-17.

Webb, L., et al., "Negative Pressure Wound Therapy in the Management of Orthopedic Wounds", Ostomy Wound Management, Apr. 2004, V. 50, Issue 4A (Suppl), pp. 26-27 and cover sheet. WFU-22.

Webb, L., et al., "Wound Management With Vacuum Therapy", English abstract from website printout and German article, http://www.ncbi_nlm_nih.gov/entrez/ctuery.fcgi?cmd=Retrieve&db=pubmed&dot=Abstra . . . , Dec. 2, 2004, 2 pages website printout, German article, Oct. 2001, pp. 918-926. WFU-23.

Webb, "New Techniques in Wound Management: Vacuum-Assisted Wound Closure", Journal of the American Academy of Orthopaedic Surgeons, V. 10, N. 5, Sep./Oct. 2002, pp. 303-311. WFU-21.

Morykwas, M. and Argenta, L., "Sub-Atmospheric Pressure Wound Treatment and Cultured Keratinocyte Allografts", Cultured Human Keratinocytes and Tissue Engineered Skin Substitutes, © 2001 Georg Thieme Verlag, pp. 343-346. WFU-27.

Molnar, J., et al., "Single-Stage Approach to Skin Grafting the Exposed Skull", Plastic and Reconstructive Surgery, Jan. 2000, V. 105, N. 1, 174-177. WFU-32.

Scherer, L., et al., "The Vacuum Assisted Closure Device: A Method of Securing Skin Grafts and Improving Graft Surival", Arch. Surg., V. 137, Aug. 2002, pp. 930-934. NPL-359.

Defranzo, A., et al., "Vacuum-Assisted Closure for the Treatment of Degloving Injuries", Plastic and Reconstructive Surgery, Dec. 1999, V. 104, N. 7, pp. 2145-2148. WFU-35.

Miller, P., et al., "Late Fascial Closure in Lieu of Ventral Hernia: The Next Step in Open Abdomen Management", The Journal of TRAUMA Injury, Infection and Critical Care, Nov. 2002, V. 53, N. 5, pp. 843849. NPL-288.

Betancourt, S., "A Method of Collecting the Effluent From Complicated Fistula of the Small Intestine", 1986, p. 375. NPL-045.

Dorland's Illustrated Medical Dictionary , Twenty-Fifth Edition, 1974, pp. 1112. NPL-120.

Hopf, H., et al., "Adjuncts to preparing wounds for closure Hyperbaric oxygen, growth factors, skin substitutes, negative pressure wound therapy (vacuum-assisted closure)", Foot Ankle Clin N Am 6, 2001, pp. 661-682. NPL-211.

Chariker-Jeter® Wound Drainage Kit, BlueSky Medical, 2 page advertisement with business card from Quality Medical Supply. NPL-077.

Chariker-Jeter® Wound Drainage Kit Instructions, Item #500.7777, BlueSky Medical, 2 pages. NPL-076.

Wooding-Scott® Wound Drainage Kit Contents, Item #500.8888, 1 page. NPL-445.

Montgomery, B., "Easy Dressing of Large, Draining Abdominal Wounds Using Moisture Vapor-Permeable Film", pp. 417-418, Techniques for Surgeons, Wiley Medical Publication, © 1985. NPL-297.

Davydov, Y., et al., "Pathogenic Mechanism of the Effect of Vacuum Therapy on the Course of the Wound Process", Jun. 1990, 16 pages of English Translation and abstract. DV13.

Borzov, M., et al., "Vacuum Therapy of Some Skin Diseases", Vestnik dermatologii venerologii, n. 8, Aug. 1965, pp. 50-56,(13 pages of English translation by R. McElroy and 1 sheet printout from PubMed). NPL-055.

Herrmann, L., et al., "The Pavaex (Passive Vascular Exercise) Treatment of Obliterative Arterial Diseases of the Extremeties", The Journal of Medicine, Dec. 1933, pp. 524-529. NPL-200.

Herrmann, L., et al., "Passive Vascular Exercises: Treatment of Peripheral Obliterative Arterial Diseases by Rhythmic Alternation of Environmental Pressure", Archives of Surgery, v. 29, n. 5, Nov. 1934, pp. 697-704. NPL-198.

Sturr, R., Evaluation of Treatment of Peripheral Vascular Disease by Alternating Positive and Negative Pressure, Philadelphia, Archives of Physical Therapy, Sep. 1938, pp. 539-543. NPL-392.

Balin, A., et al., "Oxygen Modulates Growth of Human Cells at Physiologic Partial Pressures", Laboratory for Investigative Dermatology, J. Exp. Med.©, the Rockefeller University Press, v. 160, Jul. 1984, pp. 152-166. NPL-029.

Saran Resins and Films, "Fresh Thinking" website printout, 6 pages, Jan. 20, 2004. NPL-354.

Bluesky Medical, "A Leader in Suction Technology—Wound Drainage Experts", printout of website, 55 pages, Apr. 8, 2003, www.blueskymedical.com. NPL-052.

Garcia-Rinaldi, R., et al., "Improving the Efficiency of Wound Drainage Catheters", v. 130, Sep. 1975, pp. 372-373. NPL-169.

Davydov, et al., "Would Healing Under the Conditions of Vacuum Draining", Khirurgiia (Mosk). 1992, (78): 21-6 (with English translation by Scientific Translation Services). DV14.

Davydov, et al., "Vacuum therapy in the treatment of acute suppurative diseases of soft tissue and suppurative wounds", Vestn. Khir, Sep. 1988 (with English translation by Ralph McElroy Co.). DV10.

Coyle, M., et al., "A Case Study: Positive Outcomes to Negative Pressure Wound Therapy—A collaborative assessment", Hospital of Saint Raphael, 1 page chart. NPL-102.

Nemoto, H., et al., "Stories From the Bedside: Purple Urine Bage Syndrome Development in Ileal Conduit", WCET, Journal 23(2), pp. 31-34. NPL-310.

Baker, B., "Negative-Pressure Therapy Looks Promising", Skin & Allergy News, Feb. 2000, p. 14. NPL-028.

McCallon, S., et al., "Vacuum-Assisted Closure versus Saline-Moistened Gauze in the Healing of Postoperative Diabetic Foot Wounds", Ostomy Wound Management, Aug. 2000, v.46, Issue 8.pp. 28-29, 31-32, 34. NPL-269.

Clinicians' Pocket Guide to Chronic Wound Repair, Wound Healing Publications, Second Edition, 01992, 106 pages. NPL-300.

Biblehimer, H., "Dealing with a Wound That Drains 1.5 Liters a Day", RN, Aug. 1986, pp. 21-23. NPL-046.

*Kinetic Concepts, Inc., et al., v. Bluesky Medical Corporation, et al.*, Civil Action No. SA-03-CA-0832-RF, U.S. District Court, W. Dist. of Texas San Antonio Div., Expert Report of Dennis P. Orgill, M.D., Ph.D., Feb. 18, 2005. BS-13.

*Kinetic Concepts, Inc., et al., v. Bluesky Medical Corporation, et al.*, Civil Action No. SA-03-CA-0832-RF, U.S. District Court, W. Dist. of Texas San Antonio Div., Rebuttal Expert Report of Wilson C. Haues, Ph.D. In Response to the Report of Michael H. Baniak (Feb. 18, 2005). BS-14.

*Kinetic Concepts, Inc., et al., v. Bluesky Medical Corporation, et al.*, Civil Action No. SA-03-CA-0832-RF, U.S. District Court, W. Dist. of Texas San Antonio Div., Expert Report of John T. Goolkasian in Rebuttal to Report of Michael H. Baniak (Feb. 18, 2005). BS-15.

*Kinetic Concepts, Inc., et al., v. Bluesky Medical Corporation, et al.*, Civil Action No. SA-03-CA-0832-RF, U.S. District Court, W. Dist. of Texas San Antonio Div., Rebuttal Expert Report of Louis C. Argenta, M.D. to Expert Report of Michael H. Baniak (Feb. 18, 2005). BS-16.

Banwell, P., et al., "Topical Negative Pressure TNP Focus Group Meeting", Proceedings, London, UK 2003, pp. 112-232. WFU-24.

*Kinetic Concepts, Inc., et al., v. Bluesky Medical Corporation, et al.*, Civil Action No. SA-03-CA-0832-RF, U.S. District Court, W. Dist. of Texas San Antonio Div., Ordering Adopting Stipulations of Parties Regarding Claim Term Construction dated May 12, 2005. BS-171.

*Kinetic Concepts, Inc., et al., v. Bluesky Medical Corporation, et al.*, Civil Action No. SA-03-CA-0832-RF, U.S. District Court, W. Dist. of Texas San Antonio Div., Order Construing Patent '643 Claim Terms dated Jun. 28, 2005. BS-172.

Opposition EP to 0,620,720, Patentee's Response to Grounds of Appeal Filed by Opponent, Paul Hartmann AG dated Apr. 25, 2005. EPOPWH1-16.

*Kinetic Concepts, Inc., et al., v. Bluesky Medical Corporation, et al.*, Civil Action No. SA-03-CA-0832-RF, U.S. District Court, W. Dist. of Texas San Antonio Div., Plaintiffs' Fourth Amended Complaint dated Jun. 30, 2005. BS-173.

*Kinetic Concepts, Inc., et al., v. Bluesky Medical Corporation, et al.*, Civil Action No. SA-03-CA-0832-RF, U.S. District Court, W. Dist. of Texas San Antonio Div., Kinetic Concepts, Inc.'s Supplemental Answers to Bluesky Medical Corporation's First Set of Interrogatories dated Jul. 6, 2005. BS-174.

*Kinetic Concepts, Inc., et al., v. Bluesky Medical Corporation, et al.*, Civil Action No. SA-03-CA-0832-RF, U.S. District Court, W. Dist. of Texas San Antonio Div., KCI Licensing, Inc.'s Supplemental Answers to Medela, Inc.'s First Set of Interrogatories dated Jul. 6, 2005. BS-175.

*Kinetic Concepts, Inc., et al., v. Bluesky Medical Corporation, et al.*, Civil Action No. SA-03-CA-0832-RF, U.S. District Court, W. Dist. of Texas San Antonio Div., Wake Forest University Health Sciences' Supplemental Answers to Medela Inc.'s First Set of Interrogatories dated Jul. 6, 2005. BS-176.

*Kinetic Concepts, Inc., et al., v. Bluesky Medical Corporation, et al.*, Civil Action No. SA-03-CA-0832-RF, U.S. District Court, W. Dist. of Texas San Antonio Div., Amended Answer to Third Amended Complaint, Additional Defenses, Second Amended Counterclaims and Jury Demand of Medela, Inc. dated Apr. 29, 2005. BS-177.

*Kinetic Concepts, Inc., et al., v. Bluesky Medical Corporation, et al.*, Civil Action No. SA-03-CA-0832-RF, U.S. District Court, W. Dist. of Texas San Antonio Div., Answer to Third Amended Complaint, Additional Defenses, Amended Counterclaims and Jury Demand of Defendant Medela AG dated Feb. 11, 2005. BS-178.

Thomas, S., et al., "Comparative Review of the Properties of Six Semipermeable Film Dressings", The Pharmaceutical Journal, Jun. 18, 1988, pp. 785-789. NPL-402.

Baker, B., "Abundance of Web Sites on Wound Care Management", Family Practice News, Mar. 1, 2000, pp. 52. NPL-027.

Cosker, T., et al., "Choice of Dressing Has a Major Impact on Blistering and Healing Outcomes in Orthopaedic Patients", Journal of Wound Care, Vo. 14, No. 1, Jan. 2005, pp. 27-29. NPL-101.

Townsend, P.L.G., "The Quest for a Cheap and Painless Donor-Site Dressing", Burns, 2, pp. 82-85 (Jan. 1976). NPL-404.

Langworthy, M., et al., "Treatment of the Mangled Lower Extremity After a Terrorist Blast Injury", Clinical Orthopaedics and Related Research, No. 422, pp. 88-96 (May 2004). NPL-251.

Park, G.B., et al., "The Design and Evaluation of a Burn Wound Covering", Supplied by the British Library—"The Word's Knowledge", pp. 11-15 (1978). NPL-327.

ACU-derm® Transparent Moisture Vapor Permeable Polyurethane Dressing, pp. 1-13 and cover sheet. NPL-003.

3M Ioban 2, Breathability, Conformability and Strength, Breathability—Moisture Vapor Transmission Rate and Conformability and Strength—Tensile Strength, Elongation and Fn Modulus Test (1 page). NPL-001.

smith&nephew website printout, Would Management, FAQs. NPL-380.

"Moist Wound Dressings" from Physicians Instruction Book for Moist Wound Healing. NPL-295.

*Kinetic Concepts, Inc., et al., v. Bluesky Medical Corporation, et al.*, Civil Action No. SA-03-CA-0832-RF, U.S. District Court, W. Dist. of Texas San Antonio Div., Deposition transcript with Exhibits of Mark Chariker dated May 6, 2005. BS-76.

*Kinetic Concepts, Inc., et al., v. Bluesky Medical Corporation, et al.*, Civil Action No. SA-03-CA-0832-RF, U.S. District Court, W. Dist. of Texas San Antonio Div., Deposition transcript with Exhibits of David S. Zamierowski dated Feb. 15, 2005. BS-77.

*Kinetic Concepts, Inc., et al., v. Bluesky Medical Corporation, et al.*, Civil Action No. SA-03-CA-0832-RF, U.S. District Court, W. Dist. of Texas San Antonio Div., Expert Report with Exhibits of Harriet W. Hopf dated May 10, 2005, along with Supplemental Expert Report with Exhibits dated May 25, 2005. BS-17.

*Kinetic Concepts, Inc., et al., v. Bluesky Medical Corporation, et al.*, Civil Action No. SA-03-CA-0832-RF, U.S. District Court, W. Dist. of Texas San Antonio Div., Expert Report with Exhibits of Susan Mendez-Eastman dated Jan. 7, 2004. BS-18.

*Kinetic Concepts, Inc., et al., v. Bluesky Medical Corporation, et al.*, Civil Action No. SA-03-CA-0832-RF, U.S. District Court, W. Dist. of Texas San Antonio Div., Expert Report with Exhibits of Jose Diaz dated Nov. 26, 2004. BS-19.

*Kinetic Concepts, Inc., et al., v. Bluesky Medical Corporation, et al.*, Civil Action No. SA-03-CA-0832-RF, U.S. District Court, W. Dist. of Texas San Antonio Div., Expert Report with Exhibits of Jeffrey Niezgoda dated Nov. 23, 2004. BS-20.

*Kinetic Concepts, Inc., et al., v. Bluesky Medical Corporation, et al.*, Civil Action No. SA-03-CA-0832-RF, U.S. District Court, W. Dist. of Texas San Antonio Div., Expert Report with Exhibits of Kathleen Satterfield dated Nov. 29, 2004. BS-21.

*Kinetic Concepts, Inc., et al., v. Bluesky Medical Corporation, et al.*, Civil Action No. SA-03-CA-0832-RF, U.S. District Court, W. Dist. of Texas San Antonio Div., Exhibits 281-288 of previously submitted Transcription of Deposition of Michael John Morykwas, PhD. dated Jan. 13, 2005. BS-78.

Svedman, P., "A dressing allowing continuous treatment of a biosurface," IRCS Medical Science: Biomedical Technology; Clinical Medicine; Surgery and Transplantation, 7:221 (1979). (Exhibit D-407). NPL-387.

Johnson, F., "An Improved Technique for Skin Graft Placement Using a Suction Drain," Surgery, Gynecology & Obstetrics, p. 585-586, Dec. 1984, (Exhibit D132). NPL-226.

Davydov, Y., et al., "Bacteriological and Cytological Assessment of Vacuum Therapy of Purulent Wounds," Vestn. Khir., 48-52, English translation by IRC, (Oct. 1988). (Exhibit D-290). NPL-616.

Davydov, Y., et al., "Vacuum Therapy in the Treatment of Purulent Lactation Mastitis," Vestn. Khir. p. 66-70, English translation by IRC, (Sep. 1986), (Exhibit D-292). NPL-617.

Meyer, W., et al., "Bier's Hyperemic Treatment," W.B. Saunders & Co., 1908 (Exhibit D246) NPL-283.

Chariker/Jeter/Tintle Slides "Closed Wound Suction" by Dr. Mark Chariker et al., 41 sheets, pp. 1-10, 19, 55-84 (D-041) (allegedly dated 1985 and 1986) NPL-079.
Jeter, K., List of publications, 4 sheets, (D-161) NPL-225.
Chariker/Jeter, Spartanburg General Hospital Progress Notes, dated 1986, 25 pages, (Exhibit D-158) NPL-080.
Spahn/Hamaker slide entitled "Poor man's irrigation/vacuum dressing used since 1970's," (Exhibit D-135) NPL-382.
*KCI v. BlueSky*, Final Jury Instructions, 84 pages, delivered to jury Jul. 14, 2006. BS-207.
*KCI v. BlueSky*, Trial Transcript, dated Jun. 1, 2006 BS-99.
*KCI v. BlueSky*, Trial Transcript of Argenta, dated Jun. 2, 2006 BS-100.
*KCI v. BlueSky*, Trial Transcript of Argenta/Morykwas, dated Jun. 5, 2006 BS-101.
*KCI v. BlueSky*, Trial Transcript of Morykwas/Leininger/Weston, dated Jun. 6, 2006 BS-102.
*KCI v. BlueSky*, Trial Transcript of Weston, dated Jun. 7, 2006 BS-103.
*KCI v. BlueSky*, Trial Transcript of Weston, dated Jun. 8, 2006 BS-104.
*KCI v. BlueSky*, Trial Transcript of Niezgoda, dated Jun. 9, 2006 BS-105.
*KCI v. BlueSky*, Trial Transcript of Miller/Anderson/Ware, dated Jun. 19, 2006 BS-106.
*KCI v. BlueSky*, Trial Transcript of Ware/Resietter/Condor/Malackowski, dated Jun. 20, 2006 BS-107.
*KCI v. BlueSky*, Trial Transcript of Malackowski/Dairman/LeszkiewiczlBanes/John, dated Jun. 21, 2006 BS-108.
*KCI v. BlueSky*, Trial Transcript of Johnson/Quackenbush, dated Jun. 29, 2006 BS-109.
*KCI v. BlueSky*, Trial Transcript of Quackenbush/Laurel, dated Jun. 30, 2006 BS-110.
*KCI v. BlueSky*, Trial Transcript for Escobedo/Satterfield/Chariker, dated Jul. 5, 2006 BS-111.
*KCI v. BlueSky*, Trial Transcript for Chariker/Hamaker/Spahn/Jeter/Hopf, dated Jul. 6, 2006 BS-112.
*KCI v. BlueSky*, Trial Transcript for Hopf/Lockhart, dated Jul. 7, 2006 BS-113.
*KCI v. BlueSky*, Trial Transcript for Hopf, dated Jul. 10, 2006 BS-114.
*KCI v. BlueSky*, Trial Transcript for Pizziconi/Orgill, dated Jul. 11, 2006 BS-115.
*KCI v. BlueSky*, Trial Transcript for Orgill/Bridi/McGregor/Girolami/Taylor, dated Jul. 12, 2006 BS-116.
*KCI v. BlueSky*, Trial Transcript for Campbell, dated Jul. 13, 2006 BS-117.
*KCI v. BlueSky*, Trial Transcript dated Jul. 14, 2006 BS-118.
*KCI v. BlueSky*, Trial Transcript dated Jul. 17, 2006 BS-119.
*KCI v. BlueSky*: BlueSky Medical Group Inc. and Richard Weston's motion to exclude certain expert testimony dated Apr. 21, 2006. BS-208.
*KCI v. BlueSky*: Medela's Motion to exclude proposed trial testimony of plaintiffs experts Louis C. Argenta, Dennis P. Orgill and Wilson C. Hayes, dated Apr. 21, 2006. BS-209.
*KCI v. BlueSky*: Plaintiffs motion to exclude opinions of Vincent Pizziconi dated Apr. 21, 2006. BS-210.
*KCI v. BlueSky*: Plaintiffs motion to exclude certain opinions of Michael O'Neil dated Apr. 21, 2006. BS-211.
*KCI v. BlueSky*: Medela's response to plaintiffs motion to exclude opinions of Harriet Hopf with Exhibits dated Apr. 28, 2006. BS-212.
*KCI v. BlueSky*: Medela's response to plaintiffs motion to exclude opinions of Michael O'Neil and motion to exclude opinions of John T. Goolkasian with Exhibits dated Apr. 28, 2006. BS-213.
*KCI v. BlueSky*: Medela's response to plaintiffs motion to exclude opinions of James Spahn dated Apr. 28,2006. BS-214.
*KCI v. BlueSky*: Plaintiffs response to Medela's motion to exclude proposed trial testimony of Louis C. Argenta, Dennis P. Orgill, and Wilson C. Hayes, dated May 1, 2006. BS-215.
*KCI v. BlueSky*: Medela's Renewed Motion for Judgment as a Matter of Law, or, in the alternative, a New Trial, on Patent Invalidity, dated Sep. 13, 2006. BS-216.
*KCI v. BlueSky*: Medela's Motion for a New Trial on Unenforceability, dated Sep. 13, 2006. BS-217.
Claim Chart of Asserted Claims of U.S. Patent 5,636,643 to Argenta, 3 pages. BS-218.
Claim Invalidity Analysis of U.S. Patent 5,636,643 to Argenta, et al., 34 pages, Mar. 2004. BS-219.
*KCI v. BlueSky*: Letter dated Dec. 9, 2005 from the Honorable Royal Ferguson to attorneys in *KCI v. BlueSky* regarding claim construction. BS-220.
*KCI v. BlueSky*, Letter from Valery Gilevich, M.D. To Kirt S. O'Neill, dated May 28, 2006 concerning review of English translation of Russian article. BS-221.
*KCI v. BlueSky*, Second Amended Order Construing Patent '643 and '081 Claim Terms dated Jun. 29, 2006. BS-222.
*KCI v. BlueSky*, Expert Report of Mark Chariker, with Exhibits, dated Jan. 7, 2005. BS-23.
*KCI v. BlueSky*, Supplemental Expert Report of Mark Chariker, M.D., with Exhibits, dated Dec. 19, 2005. BS-24.
*KCI v. BlueSky*, Supplemental Expert Report of Harriet Hopf, with Exhibits, dated Nov. 18, 2005. BS-25.
*KCI v. BlueSky*, Amended Expert Report of Harriet W. Hopf, M.D. on New Claims, with Exhibits, dated Feb. 10, 2006 . BS-26.
*KCI v. BlueSky*, Expert Report of Harriet W. Hopf, M.D. Responsive to Plaintiffs Asserted Claims for Relief, with Exhibits, dated Feb. 10, 2006. BS-27.
*KCI v. BlueSky*, Supplemental Expert Report of Harriet W. Hopf, M.D. with Exhibits, dated Jun. 23, 2006. BS-28.
*KCI v. BlueSky*, Report of Katherine F. Jeter, with Exhibits, dated Nov. 28, 2004. BS-11.
*KCI v. BlueSky*, Supplemental Expert Report of Michael O'Neil, dated Feb. 22, 2006. BS-31.
*KCI v. BlueSky*, Rebuttal Expert Report of Harriet W. Hopf, M.D. with Exhibits, dated Mar. 11, 2006. BS-32.
*KCI v. BlueSky*, Rebuttal Report to Plaintiffs' Rebuttal Expert Report by Michael O'Neil, dated Mar. 12, 2006. BS-33.
*KCI v. BlueSky*, Attachments to Expert Report of Michael A. O'Neil . BS-34.
*KCI v. BlueSky*, Expert Report of Vincent Pizziconi, with Exhibits, dated Dec. 31, 2005. BS-35.
*KCI v. BlueSky*, Amended Expert Report of Vincent B. Pizziconi, Ph.D., with Exhibits, dated Feb. 6, 2006. BS-36.
*KCI v. BlueSky*, Expert report of Vincent B. Pizziconi, Ph.D. responsive to plaintiffs asserted claims for relief, with exhibits, dated Feb. 14, 2006. BS-37.
*KCI v. BlueSky*: Amended expert report of Vincent B. Pizziconi, Ph.D. responsive to plaintiffs asserted claims for relief, with exhibits, dated Feb. 16, 2006. BS-38.
*KCI v. BlueSky*, Rebuttal Expert Report of Vincent B. Pizziconi, Ph.D., with Exhibits, dated Mar. 12, 2006. BS-39.
*KCI v. BlueSky*, Supplemental Expert Report of Vincent B. Pizziconi, Ph.D. with Exhibits, dated Jun. 23, 2006. BS-40.
*KCI v. BlueSky*, Supplemental expert report of Lydia Razran Stone, Ph.D., with exhibits, dated Mar. 8, 2006. BS-41.
*KCI v. BlueSky*, Expert Report of Lydia Razran Stone, Ph.D., with Exhibits, dated Dec. 29, 2005. BS-42.
*KCI v. BlueSky*, Expert Report of Louis C. Argenta in Response to Report of Katherine Jeter, with Exhibits, dated Jan. 5, 2005. BS-43.
*KCI v. BlueSky*, Responsive Expert Report of Louis C. Argenta to Reports of Hopf, O'Neil, Pizziconi & Chariker, dated Feb. 27, 2006. BS-44.
*KCI v. BlueSky*, Responsive Expert Report of Louis C. Argenta to Supplemental Expert Report of O'Neil, dated Mar. 13, 2006. BS-45.
*KCI v. BlueSky*, Rebuttal Report of Louis C. Argenta in Response to James Spahn, Mark Chariker & Thomas Hunt. BS-46.
*KCI v. BlueSky*, Responsive Expert Report of Louis C. Argenta, M.D. to Expert Supplemental Reports of Hopf and with Pizziconi, with Exhibits, dated Jul. 8, 2006. BS-47.
*KCI v. BlueSky*, Responsive Expert Report of Valery Gilevich, M.D. to Expert Report of Lydia Razran Stone, Ph.D. BS-48.
*KCI v. BlueSky*, Expert Report of Valery Gilevich, dated Dec. 14, 2004, with Exhibits, (Exhibit P-47). BS-49.
*KCI v. BlueSky*: Rebuttal expert report of John T. Goolkasian, dated Feb. 22, 2006. BS-50.

*KCI v. BlueSky*, Supplemental Rebuttal Expert Report of John T. Goolkasian, with Exhibits, dated Mar. 10, 2006. BS-51.
*KCI v. BlueSky*, Report of Wilson C. Hayes, PhD, with Exhibits, dated Nov. 29, 2004. BS-12.
*KCI v. BlueSky*, Expert Report of Wilson Hayes in Response to Reports of James Spahn and Mark Chariker, with Exhibits, dated Jan. 31, 2005. BS-53.
*KCI v. BlueSky*, Expert Report of Wilson Hayes in Response to Report of Katherine Jeter, with Exhibits, dated Jan. 7, 2005. BS-54.
*KCI v. BlueSky*, Supplemental Expert Report of Wilson C. Hayes, Ph.D. Concerning Infringement of Newly Asserted Claims of U.S. Patent Nos. 5,636,643 and 5,645,081, with Exhibits, dated Dec. 19, 2005. BS-55.
*KCI v. BlueSky*, Responsive Expert Report of Wilson Hayes in Response to Hopf, Chariker, Pizziconi, and O'Neil Regarding Patent Validity, with Exhibits, dated Feb. 27, 2006. BS-56.
*KCI v. BlueSky*, Rebuttal Expert Report of Wilson C. Hayes, Ph.D. in Response to the Reports of Harriet Hopf and Vincent Pizziconi Regarding Plaintiffs' Asserted Claims for Relief, with Exhibits, (Mar. 7, 2006). BS-57.
*KCI v. BlueSky*, Expert Report of Jeffery Niezgoda in Response to Katherine Jeter, dated Jan. 7, 2005. BS-58.
*KCI v. BlueSky*, Expert Report of Jeffery Niezgoda in Response to James Spahn, Thomas Hunt & Mark Chariker, dated Jan. 31, 2005. BS-59.
*KCI v. BlueSky*, Supplement to Expert Report of Jeffery Niezgoda, with Exhibits, dated Jan. 4, 2006. BS-60.
*KCI v. BlueSky*, Expert Report of Dennis P. Orgill, M.D., Ph.D., with Exhibits, dated Feb. 20, 2006. BS-61.
*KCI v. BlueSky*, Rebuttal Expert Report of Dennis Orgill to Amended Expert Reports of Harriet Hopf and Vincent Pizziconi, with Exhibits, dated Mar. 13, 2006. BS-62.
*KCI v. BlueSky*, Supplemental Expert Report of Dennis P. Orgill, M.D., Ph.D., with Exhibits, dated Jul. 6, 2006. BS-63.
Alexander, J.W., et al., "Clinical evaluation of epigard, a new synthetic substitute for homograft and heterograft skin," J. of Trauma, 13:374-383, (1973) NPL-010.
Anon., "Standard Test Methods for Water Vapor Transmission of Materials," ASTM, Designation: E 96/E 96M-05, Published Jun. 2005, 11 sheets, (Exhibit D-184) NPL-017.
Bertone, A.L., et al., "Management of Exuberant Granulation Tissue," Veterinary Clinic of North America—Equine Practice, vol. 3, pp. 551-562, (1989). NPL-043.
Byers, R.M., "Clinical effects of closed suction drainage on wound healing in patients with head and neck cancer," Arch. Otolaryngol., vol. 108:723-6, (Nov. 1982). NPL-066.
Cesany, P., "Suction in the Treatment of Torpid Ulcerations," Rozhledy v chirurgii, 48-9, MINC022894-MINC022898, cover sheet and pp. 406-409 English abstract on p. 409 (1 sheet printout from PubMed) (Sep. 1969). NPL-072.
Chinn, S.D., "Closed wound suction drainage," J. Foot Surg., vol. 24: 76-81, (Jan.-Feb. 1985). NPL-083.
Davydov, Y., et al., "Bacteriological and Cytological Assessment of Vacuum Therapy of Purulent Wounds," Vestn. Khir., cover sheet and pp. 48-52, in Russian, English abstract provided on p. 52, (1988), (Exhibit D-172). DV3.
Davydov, Y., et al., "Vacuum Therapy in the Treatment of Purulent Lactation Mastitis," Vestn. Khir. Cover sheet and pp. 66-70, in Russian, English abstract provided on p. 70, (1986), (Exhibit D-173). DV6.
Davydov, Y.A., et al., "Vacuum Therapy in Treatment of Acute Purulent Diseases of Soft Tissues and Purulent Wounds," Vestnik Khirurgili (Surgeon's Herald), Medicine Publishers 1986, 5 sheets, (Exhibit P-528) DV11.
Email dated Jan. 14, 2002 with attachments, including "Report of Meeting with DG Consulting" dated Jan. 10, 2002, 5 sheets, (Exhibit D-157). NPL-137.
Westaby, S., "Treatment of purulent wounds and fistulae with an adhesive wound irrigation device," Annals of the Royal College of Surgeons, vol. 63: 353-6 (1981). NPL-145.
Fox, R., "A rapid screen for drug abuse," The Pharmaceutical Journal, 789, (1988) NPL-165.

Hartz, R.R., et al., "Healing of the Perineal Wound," Arch. Surg., vol. 115, 471-474, (1980), (Exhibit D-395). NPL-196.
Letter dated Jan. 25, 2002 from Charles C. Valauskas to Mr. Richard Weston Regarding: Argenta "Wound Treatment" Patent Evaluation, 15 pages, (Exhibit D-388). NPL-254.
Letter to European Patent Office regarding Observations by a third party pursuant to Art. 115 EPC, 4 sheets, dated Mar. 6, 2006. EPOP1WH1-26.
Letter to Mr. Urs Tanner from Michael Baniak dated Aug. 23, 2004 re: Updated Opinion of Non-infringement and Invalidity of Zamierowski U.S. Patent 4,969,880 and Argenta U.S. Patent 5,636,643 (Exhibit D-140). NPL-255.
Mizuno, K., "Suctioning Sponge," Arch. Opthalmol., vol. 101:294, (Feb. 1983). NPL-294.
Morykwas, Laboratory Notebook pages and charts; 38 pages (Exhibit D-46) dated prior to Mar. 1993 WFU-45.
Morykwas, Laboratory notebook pages and charts, 16 sheets, (Exhibit D-286) dated prior to Mar. 1993 WFU-46.
Morykwas, Laboratory notebook pages and charts, 17 sheets, (Exhibit D-233) dated prior to Nov. 1991 WFU-47.
Morykwas, Laboratory notebook pages of charts, Aug. 29 and Dec. 19, 3 sheets, (Exhibit P-664) dated prior to Nov. 1991 WFU-48.
Nikolov, A., "Method of treatment of postphlebitic and varicose trophic ulcers on the lower extremities by vacuum [Vacuum treatment method in postphlebitic and varicose trophic ulcers of the lower extremities]," Khirurgiia, pp. 368-374, (English abstract on p. 371 and 1 sheet printout from PubMed) (1981) NPL-314.
O'Leary, P., ed., et al., "Techniques for Surgeons," John Wiley & Sons, 3 cover sheets and pp. 417-418, article by Barbara Ann Montgomery, "142: Easy Dressing of Large, Draining Abdominal Wounds Using Moisture Vapor-Permeable Film," (1985). NPL-297.
Opposition EP to 0620720, Communication of Opponent Hartman (Brief in Reply to Patentee's Brief Oct. 15, 1999) dated Mar. 8, 2000 (and English translation). EPOPWH1-04.
Opposition EP to 0620720, Communication of Opponent Hartman (Opening Brief) dated Dec. 16, 1998). EPOPWH1-01.
Opposition EP to 0620720, Communication of Opponent Hartman dated Jul. 19, 2004. EPOPWH1-14.
Opposition EP to 0620720, Communication of Opponent Hartman dated Sep. 20, 2004 with Eng. Translation. EPOPWH1-15.
Opposition EP to 0620720, Communication of Opponent Mondomed Dec. 17, 1998. EPOPWH1-02.
Opposition EP to 0620720, Communication of Patentee (Response Brief) dated Oct. 15, 1999. EPOPWH1-03.
Opposition EP to 0620720, Patentee's Grounds of Appeal, dated Sep. 29, 2004, with English translation. EPOPWH1-18.
Opposition EP to 0620720, Preliminary Opinion of Opposition Division dated Aug. 11, 2003 (5 pages), Summons to Oral Proceedings Pursuant to Rule 71(1) EPC Dated Aug. 12, 2003, (6 pages). EPOPWH1-08.
Photographs of wound coverings, 16 sheets, (Exhibit D-240) (allegedly dated 1989). NPL-331.
Slides and photographs, 19 sheets, (Exhibit D-152) (allegedly dated 1987). NPL-376.
Slides, drawings, photographs and presentation slides, 20 sheets, (Exhibit D-151) (allegedly dated 1987). NPL-377.
Smith, S.R., "Surgical drainage," Br. J. Hosp. Med., pp. 308-315, (Jun. 1985). NPL-379.
Svedman, "A dressing system providing fluid supply and suction drainage used for continuous or intermittent irrigation," Ann. Plast. Surg., vol. 17, 9 pages, (Aug. 1986). NPL-389.
Svedman, "Irrigation treatment in split thickness skin grafting of intractable leg ulcers," Scand. J. Plast. Reconstr. Surg., vol. 19:211-213, (1985). NPL-390.
Svedman, "A dressing allowing continuous treatment of a biosurface," IRCS Medical Science: Biomedical Technology; Clinical Medicine; Surgery and Transplantation, 7:221 (1979), with annotations. NPL-388.
Viljanto, J., "Eine neue Methode zur Behandlung offener Wundflachen," ("A new method for treatment of open wounds") Annales Chirugine et Gynaecologiae Fenniae, 60:94-100, (English abstract on first page and 1 sheet printout from PubMed) (1972). NPL-421.

Yusupov, Yu. N., et al., 5 sheets of English translation of "Active Drainage of Wounds", Vestnik khirurgii imeni I.I. Grekova 1987, 138(4), 42-46 (1987), also attached are 3 pages of English translation by BlueSky publishing entitled "Active Wound Drainage" by Usupov and Yupifanov, Vestisik Khirugii, April 42-46 (1987) (1 sheet printout from PubMed). NPL-452.

Morykwas, Laboratory Notebook pages and charts; (D-46) dated prior to Nov. 1991 WFU-49.

Morykwas, Laboratory Notebook pages and charts; (D-286) dated prior to Nov. 1991 WFU-50.

Leaper, D.J., "The Wound Healing Process," Advances in Wound Management, T.D. Turner, et al., eds., pp. 7-16, New York: John Wiley and Sons, (1986) NPL-252.

Moloney, G., "Apposition and Drainage of Large Skin Flaps by Suction," The Australian and New Zealand Journal of Surgery, 26(3):173-179, (1957). NPL-296.

Turner, T.D., "Semipermeable Films as Wound Dressings", Schweiz Rundsch Med. Prax., 73(30-31): 950-952, (1984). NPL-407.

Taylor, V., "Meeting the Challenge of Fistulas & Draining Wounds", Nursing80, Jun. 1980, pp. 45-51. NPL-398.

McFarlane, R., "The use of Continuous Suction Under Skin Flaps", British Journal of Plastic Surgery, vol. 11, 1958, pp. 77-86. NPL-271.

Davydov, Y.A., et al., "Bacteriological and cytological assessment of vacuum therapy of purulent wounds," Vestnik Khirurgii imeni I.I. Grekova, (7 sheets of translation, pp. 48-52 of Russian text and English abstract on p. 52); 141 (10):48-52 (Oct. 1988). DV4.

Davydov, Y.A., et al., "Vacuum therapy in the treatment of purulent lactation mastitis", Vestnik Khirurgii imeni I.I. Grekova, (8 sheets of English translation, pp. 66-70 of Russian text, and English abstract on p. 70); 137(11):66-70, (Nov. 1986). DV7.

Davydov, Y.A., et al., "Vacuum therapy in the treatment of acute purulent diseases of soft tissues and purulent wounds", Vestn. Khir. Im. I.I. Grek., (4 sheets of Translation, 4 sheets of Russian text and English abstract on p. 46); 141(9):43-46 (Sep. 1988). DV9.

KCI v. BlueSky, Deposition of Penny Campbell with Exhibits dated Jan. 17, 2005. BS-80.

KCI v. BlueSky, Transcript of Deposition of Mark Chariker, M.D., with Exhibits, dated Apr. 5, 2006. BS-81.

KCI v. BlueSky, Transcript of Deposition of Harriet W. Hopf, M.D., with Exhibits, dated Jul. 4, 2006. BS-82.

KCI v. BlueSky, Deposition transcript with Exhibits of Thomas K. Hunt dated Apr. 21, 2005. BS-83.

KCI v. BlueSky, Transcript of Deposition of Donna Goudberg Lockhart, with Exhibits, dated Jul. 7, 2006. BS-84.

KCI v. BlueSky, Transcript of Deposition of Marie Louise Lachute McGregor, dated Jul. 11, 2006. BS-85.

KCI v. BlueSky, Transcript of Deposition of Michael A. O'Neil, with Exhibits, dated Apr. 6, 2006. BS-86.

KCI v. BlueSky, Transcript of Deposition of Vincent B. Pizziconi, Ph.D., with Exhibits, dated Apr. 7, 2006. BS-87.

KCI v. BlueSky, Transcript of Deposition of David Tumey, with Exhibits, dated Jun. 15, 2006. BS-88.

KCI v. BlueSky, Transcript of Deposition of Tianning Xu, with Exhibits, dated Apr. 27, 2006. BS-89.

KCI v. BlueSky, Videotaped Deposition of Louis C. Argenta, M.D., with Exhibits, Winston-Salem, North Carolina, Friday, Mar. 17, 2006. BS-90.

KCI v. BlueSky, Transcript of Deposition of John T. Goolkasian, Esq., with Exhibits, dated Apr. 19, 2006. BS-91.

KCI v. BlueSky, Transcript of Deposition of Wilson C. Hayes, Ph.D., with Exhibits, dated Mar. 29, 2006. BS-92.

KCI v. BlueSky, Transcript of Deposition of Cynthia Ann Miller, with Exhibits, dated May 24, 2006. BS-93.

KCI v. BlueSky, Transcript of Deposition of Jeffrey A. Niezgoda, M.D., dated Jun. 8, 2006. BS-95.

KCI v. BlueSky, Deposition of Orgill with Exhibits dated Mar. 22, 2006. BS-96.

KCI v. BlueSky, Deposition of Donald R. Piper, Jr., dated Dec. 1, 2005. BS-97.

KCI v. BlueSky, Transcript of Deposition of Kathleen Satterfield, D.P.M., with Exhibits, dated Apr. 3, 2006. BS-98.

Opposition to EP 0,620,720—Summons to attend oral proceedings pursuant to Rule 71(1) EPC, Annex to communication, (9 sheets) both dated (Feb. 13, 2002) and Communication from Opponent Mondomed N.V. (2 sheets) (dated Feb. 15, 2002). EPOPWH1-21.

Opposition to EP 0,620,720—Minutes of the Oral Proceedings, Documents for the Maintenance of the Patent as Amended, Annex to the Communication (30 sheets) (dated Dec. 30, 2003). EPOPWH1-22.

Opposition to EP 0,620,720—Communication of Notices of Opposition (Rule 57(1) EPC) dated (Feb. 8, 1999) (1 sheet), Notice of Opposition by Mondomed N.V., (4 sheets) and 8 sheets of Facts and Arguments presented in support of opposition (dated Jul. 1, 1998). EPOPWH1-23.

Opposition to EP 0,620,720—Notice of Opposition by Paul Hartmann A.G., (6 sheets) (dated Dec. 16, 1998). EPOPWH1-24.

Opposition to EP Patent 0,620,720—New European Patent Specification EP 0620720B2 (published Nov. 2, 2006). EPOPWH1-25.

Opposition to EP 0,620,720—Letter to European Patent Office regarding Paul Hartmann AG, (7 sheets) (dated Mar. 6, 2006). EPOPWH1-27.

Fleischmann, W., et al., "Combination osteosynthesis in treating pilon fractures involving soft tissue injuries," in "Translation of an excerpt from the brochure regarding the Sixth German-Austrian-Swiss Accident Congress" allegedly dated 1991, in German with English translation. DENA-WH1-009.

Fleischmann, W., et al., "Combination osteosynthesis in the treatment of pylon fractures with soft tissue damage," labeled "Anlage NK10," pp. 178-181 and showing "6. German-Austrian-Swiss Trauma Conference in Vienna May 21-25, 1991," published in "Der Unfallchirurg" [The Traumatologist] in 1993, in German with English translation. DENA-WH1-006.

Juchli, L., "Krankenpflege [Nursing] Practice and Theory of Promoting Health and Patient Care," Georg Thieme Verlag Stuttgart, labeled as "Anlage 6.1" 1991 (allegedly dated Feb. 1991), and email dated May 30, 2007 labeled as "Anlage 6.2," both in German with English translations. DENA-WH1-005.

Turner, T.D., et al., eds., Excerpts from "Advances in wound management," including "Recent advances in wound management products" by T.D. Turner and "The role of foam dressings in wound management" by S. Thomas, Proceedings of a symposium held at the Welsh School of Pharmacy, University of Wales Institute of Science and Technology, Cardiff, Mar. 20-21, 1985, labeled as "Anlage NK13," 1986. DENA-WH1-008.

ISO 10079-1, "International Standard," "Medical suction equipment—Part 1: electrically powered suction equipment—Safety requirements," dated May 15, 1991. DENA-WH2-005.

"Coldex," labeled as "Anlage NK12" in German with English translation. DENA-WH1-007.

EP 0 620 720 (DE 692 24 847) Nullity Action filed at the German Federal Patent Court to nullify EP 0 620 720 (DE 692 24 847) (EP equivalent of US 5645081) and English translation, dated Jun. 28, 2007. DENA-WH1-001.

EP 0 688 189 (DE 694 25 881) Nullity Action filed at the German Federal Patent Court to nullify EP 0 688 189 (DE 694 25 881) (EP equivalent of US 5636643) with English translation, dated Jun. 28, 2007. DENA-WH2-001.

EP 0 620 720 (DE 692 24 847) Wake Forest University's Formal Response to the Jun. 28, 2007 Complaint and English translation, dated Jul. 20, 2007. DENA-WH1-002.

EP 0 688 189 (DE 694 25 881) Wake Forest University's Formal Response to the Jun. 28, 2007 Complaint and English translation, dated Jul. 20, 2007. DENA-WH2-002.

"Re. The Patentability of Claim 1 of EP 0 688 189 B2 (Patent II)" (EP equivalent of US 5636643) labeled as "Anlage NK12" in German with English translation. DENA-WH2-004.

"Analysis of Features of Claim 1 of EP 0 688 189 B2," (EP equivalent of US 5636643) labeled "Anlage NK7" in German with English translation. DENA-WH2-003,.

"Re. Patentability of Claim 1 of EP 0 620 720 B2 (Patent I)—Novelty," (EP equivalent of US 5645081) labeled "Anlage NK14," in German with English translation. DENA-WH1-003.

"Analysis of Features of Claim 1 of EP 0 620 720 B2" (EP equivalent of US 5645081) labeled as "Anlage NK5" in German with English translation. DENA-WH1-004.

Slides, drawings and photographs of patient treatment, 21 sheets, (Jeter deposition Exhibit 644) (allegedly dated 1985-1987). BS-225.
Photographs of slides showing patient treatment, 20 sheets, (Jeter deposition Exhibit 645) (allegedly dated 1985-1987). BS-226.
Photographs showing patient treatment, "sheet 1", 11 sheets, (Jeter deposition Exhibit 740) (allegedly dated 1986). BS-227.
Photographs showing patient treatment, "sheet 2", (Jeter deposition Exhibit 741) (allegedly dated 1985). BS-228.
Photographs showing patient treatment, "sheet 3", 18 sheets, (Jeter deposition Exhibit 742) (allegedly dated 1986). BS-229.
Photographs showing patient treatment, "sheet 4", 8 sheets, (Jeter deposition Exhibit 743) (allegedly dated 1985). BS-230.
Photographs showing patient treatment, "sheet 5", 21 sheets, (Jeter deposition Exhibit 744) (allegedly dated 1986). BS-231.
Pictures showing patient treatment, "sheet 1", 12 sheets, (Jeter deposition Exhibit 848) (allegedly dated 1986). BS-232.
Pictures showing patient treatment, "sheet 2", 21 sheets, (Jeter deposition Exhibit 849) (allegedly dated 1985). BS-233.
Pictures showing patient treatment, "sheet 3", 19 sheets, (Jeter deposition Exhibit 850) (allegedly dated 1986). BS-234.
Pictures showing patient treatment, "sheet 4", 8 sheets, (Jeter deposition Exhibit 851) (allegedly dated 1985). BS-235.
Pictures showing patient treatment, "sheet 5", 21 sheets, (Jeter deposition Exhibit 852) (allegedly dated 1986). BS-236.
Documents included as Jeter deposition Exhibit 854, BS-237.
Document "Ex. 5" from deposition of D. Tumey, (dated Mar. 1990). BS-244.
Svedman, "Irrigation Treatment of Leg Ulcers", The Lancet, Sep. 3, 1983, pp. 532-534. NPL-679.
Svedman, P., et al., "Staphylococcal wound infection in the pig: Part I. Course," Ann. Plast. Surg., 23(3):212-218, (Sep. 1989). NPL-684.
Mendez-Eastman, S., "Guidelines for using negative pressure wound therapy", Adv. Skin Wound Care, 14 (6):314-323. (16 pp.) (Nov.-Dec. 2001). NPL-278.
Addition to the "Users Manual Concerning Overflow Protection-Concerns all Egnell Pumps", dated Feb. 3, 1983, 1 page Swedish, [1 page English]. NPL-680.
Addition to the "Users Manual Concerning Overflow Protection—Concerns all Egnell Pumps", dated Feb. 3, 1983, 2 pages of English translation. NPL-683.
Aeros, "Moblvac,""introducing the 'off the wall' vacuum system," Aeros Instruments, Life Support Nursing, 3(1):34-37, Barlin Publishing Ltd. (Jan.-Feb. 1980). NPL-007.
Article in Russian, pp. 84-85; NPL-619.
Austad, E.D., et al., "Tissue expansion: dividend or loan?"Plast. Reconstr. Surg.,78(1):63-67 (Jul. 1986). NPL-023.
BlueSky Medical, 2 sheets of advertisement, "Introducing the Chariker-Jeter wound drainage kit" and "Introducing the Kremlin® wound drainage kit" NPL-620.
Cattaneo, R., et al., "Treatment of septic or non-septic diaphyseal pseudoarthroses by Ilizarov's monofocal compression method", Rev. Chir. Orthop. Reparatrice Appar. Mot., (1 sheet printout from PubMed); 71(4):223-229 (1985). NPL-674.
Egnell Minor, Instruction Book, First Addition [Edition], allegedly dated Feb. 1987, 21 pages Swedish, 3 pages English. NPL-681.
Egnell Minor, Instruction Book, First Edition allegedly dated Feb. 1987, 34 pages of English translation. NPL-682.
Feierabend, T.C., et al., "Injuries causing major loss of scalp", Plast. Reconstr. Surg, [Abstract only—1 pp. printout from PubMed], 76(2):189-194 (Aug. 1985). NPL-623.
Geronemus, R.G., et al., "The effect of two new dressings on epidermal wound healing", J. Dermatol. Surg. Oncol., 8(10):850-852 (Oct. 1982). NPL-606.
Harkiss, K., "Leg ulcers cheaper in the long run", Community Outlook, pp. 19, 21, 22 (Aug. 14, 1985). NPL-190.
Lascombes, P., et al., "Ilizarov's method. Histological and radiological aspects", J. Radiol., (1 sheet printout from PubMed); 72(1):11-16 (Jan. 1991). NPL-677.
Miller, S.H., et al., "An inexpensive wound suction device", Surg. Gyencol. Obstet., 141(5):768 (Nov. 1975). NPL-607.
Miller, S.J., "Surgical wound drainage system using silicone tubing", J. Am. Podiatry Assn., 71(6): pp. 287-296, (Jun. 1981). NPL-605.
Molnar, J.A., "V.A.C. and burn care", presentation. WFU-74.

Nelson, R.P., et al., "Use of negative pressure suction in urology", Urology, 4(5):574-576, (Nov. 1974). NPL-494.
Sanden, G., et al., "Staphylococcal wound infection in the pig: Part II. Inoculation, quanitifcation of bacteria, and reproducibility," Ann. Plast. Surg., 23(3):219-223, (Sep. 1989). NPL-685.
Slides from Wake Forest University regarding use of V.A.C. WFU-75.
Spahn, J.G., "Soft tissue challenges in the head and neck region,"Clinical Seminar Handout, EHOB, (46 pages) NPL-621.
Stewart, A., et al., "Cleaning v. healing," Community Outlook, pp. 22, 24 & 26 (Aug. 14, 1985). NPL-601.
Trammell, T.R., et al., "Closed-wound drainage systems: the Solcotrans Plus versus the Stryker-CBC ConstaVAC", Orthopaedic Review, 20(6):536-542 (Jun. 1991). NPL-608.
Woodley, D.T., et al., "A double-blind comparison of adhesive bandages with the use of uniform suction blister wounds", Arch. Dermatol., 128(10):1354, 1357 (Oct. 1992). NPL-609.
Zelko, J.R., et al., "Primary closure of the contaminated wound; closed suction wound catheter", Am. J. Surgery, 142:704-706, (Dec. 1981). NPL-604.
*KCI v. BlueSky*, Amended answer to third amended complaint, additional defenses, second amended counterclaims and jury demand of Medela, Inc. dated Jul. 12, 2005. BS-223.
*KCI v. BlueSky*, Order denying defendant BlueSky's motion for new trial, dated Apr. 4, 2007. BS-238.
*KCI v. BlueSky*, Order denying plaintiffs motion for new trial or judgment as a matter of law, dated Apr. 4, 2007. BS-239.
*KCI v. BlueSky*, Order denying defendant Medela's renewed motion for judgment as a matter or law, or, alternatively, a new trial on patent invalidity and defendant BlueSky's motion for new trial, dated Apr. 4, 2007. BS-240.
*KCI v. BlueSky*, Order denying defendant Medela's motion for new trial on unenforceability and defendant BlueSky's motion for new trial, dated Apr. 4, 2007. BS-241.
*KCI v. BlueSky*, Order denying plaintiffs rule 60(b) motion for new trial, dated Apr. 4, 2007. BS-242.
*KCI v. BlueSky*, Final Judgment, dated Apr. 4, 2007. BS-243.
*KCI v. BlueSky*, Plaintiffs Argument, Markman Hearing, Nov. 14, 2005. BS-246.
U.S. Appl. No. 10/227,161—Official action (Feb. 9, 2004).
U.S. Appl. No. 10/227,161—Applicants' response (Jun. 8, 2004).
U.S. Appl. No. 10/227,161—Official action (Sep. 20, 2004).
U.S. Appl. No. 10/227,161—Applicants' response (Mar. 17, 2005).
U.S. Appl. No. 10/227,161—Official action (Jun. 7, 2005).
U.S. Appl. No. 10/227,161—Applicants' response (Sep. 28, 2005).
U.S. Appl. No. 10/227,161—Official action (Dec. 5, 2005).
U.S. Appl. No. 10/227,161—Applicants' response (May 2, 2006).
U.S. Appl. No. 10/227,161—Final Official action (Aug. 2, 2006).
U.S. Appl. No. 10/227,161—Official action (Apr. 13, 2007).
U.S. Appl. No. 10/227,161—Applicants' response (Oct. 15, 2007).
U.S. Appl. No. 10/647,068—Official action (Sep. 20, 2004).
U.S. Appl. No. 10/647,068—Applicants' response (Mar. 17, 2005).
U.S. Appl. No. 10/647,068—Official action (Jun. 7, 2005).
U.S. Appl. No. 10/647,068—Applicants' response (Sep. 28, 2005).
U.S. Appl. No. 10/647,068—Official action (Dec. 21, 2005).
U.S. Appl. No. 10/647,068—Applicants' response (May 2, 2006).
U.S. Appl. No. 10/647,068—Final official action (Aug. 11, 2006).
U.S. Appl. No. 10/647,068—Official action (Apr. 13, 2007).
U.S. Appl. No. 10/647,068—Applicants' response (Oct. 15, 2007).
U.S. Appl. No. 10/161,076—Official action (Dec. 3, 2003).
U.S. Appl. No. 10/161,076—Applicants' response (Jun. 2, 2004).
U.S. Appl. No. 10/161,076—Final official action (Sep. 13, 2004).
U.S. Appl. No. 10/161,076—Final official action (Dec. 15, 2004).
U.S. Appl. No. 10/161,076—Applicants' response (Jun. 15, 2005).
U.S. Appl. NO. 10/161,076—Official action (Sep. 7, 2005).
U.S. Appl. No. 10/161,076—Applicants' response (Mar. 7, 2006).
U.S. Appl. No. 10/161,076—Final official action (May 24, 2006).
U.S. Appl. No. 10/161,076—Applicants' response (Nov. 21, 2006).
U.S. Appl. No. 10/161,076—Official action (Sep. 14, 2007).
*KCI v. BlueSky*, Transcript of Deposition of Jeffrey A. Niezgoda, M.D., with Exhibits, dated May 1, 2006. parts 1-24 of 50. BS-94.
*KCI v. BlueSky*, Transcript of Deposition of Jeffrey A. Niezgoda, M.D., with Exhibits, dated May 1, 2006. parts 25-50 of 50. BS-94.

Chen, L., et al., "An experimental study on the implantation of a biomaterial with electro-activity for replacement of hard tissue in bone", Hua Xi Yi Ke Da Xue Xue Bao, (2 pp. printout from PubMed); 32(4):526-8, 554, (Dec. 2001). NPL-661.

Aronson, J., et al., "Mechanical forces as predictors of healing during tibial lengthening by distraction osteogenesis", Clin. Orthop. Rel. Res., (301):73-79, (Apr. 1994). NPL-640.

Kassis, B., et al., "Callus response to micromovement after elongation in the rabbit", J. Pediatr. Orthop., 16 (4):480-483, (Aug. 1996). NPL-641.

Duda, G.N., et al., "Interfragmentary motion in tibial osteotomies stabilized with ring fixators", Clin. Orthop., (396):163-172, (Mar. 2002). NPL-642.

Farrar, M., et al., "The Sheffield hybrid fixator—a clinical and biomechanical review", Injury, Int. J. Care Injured, 32: S-D-8 S-D-13 (2001). NPL-643.

Goodship, A.E., et al., "Functional adaptation of bone to increased stress", J. Bone Joint Surg., 61-A(4):539-546 (Jun. 1979). NPL-644.

Goodship, A.E, et al., "The influence of induced microenvironment upon the healing of experimental tibial fractures", J. Bone Joint Surg., 67-B(4):650-655 (Aug. 1985). NPL-645.

Goodship, A.E., et al., "Strain rate and timing of stimulation in mechanical modulation of fracture healing", Clin. Orthop. Rel. Res., (and 1 sheet printout from PubMed); (355S):S105-S115, (Oct. 1998). NPL-646.

Gordon, J.E., et al., "Treatment of rigid hypertrophia posttraumatic pseudarthorsis of the tibia n children using distraction osteogenesis", J. Pediatr. Orthop., 22(4): 419-423 (2002). NPL-647.

Kenwright, J., et al., "Controlled mechanical stimulation in the treatment of tibial fractures", Clin. Orthop. Rel. Res., (241):36-47 (Apr. 1989). NPL-648.

Kocaoglu, M., et al., "Treatment of humeral shaft non-unions by the Ilizarov method", Int. Orthop. (SICOT), 25:396-400 (2001). NPL-649.

Lanyon, L.E., et al., "Bone deformation recorded in vivo from strain gauges attached to the human tibial shaft", Acta Orthop. Scand., 46:256-268 (1975). NPL-650.

Mofid, M.M., et al., "Callus stimulation in distraction osteogenesis", Plast. Reconstr. Surg., 109:1621-1629 (Apr. 15, 2002). NPL-651.

Maffulli, N., et al., "Bone mineralization at the callotasis site after completion of lengthening", Bone, 25(3):333-338 (Sep. 1999). NPL-652.

Paley, D., "Current techniques of limb lengthening", J. Pediatr. Orthop., 8(1):73-92 (1988). NPL-653.

Pavolini, B., et al., "The Ilizarov fixator in trauma: a 10-year experience", J. Orthop. Sci., 5:108-113, (2000). NPL-654.

Rozbruch, S.R., et al., "Distraction of hypertrophic nonunion of tibia with deformity using Ilizarov/Taylor Spatial Frame", Arch. Orthop. Trauma Surg., 122:295-298 (2002). NPL-655.

Rozbruch, S.R., et al., "Distraction osteogenesis for nonunion after high tibial osteotomy", Clin. Orthop. Rel. Res., (394):227-235 (Jan. 2002). NPL-656.

Sakurakichi, K., et al., "Ankle arthrodesis combined with tibial lengthening using the Ilizarov apparatus", J. Orthop. Sci., 8:20-25 (2003). NPL-657.

Tsuchiya, H, et al., "Distraction osteogenesis for treatment of bone loss in the lower extremity", J. Orthop. Sci., 8:116-124 (2003). NPL-658.

Waanders, N.A., et al., "Evaluation of the mechanical environment during distraction osteogenesis", Clin. Orthop. Rel. Res., 1(349):225-234 (Apr. 1998). NPL-659.

Fischgrund, J., et al., "Variables affecting time to bone healing during limb lengthening", Clin. Orthop. Rel. Res., (301):31-37 (Apr. 1994). NPL-660.

Stokes, I.A., et al., J. Bone Joint Surg., 84(10):1842, Figure 02, (1 sheet showing "Fig. 2-A: Diagrammatic representation of the measurement of the height of the hypertrophic zone and the heights of chondrocytes"); printout dated Apr. 16, 2004. NPL-662.

Stokes, I.A., et al., "Enlargement of growth plate chondrocytes modulated by sustained mechanical loading", J. Bone Joint Surg. (Am.), (and 2 pp. printout from PubMed); 84-A(10):1842-1848 (Oct. 2002). NPL-663.

Tanaka, S.M., "A new mechanical stimulator for cultured bone cells using piezoelectric actuator", J. Biomech., (and 1 sheet printout from PubMed); 32(4):427-430 (Apr. 1999). NPL-664.

Alberty, A., et al., "Effects of distraction and compression on proliferation of growth plate chondrocytes. A study in rabbits.", Acta Orthop. Scand., (1 sheet printout from PubMed); 64(4):449-455 (Aug. 1993). NPL-665.

Campbell, P., "Arthrodesis of the ankle with modified distraction-compression and bone-grafting", J. Bone Joint Surg. Am., (1 sheet printout from PubMed); 72(4):552-556 (Apr. 1990). NPL-666.

Monticelli, G., et al., "Leg lengthening by closed metaphyseal corticotomy", Ital. J. Orthop. Traumatol., (1 sheet printout from PubMed); 9(2):139-150 (Jun. 1983). NPL-667.

Shevtsov, V., et al., "Reduction of the period of treatment for leg lengthening. Technique and advantages", Rev. Chir. Orthop. Reparatrice Appar. Mot., (1 pp. printout from PubMed); 87(3):248-256 (May 2001). NPL-668.

Paley, D., "Correction of limb deformities in the 21st century", J. Pediatr. Orthop., 20(3):279-281 (May / Jun. 2000). NPL-669.

Goodship, A.E., "Cyclical micromovement and fracture healing", J. Bone Joint Surg., 78-B(1):166-167 (Jan. 1996). NPL-670.

De Bastiani, G., et al., "Limb lengthening by callus distraction (callotasis)", J. Pediatr. Orthop., (1 sheet printout from PubMed); 7(2):129-134 (Mar. / Apr. 1987). NPL-671.

De Bastiani, G., et al., "Dynamic axial fixation. A rational alternative for the external fixation of fractures", Int. Orthop., (1 sheet printout from PubMed); 10(2):95-99 (1986). NPL-672.

Patel, V.R., et al., "Nonunion of the humerus after failure of surgical treatment. Management using the Ilizarov circular fixator", J. Bone Joint Surg. Br., (1 sheet printout from PubMed); 82(7):977-83 (Sep. 2000). NPL-673.

Bronson, D.G., et al., "Stabilization of a short juxta-articular bone segment with a circular external fixator", J. Pediatr. Orthop. Part B (1 sheet printout); 11:143-149 (Apr. 2002). NPL-675.

Duda, G.N., et al., "Interfragmentary movements in the early phase of healing in distraction and correction osteotomies stabilized with ring fixators", Langenbecks Arch. Surg., (1 sheet printout from PubMed); 387 (11-12):433-440 (Feb. 2003). NPL-676.

Raschke, M., et al., "Nonunion of the humerus following intramedullary nailing treated by Ilizarov hybrid fixation", J. Orthop. Trauma, (1 sheet printout from PubMed); 12(2):138-141 (Feb. 1998). NPL-678.

*KCI et al.* v. *Blue Sky Medical Group et al.*, Case No. 2007-1340, -1341, -1342, Reply brief of appellants, Medela AG and Medela, Inc., filed by Medela on May 15, 2008. CAFC1340-003.

*KCI et al.* v. *Blue Sky Medical Group et al.*, Case No. 2007-1340, -1341, -1342, Response and reply brief of defendant-appellant, Blue Sky Medical Group Inc., filed by Blue Sky on May 15, 2008. CAFC1340-004.

Bagautdinov, N.A., "Variant of external vacuum aspiration in the treatment of purulent disease of soft tissue," pp. 94-96 and Introduction by V.E. Volkov and an opinion by V. V. Shutova dated Feb. 4, 2009, in Russian with English translation, with alleged card catalogue card with English translation, and certification of translation dated Feb. 19, 2009, Current Problems in Modern Clinical Surgery, (1986). NPL-724.

Kuznetsov, V.A., "Vacuum and vacuum-sorption treatment of open septic wounds," in II All-union conference "Wounds and wound infection" "(Abstracts of presentations)" in Russian with English translation, and card with English translation, Moscow, Oct. 28-29, 1986. NPL-725 (Bagautdinov II).

Robson, M.C., et al., Chapter 10 "Wounds and wound healing," p. 107-114 in Essentials of General Surgery, P.F. Lawrence ed., Williams & Wilkins, (1988). NPL-714.

Robson, M.C., et al., Chapter 11 "Wounds and wound healing," p. 119-126 in Essentials of General Surgery, 2nd edition, P.F. Lawrence ed., Williams & Wilkins, (1992). NPL-715.

Smith, D.J. Jr., et al., Chapter 7 "Wounds and wound healing," p. 113-122 in Essentials of General Surgery, 3d edition, P.F. Lawrence ed., Lippincott Williams & Wilkins, (2000). NPL-716.

Talboy, G.E., et al., "Chapter 8: Wounds and wound healing," p. 147-161 in Essentials of General Surgery, B. Sun ed., Lippincott Williams & Wilkins, (2006). NPL-717.

Garrison, R.N., et al., "Chapter 9: Surgical infections," p. 163-179 in Essentials of General Surgery, B. Sun ed., Lippincott Williams & Wilkins, (2006). NPL-718.
Sumpio, B.E., et al., "Role of negative pressure wound therapy in treating peripheral vascular graft infections," Vascular, 16(4):194-200, (2008). NPL-719.
Taber's Cyclopedic Medical Dictionary, Edition 20, pp. 306-309, 728-729, 765, 1726, and 2006-2009. (2005). NPL-720.
Mills, N., Polymer Foams Handbook: engineering and biomechanics applications and design guide, pp. 2-3, (2007). NPL-722.
Bucknall, T.E., et al.. eds., "Sutures and dressings," p. 88-93 in Wound Healing for Surgeons, (1984). NPL-723.
Parker, S.P., ed., McGraw-Hill Dictionary of Scientific and Technical Terms, 5th ed., pp. 139, 533, 772, and 1672 (1994). NPL-726.
Merriam-Webster Online, "reepithelialization," printout of webpage dated Apr. 17, 2009. NPL-727.
Oxford English Dictionary Online, "deformable," "deform," and "flexible," printout of webpages dated Apr. 17, 2009. NPL-728.
Alger, M.S.M., Polymer Science Dictionary, (4 sheets), Elsevier Science Publishers Ltd. (1989). NPL-729.
Stedman's Medical Dictionary, 25th ed., pp. 554, 667-668, and 1603-1604, Williams & Wilkins, (1990). NPL-730.
Webster's New World Dictionary of the American Language, pp. 1105, Simon & Schuster, Inc., (1984). NPL-731.
Transeal transparent wound dressing, DeRoyal, 4 sheets (2003). NPL-733.
Kuznetsov, V.A., "Vacuum and vacuum-sorption treatment of open septic wounds," in II All-union conference "Wounds and wound infections" "(Presentation abstracts)" in Russian with English translation dated Apr. 2, 2009, with table of contents, Moscow, Oct. 28-29, 1986. NPL-734.
British Pharmacopoeia 19, vol. II, p. 927 and p. 548 of 1986 addendum, (vol. II—1980, addendum—1986). NPL-738.
KCI, "The V.A.C. operations summary," 7 sheets, (1999). NPL-732.
Kanshin, N.N., "Closed treatment of suppurative processes by the method of active lavage drainage," Third Surgical Clinic of the N.V. Sklifosovkiy Moscow Scientific Research Institute of Emergency Care, pp. 18-23, (6 sheets in English, 6 sheets in Russian and English abstract on pp. 22-23), allegedly submitted 1979. NPL-710.
Lokhvitskii, S.V., et al., "External vacuum aspiration in the treatment of purulent disorders of the soft tissues," Inpatient Surgery Clinic of the Therapeutic Department at Karagandy Medical Institute, Municipal Hospital No. 1, Temirtau, pp. 130-134 (5 sheets English, 5 sheets Russian), allegedly submitted Sep. 22, 1982. NPL-709.
Ersh, Z. Ya., "Use of polyurethane foam for treating purulent cavities and wounds," Purulent Septic Unit of Hospital No. 35, (2 sheets English and 2 sheets Russian), allegedly submitted for publication Mar. 21, 1984. NPL-708.
3M™ Tegaderm™ Transparent film dressings—wound, Commonly asked questions, 4 sheets, (Jan. 2007). NPL-737.
Greene, A.K., et al., "Microdeformational wound therapy," Ann. Plast. Surg., 56(4):418-422, (2006). NPL-713.
Bui, T.D., et al., "Negative pressure wound therapy with off-the-shelf components," Am. J. Surg., 192:235-237, (2006). NPL-706.
PCT/US08/79364—Written Opinion and International Search Report (Dec. 16, 2008).
Taber's Cyclopedic Medical Dictionary, 16th edition, pp. 613-614, 643, 679, 1444, and 1686-1688, (1989). NPL-740.
Parker, S.P., ed., McGraw-Hill Dictionary of Scientific and Technical Terms, 4th ed., pp. 1462, (1989). NPL-741.
Gove, P.B., ed., Webster's Third New International Dictionary Unabridged, pp. 869 and 2627 (1986). NPL-742.
Stedman's Medical Dictionary, 25th ed., pp. 1739, Williams & Wilkins, (1990). NPL-743.
Kirk-Othmer, Encyclopedia of Chemical Technology, 2nd completely revised edition, vol. 9, pp. 220-232, John Wiley & Sons, Inc., (1966). NPL-744.
Standard Operating Procedure, The determination of moisture vapour permeability (MVP) and water transmission rate (WTR), implementation date: Sep. 11, 2006 and QA Operational Laboratories Analytical Report dated Nov. 13, 2008.. NPL-745.

British Pharmacopoeia Selections: (1988) vol. II, p. 1126-1127, A223-A224; Addendum 1992, p. 1494; (1993) vol. II, p. 1266, A218-A219. NPL-746.
PCT/US08/30581—Written Opinion and International Search Report—ISR (Feb. 20, 2009).
PCT/US03/16763—Written Opinion, International Preliminary Examination Report, and International Search Report,—ISR (Dec. 18, 2003, Apr. 19, 2004, and Sep. 2, 2004).
Reexam of US 5,645,081, Reexam No. 90/008,692, Statement under 37 CFR 1.565(a), Notice of court action, filed Feb. 21, 2008. RE-012.
Reexam of US 5,645,081, Reexam No. 90/008,692, Non-final office action mailed Feb. 28, 2008. RE-013.
Reexam of US 5,645,081, Reexam No. 90/008,692, Response to non-final office action and exhibit A, filed Apr. 28, 2008. RE-014.
Reexam of US 5,636,643, Reexam No. 90/008,697, Order granting reexamination, and list of references considered by examiner, mailed Nov. 26, 2007. RE-015.
Reexam of US 5,636,643, Reexam No. 90/008,697, Statement under 37 CFR 1.565(a), Notice of court action, filed Feb. 21, 2008. RE-016.
Reexam of US 5,636,643, Reexam No. 90/008,697, Non-final office action mailed Feb. 28, 2008. RE-017.
Reexam of US 5,636,643, Reexam No. 90/008,697, Response to non-final office action and exhibit A, filed Apr. 28, 2008. RE-018.
Reexam of US 7,198,046, Reexam No. 90/008,711, Order granting reexamination, and list of references considered by examiner, mailed Nov. 26, 2007. RE-019.
Reexam of US 7,198,046, Reexam No. 90/008,711, Statement under 37 CFR 1.565(a), Notice of court action, filed Feb. 21, 2008. RE-020.
Reexam of US 7,198,046, Reexam No. 90/008,711, Non-final office action mailed Feb. 29, 2008. RE-021.
Reexam of US 7,198,046, Reexam No. 90/008,711, Response to non-final office action and exhibit A, filed Apr. 29, 2008. RE-022.
Reexam of US 7,216,651, Reexam No. 90/008,693, Order granting reexamination, and list of references considered by examiner, mailed Nov. 26, 2007. RE-023.
Reexam of US 7,216,651, Reexam No. 90/008,693, Statement under 37 CFR 1.565(a), Notice of court action, filed Feb. 21, 2008. RE-024.
Reexam of US 7,216,651, Reexam No. 90/008,693, Non-final office action mailed Feb. 28, 2008. RE-025.
Reexam of US 7,216,651, Reexam No. 90/008,693, Response to non-final office action and exhibit A, filed Apr. 28, 2008. RE-026.
Svedman, P., et al., "A dressing system providing fluid supply and suction drainage used for continuous or intermittent irrigation", Ann. Plast. Surg., 17(2):125-33 (Aug. 1986). NPL-389.
"Pressure equivalents," McGraw-Hill Encyclopedia of Science & Technology, 6th ed., New York, pp. 249, (1987). NPL-687bw.
*ITI v. KCI*, Case No. 07-589, Reply brief in support of defendants' motion to dismiss complaint, filed by KCI on Dec. 12, 2007. DED-005.
*ITI v. KCI*, Case No. 07-589, First amended complaint, filed by ITI on Jan. 25, 2008. DED-006.
*ITI v. KCI*, Case No. 07-589, Defendants' motion, Proposed order, and Opening brief in support of defendants' motion to dismiss first amended complaint, or, alternatively, to transfer the case to the Middle District of North Carolina, filed by KCI on Mar. 12, 2008. DED-007.
*ITI v. KCI*, Case No. 07-589, Plaintiffs opposition to defendants' motion to dismiss, with declarations, filed by ITI on Apr. 4, 2008. DED-008.
*ITI v. KCI*, Case No. 07-589, Reply brief in support of defendants' motion to dismiss first amended complaint, or, alternatively, to transfer the case to the Middle District of North Carolina, filed by KCI on Apr. 21, 2008. DED-009.
*KCI v. Medela*, Case No. 08-cv-00087, (formerly 2:07cv187), Plaintiffs memorandum in support of continuing to stay litigation pending reexamination of U.S. Patent No. 7,216,651 and conclusion of related appeal, filed by Medela on May 9, 2008. SA087-001.
*KCI v. Medela*, Case No. 08-cv-00087, (formerly 2:07cv187), Plaintiffs KCI's and Wake Forest's brief in opposition to Medela's motion to stay, Proposed order denying Medela's motion to stay, with Exhibits, filed by KCI on May 16, 2008. SA087-002.
*KCi v. Medela*, Case No. 08-cv-00087, (formerly 2:07cv187), Defendants' reply to KCI's and Wake Forest's Brief in opposition to continue to stay litigation pending reexamination of U.S. Patent No. 7,216,651 and conclusion of related appeal, with Proposed order, filed by Medela on May 21, 2008. SA087-003.

*KCI, et al.,* v. *Blue Sky Medical Group, Inc., et al.,* SA08-cv-102, (formerly 2:07cv188), Defendants Blue Sky Medical Group, Inc.'s and Smith & Nephew, Inc.'s motion to stay, with Proposed order and Exhibits, filed by Blue Sky on May 9, 2008. SA00102-001.
*KCI, et al.,* v. *Blue Sky Medical Group, Inc., et al.,* SA08-cv-102, (formerly 2:07cv188),Plaintiffs KCI's and Wake Forest's brief in opposition to defendants' motion to stay, with Proposed order and Exhibits, filed by KCI on May 16, 2008. SA00102-002.
*KCI, et al.,* v. *Blue Sky Medical Group, Inc., et al.,* SA08-cv-102, (formerly 2:07cv188), Defendants Blue Sky Medical Group, Inc.'s and Smith & Nephew, Inc.'s reply in support of their motion to stay, with exhibit, filed by Blue Sky on May 21, 2008. SA00102-003.
*Medela* v. *KCI,* Case No. 7cv449, Plaintiff's memorandum in support of continuing to stay litigation pending reexamination of U.S. Patent No. 7,216,651 and conclusion of related appeal, filed by Medela on May 9, 2008. SA449-007.
*Medela* v. *KCI,* Case No. 7cv449, Plaintiffs KCI's and Wake Forest's brief in opposition to Medela's motion to stay with Proposed order and exhibits, filed by KCI on May 16, 2008. SA449-008.
*Medela* v. *KCI,* Case No. 7cv449, Plaintiffs reply to KCI's and Wake Forest's Brief in opposition to continue to stay litigation pending reexamination of U.S. Patent No. 7,216,651 and conclusion of related appeal, with Proposed order and exhibit, filed by Medela on May 21, 2008. SA449-009.
*Blue Sky* v. *KCI,* Case No. 7cv454, Plaintiffs Blue Sky Medical Group, Inc.'s and Smith & Nephew, Inc.'s motion to stay, Proposed order, and exhibits, filed by Blue Sky on May 9, 2008. SA454-008.
*Blue Sky* v. *KCI,* Case No. 7cv454, Plaintiffs KCI's and Wake Forest's brief in opposition to defendants' motion to stay, with Proposed order and exhibits, filed by KCI on May 16, 2008. SA454-009.
*Blue Sky* v. *KCI,* Case No. 7cv454, Plaintiffs Blue Sky Medical Group, Inc.'s and Smith & Nephew, Inc.'s reply in support of their motion to stay, filed by Blue Sky on May 21, 2008. SA454-010.
*KCI et al.* v. *Blue Sky Medical Group et al.,* Case No. 2007-1340, -1341, -1342, Corrected reply brief of appellants, Medela AG and Medela, Inc., filed by Medela on May 21, 2008. CAFC1340-005.
*WFU* v. *ITI,* 1:08-cv-32, Answer to complaint with jury demand, filed by ITI on Mar. 4, 2008. MDNC32-002.
*WFU* v. *ITI,* 1:08-cv-32, Defendant ITI's motion to transfer venue, Proposed order, and Brief in support of defendant ITI's motion to transfer venue, or in the alternative, motion to stay, filed by ITI on Mar. 12, 2008. MDNC32-003.
*WFU* v. *ITI,* 1:08-cv-32, Plaintiffs' brief in opposition to defendant's motion to transfer venue, or in the alternative, motion to stay, filed by WFU on Apr. 18, 2008. MDNC32-004.
*WFU* v. *ITI,* 1:08-cv-32, Defendant ITI's reply brief in support of its motion to transfer venue, or in the alternative, motion to stay, with exhibits, filed by ITI on May 5, 2008. MDNC32-005.
*KCI* v. *BlueSky,* Trial Transcript for Orgill/Bridi/McGregor/Girolami/Taylor, dated Jul. 12, 2006. BS-116.
*KCI et al.* v. *Blue Sky Medical Group et al.,* Case No. 2007-1340, -1341, -1342, Reply brief of Plaintiffs-Cross Appellants, filed by KCI and Wake Forest on Jul. 2, 2008. CAFC1340-006.
Zivadinovic, G., et al., "Vacuum therapy in the treatment of peripheral blood vessels," Timok Medical Journal, Abstract book of the 5th Timok Medical Days, Majdanpek, 6 sheets of English translation, (1986). NPL-703.
Safronov, A.A., "Vacuum therapy for trophic ulcers of the tibia with concurrent skin autoplasty," Dissertation abstract, additional abstract, Moscow, 20 sheets of English translation, (1967). NPL-704.
Safronov, A.A., Abstract of Invention No. 240188, "Device for wound or ulcer treatment," (2 sheets English translation and 2 sheets in Russian) (1969). NPL-705.
Parikh, R.S., et al., "Self-adhesive drape (Opsite) for management of leaking abdominal wounds", Indian J. Gastroenterol., 19(4):178-180 (Oct. / Dec. 2000). NPL-631.
Alexis, A.F., et al., "Reassessment of the suction blister model of wound healing: introduction of a new higher pressure device", Int. J. Dermatol., 38(8):613-617 (Aug. 1999). NPL-632.
Gnanaraj, J., "A simple, sterile, low-cost, closed suction drainage system", Trop. Doct., 27(2):104 (Apr. 1997). NPL-633.
Klemm, K.W., "Antibiotic bead chains", Clin. Orthop. Rel. Res., (295):63-76 (Oct. 1993). NPL-634.

Pignatti, M., et al., "Mobile-Vac for the treatment of lower limb ulcers", Plast. Reconstr. Surg., 108(6):1837-1838 (Nov. 2001). NPL-635.
Schaum, K.D., "Payment strategies: a new medicare part B wound care policy", Adv. Skin & Wound Care, 14 (5):238-240 (Sep. / Oct. 2001). NPL-636.
Chariker, M.E., Presentation entitled, "Vacuum therapy in wound management", (Chariker deposition exhibit No. 1220), dated Oct. 27, 2005. NPL-637.
Chariker, M.E., Presentation entitled, "Closed wound suction", (Chariker deposition exhibit No. 1219), dated Mar. 17, 2005. NPL-638.
Argenta, L.C., et al., "Vacuum-assisted closure: state of clinic art", Plast. Reconstr. Surg., 117 (7 Suppl.): 127S-142S (Jun. 2006). WFU-64.
Chung, C.J., et al., "Case review: management of life-threatening sepsis and wound healing in a Klippel-Trenaunay patient using serial surgical debridements and vacuum-assisted closure", Eur. J. Plast. Surg., 26:214-216 (2003). WFU-61.
Dedmond, B.T., et al., "Subatmospheric pressure dressings in the temporary treatment of soft tissue injuries associated with type III open tibial shaft fractures in children", J. Pediatr. Orthop., 26(6):728-732, (Nov.-Dec. 2006). WFU-67.
Dedmond, B.T., et al., "The use of negative-pressure wound therapy (NPWT) in the temporary treatment of soft tissue injuries associated with high-energy open tibial shaft fractures", J. Orthop. Trauma, 21(1):11-17, (Jan. 2007). WFU-68.
Gemeinhardt, K.D., et al., "Vacuum-assisted closure for management of a traumatic neck wound in a horse", Equine Veterinary Education, 17(1):27-33, (2005). WFU-72.
Laverty, D., et al., "Negative pressure wound therapy in the management of orthopedic wounds", Ostomy Wound Manage., 50(11A suppl):18S-9S (Nov. 2004). WFU-56.
Molnar, J.A., "Applications of negative pressure wound therapy to thermal injury", Ostomy Wound Manage., 50(4A suppl):17-9 (Apr. 2004). WFU-58.
Molnar, J.A., "The science behind negative pressure wound therapy", Ostomy Wound Manage., 50 (4A suppl):2-5 (Apr. 2004). WFU-59.
Molnar, J.A., et al., "Management of an acute thermal injury with subatmospheric pressure", J. Burns Wounds, 4:83-92, 4:e5 (published online Mar. 24, 2005). WFU-43.
Morykwas, M.J., et al., "Effects of varying levels of subatmospheric pressure on the rate of granulation tissue formation in experimental wounds in swine", Ann. Plast. Surg., 47(5):547-551 (Nov. 2001). WFU-44.
Plikaitis, C.M., et al., "Subatmospheric pressure wound therapy and the vacuum-assisted closure device: basic science and current clinical successes", Expert Rev. Med. Devices, 3(2):175-184, (Mar. 2006). WFU-63.
Schlatterer, D., et al., "Orthopedic indications for negative pressure wound therapy", Ostomy Wound Manage., 51 (2A suppl):27S-8S (Feb. 2005). WFU-57.
Schneider, A.M., et al., "Re: use of specialized bone screws for intermaxillary fixation: reply", Ann. Plast. Surg., 47 (1): 93, (Jul. 2001). WFU-70.
Webb, L.X., et al., "The contaminated high-energy open-fracture: a protocol to prevent and treat inflammatory mediator storm-induced soft-tissue compartment syndrome (IMSICS)", J. Am. Acad. Orthop. Surg., 14(10):SA82-S86 (Oct. 2006). WFU-69.
Yang, C.C., et al., "Vacuum-assisted closure for fasciotomy wounds following compartment syndrome of the leg", J. Surg. Orthop. Adv., 15(1):19-23 (Spring 2006). WFU-66.
Argenta, A., et al., "Deformation of superficial and deep abdominal tissues with application of a controlled vacuum", European Tissue Repair Society, Focus group meeting Topical Negative Pressure (TNP) Therapy, London UK ( Dec. 4-6, 2003). WFU-55.
Argenta, L.C., et al., "The V.A.C. as an adjunct for treatment for abdominal wounds", 66th Annual Meeting of the American Society of Plastic and Reconstructive Surgeons, San Francisco, CA, pp. 330-331; 1 sheet of abstract (Sep. 21-24, 1997). WFU-39.

Argenta, L.C., et al., "Vacuum assisted closure of chronic wounds", 65th Annual Scientific Meeting, American Society of Plastic and Reconstructive Surgeons, Dallas, TX, pp. 226-227; 1 sheet of abstract (Nov. 9-13, 1996). WFU-37.

Defranzo, A.J., et al., "The use of V.A.C. therapy for treatment of lower extremity wounds with exposed bone", 68th Annual Meeting of the American Society of Plastic and Reconstructive Surgeons, New Orleans, LA, pp. 37-38; 2 sheets of abstract (Oct. 24-27, 1999). WFU-42.

Kortesis, B., et al., "Vacuum-assisted closure for the treatment of open tibia fractures", 72nd Annual Meeting of the American Society of Plastic Surgeons, San Diego, CA, pp. 172-173; 1 sheet of abstract (Oct. 25-29, 2003). WFU-41.

Kremers, L., et al., "Effect of topical sub-atmospheric pressure treatment on angiotensin I and II levels post burn", 35th Annual Meeting, Abstract printed in J. Burn Care Rehabilitation, p. S44, Abstract No. 3 American Burn Association, Miami, Florida (Apr. 1-4 2003). WFU-54.

Kremers, L., et al., "Serum interleukin levels post burn with and without application of sub-atmospheric pressure", 35th Annual Meeting, Abstract printed in Burn Care Rehabilitation, p. S43, Abstract No. 2, American Burn Association, Miami, Florida, (Apr. 1-4 2003). WFU-53.

Molnar, J.A., et al., "Improved skin graft adherence and vascularization of integra(R) using subatmospheric pressure—a laboratory study", Abstract printed in Burn Care & Rehabilitation, p. S111, Abstract No. 141; American Burn Meeting, 34th Annual Meeting, Chicago, IL, (Apr. 24-27 2002). WFU-51.

Morykwas, M.J., et al., "Negative pressure treatment of burned extremities", 65th Annual Scientific Meeting, American Society of Plastic and Reconstructive Surgeons, Dallas, TX, pp. 86-87; 1 sheet of abstract (Nov. 9-13, 1996). WFU-36.

Morykwas, M.J., et al., "The effect of V.A.C.(TM) therapy on the length of stay, total charges and average daily charge for patients assigned to DRG 263: analysis of 13 consecutive quarters", presented in part at the 28th Annual Conference of the Wound, Ostomy, and Continence Nurses Society, Seattle, WA, (15 sheets) (Jun. 15-19, 1996). WFU-52.

Park, C.A., et al., "Outpatient use of Integra® and subatmospheric pressure in the management of wound and burn reconstruction", J. Burn Care Rehabil., 26(2 suppl.):S113, Chicago, IL, (May 10-13, 2005). WFU-62.

Schneider, A.M., et al., "Muscle flap survival after complete venous occlusion by application of a negative pressure device", 66th Annual Meeting of the American Society of Plastic and Reconstructive Surgeons, San Francisco, CA, pp. 300-302; 2 sheets of abstract (Sep. 21-24, 1997). WFU-38.

Schneider, A.M., et al., "Treatment of brown recluse spider bite wounds by external application of sub-atmospheric pressure", 68th Annual Meeting of the American Society of Plastic and Reconstructive Surgeons, New Orleans, LA, p. 35; 1 sheet of abstract (Oct. 24-27, 1999). WFU-40.

Webb, L.X., "Use of negative pressure devices in highly contaminated, high energy wounds", Extremity War Injuries: State of the Art and Future Directions, AAOS/OTA Extremity War Injures Symposium, Jan. 24-27, 2006, [Abstract]. WFU-65.

Morykwas, M.J., "Basic Research and Animal Studies," Presentation at the European Topical Negative Pressure Meeting in Salsbury, England, (Jun. 2005). WFU-71.

Defranzo, A.J., et al., "Vacuum assisted closure of the abdominal wall", 73rd Annual Meeting, American Association of Plastic Surgeons, Philadelphia, PA (2004), 1 sheet of abstract. WFU-60.

Argenta, P.A., et al., "Vacuum-assisted closure in the treatment of complex gynecologic wound failures," Obstet. Gynecol., 99(3):497-501, (9 sheets) (Mar. 2002). NPL-018.

Azad, S., et al., "Topical negative pressure may help chronic wound healing," B.M.J., 324:1100 (1 sheet) (May 4, 2002). NPL-026.

Ballard, K., et al., "Developments in wound care for difficult to manage wounds," Br. J. Nurs., 9(7):405-8,410,412 (Apr. 13-26, 2000). NPL-030.

Ballard, K., et al., "Vacuum-assisted closure," Nurs. Times, 97(35):51-2 (5 sheets) Aug. 30—Sep. 5, 2001. NPL-031.

Ballard, K., et al., "Use of vacuum-assisted closure therapy following foot amputation," Br. J. Nurs., 10(15 Supplement):S6, 8, 11-12 (Aug. 2001). NPL-032.

Banwell, P.E., "Topical negative pressure therapy in wound care," J. Wound Care, 8(2):79-84 (Feb. 1999). NPL-034.

Bartels, C.G., et al., "The vacuum sealing technique. A new approach to cover soft tissue defects, used after the resection of a leiomyosarcoma", (English abstract on 2nd page and 1 page printout from PubMed); Hautarzt, 52 (7):653-7 (Jul. 2001). NPL-039.

Bauer, P., et al., "Possibilities of preliminary treatment of infected soft tissue defects by vacuum sealing and PVA foam", (English abstract on first page and 1 sheet PubMed abstract), Handchir. Mikrochir. Plast. Chir., 30(1):20-3 (Jan. 1998). NPL-040.

Baynham, S.A., et al., "Treating stage IV pressure ulcers with negative pressure therapy: a case report", Ostomy Wound Manage., 45(4):28-32, 34-35 (Apr. 1999). NPL-041.

Birchall, L, et al., "Developing a trust-wide centralised approach to the use of TNP", J. Wound Care, 11(8):311-4 (Sep. 2002). NPL-047.

Brody, G.S., "Biological creep", Plast. Reconstr. Surg., 92(6):1202-1203 (Nov. 1993). NPL-060.

Campton-Johnston, S., et al., "Infected wound management: advanced technologies, moisture-retentive dressings, and die-hard methods", Grit. Care Nurs. Q, 24(2):64-77 (Aug. 2001). NPL-068.

Chen, K.D., et al., "Mechanotransduction in response to shear stress", J. Biol. Chem., 274(26):18393-18400, (Jun. 25, 1999). NPL-081.

Clare, M.P., et al., "Experience with the vacuum assisted closure negative pressure technique in the treatment of non-healing diabetic and dysvascular wounds", Foot Ankle Int., 23(10):896-901 (Oct. 2002). NPL-084.

Claxton, M.J., et al., "Healing the diabetic wound and keeping it healed: modalities for the early 21st century", Curr. Diab. Rep., 2(6):510-8 (Dec. 2002). NPL-086.

Coggrave, M., et al., "Topical negative pressure for pressure ulcer management", Br. J. Nurs., 11(6 Suppl):S29-31, S33-34, S36 (Mar. 2002). NPL-089.

Collier, M., "Know how: Vacuum assisted closure (VAC)", Nurs. Times, 93(5):32-3 (Jan. 29-Feb. 4 1997). NPL-090.

Cooper, S.M., et al., "Topical negative pressure", Int. J. Dermatol., 39(12):896-8 (Dec. 2000). NPL-098.

Cozart, R.F., et al., "The use of controlled subatmospheric pressure to promote wound healing in preparation for split-thickness skin grafting in a fourth degree burn", Tenn. Med., 92(10):382-4 (Oct. 1999). NPL-103.

Cro, C., et al., "Vacuum assisted closure system in the management of enterocutaneous fistulae," Postgrad. Med. J., 78(925):364-5 (Nov. 2002). NPL-104.

De Filippo, R.E., et al., "Stretch and growth: the molecular and physiologic influences of tissue expansion", Plast. Reconstr. Surg., 109(7):2450-2462 (Jun. 2002). NPL-110.

Deva, A.K., et al., "Vacuum-assisted closure of a sacral pressure sore", J. Wound Care, 6(7):311-312, (Jul. 1997). NPL-114.

Dunford, C., "Hypergranulation tissue", J. Wound Care, 8(10):506-507 (Nov. 1999). NPL-123.

Dunford, C.E., "Treatment of a wound infection in a patient with mantle cell lymphoma", Br. J. Nurs., 10(16):1058, 1060, 1062, 1064-5 (Sep. 13-26, 2001). NPL-124.

Espensen, E.H., et al., "Use of subatmospheric (VAC) therapy to improve bioengineered tissue grafting in diabetic foot wounds", J. Am. Podiatr. Med. Assoc., 92(7):395-7 (Jul.-Aug. 2002). NPL-142.

Fleck, T.M., et al., "The vacuum-assisted closure system for the treatment of deep sternal wound infections after cardiac surgery", Ann. Thorac. Surg., 74(5):1596-600 (Nov. 2002). NPL-155.

Fleischmann, W., et al., "Vacuum assisted closure of wounds following dermatofasciotomy of the leg", Unfallchirurg., (English abstract on p. 284, and 1 sheet printout from PubMed); 99(4):283-7, (Apr. 1996). NPL-161.

Ford, C.N., et al., "Interim analysis of a prospective, randomized trial of vacuum-assisted closure versus the healthpoint system in the management of pressure ulcers", Ann. Plast. Surg., (11 sheets); 49(1):55-61 (Jul. 2002). NPL-163.

Gouttefangeas, C., et al., "Functional T lymphocytes infiltrate implanted polyvinyl alcohol foams during surgical wound closure therapy," Clin. Exp. Immunol., 124(3):398-405 (Jun. 2001). NPL-173.

Greer, S.E., et al., "Subatmospheric pressure dressing for saphenous vein donor-site complications," Ann. Thorac. Surg., (6 sheets); 71(3):1038-40 (Mar. 2001). NPL-176.

Hawkins-Bradley, B., et al., "Treatment of a nonhealing wound with hypergranulation tissue and rolled edges", J. Wound Ostomy Continence Nurs., 29(6):320-324 (Nov. 2002). NPL-187.

Harlan, J.W., "Treatment of open sternal wounds with the vacuum-assisted closure system: a safe, reliable method", Plast. Reconstruct. Surg., 109(2):710-12 (Feb. 2002). NPL-191.

Hartnett, S., "Heparin-induced thrombocytopenia as the cause of gluteus muscle necrosis: a case study describing the benefits of multidisiplinary physical and psychosocial interventions", Ostomy Wound Manage., 47(5):18-26 (May 2001). NPL-194.

Hersh, R.E., et al., "A technique for the treatment of sternal infections using the vacuum assisted closure™ device", Heart Surg. Forum, 4(3):211-15 (2001). NPL-202.

Ingber, D.E., "Mechanical signaling and the cellular response to extracellular matrix in angiogenesis and cardiovascular physiology", Circ. Res., 91:877-887 (Nov. 15, 2002). NPL-219.

Kalailieff, D., "Vacuum-assisted closure: wound care technology for the new millennium", Perspectives, 22(3):28-9 (Fall 1998). NPL-230.

Kercher, K.W., et al., "Successful salvage of infected PTFE mesh after ventral hernia repair", Ostomy Wound Manage., 48(10):40-5 (Oct. 2002). NPL-234.

Kiernan, M., "The process of granulation and its role in wound healing", Community Nurse, 5(5):47-48 (Jun. 1999). NPL-235.

Kloth, L.C., "5 questions-and answers-about negative pressure wound therapy", Adv. Skin Wound Care, 15(5):226, 228-9 (Sep.-Oct. 2002). NPL-237.

Kusel, C., "Use of V.A.C. (vacuum-assisted closure) therapy in general surgery: problem wounds deprived of air", Pflege Z., (and 1 sheet printout from PubMed); 55(6):408-412 (Jun. 2002). NPL-245.

Labler, L., et al., "Vacuum sealing of problem wounds", Swiss Surg., (English abstract on first page, 1 sheet printout from PubMed); 8(6):266-7 (2002). NPL-246.

Marston, W.A., et al., "The efficacy and safety of Dermagraft in improving the healing of chronic diabetic foot ulcers: results of a prospective randomized trial", Diabetes Care, 26(6) 10 pp., (Exhibit 271) (Jun. 1, 2003). NPL-267.

Mendez-Eastman, S., "New treatment for an old problem: negative-pressure wound therapy", Nurs., 32(5):58-64. (12 sheets) (May 2002). NPL-279.

Muller, G., "Vacuum dressing in septic wound treatment", Langenbecks Arch. Chir. Suppl. Kongressbd., (English abstract on p. 537, and 1 sheet printout from PubMed); 114:537-41 (1997). NPL-301.

Ramnarine, I.R., et al., "Vacuum-assisted closure in the paediatric patient with post-cardiotomy mediastinitis", Eur. J. Cardiothorac. Surg., 22:1029-31 (Dec. 2002). NPL-342.

Rollins, H., "Hypergranulation tissue at gastrostomy sites", J. Wound Care, 9(3):127-129 (Mar. 2000). NPL-346.

Schaum, K.D., "Medicare Part B negative pressure wound therapy pump policy. A partner for Medicare Part A PPS," Home Healthc. Nurse, 20(1):57-8 (Jan. 2002). NPL-358.

Shaer, W.D., "Inexpensive vacuum-assisted closure employing a conventional disposable closed-suction drainage system", Plast. Reconstr. Surg., 107(1):292-3 (Jan. 2001). NPL-365.

Saklani, a.P., et al., "Vacuum assisted closure system in the management of enterocutaneous fistula", Postgrad. Med. J., 78(925):699 (Nov. 2002). NPL-370.

Takei, T., et al., "Molecular basis for tissue expansion: clinical implications for the surgeon", Plast. Reconstr. Surg., 102(1):247-258 (Jul. 1998). NPL-395.

Tang, A.T.M., et al., "Vacuum-assisted closure to treat deep sternal wound infection following cardiac surgery", J. Wound Care, 9(5):229-30 (May 2000). NPL-397.

Nikkhah, C., et al., "Re: use of specialized bone screws for intermaxillary fixation", Ann. Plast. Surg., 47(1): 93, (Jul. 2001). NPL-413.

Voinchet, V., et al., "Vacuum assisted closure. Wound healing by negative pressure", Ann. Chir. Plast. Esthet., (English abstract on first page, and 1 sheet printout from PubMed); 41(5):583-9, (Oct. 1996). NPL-422.

Von Gossler, C.M., et al., "Rapid aggressive soft-tissue necrosis after beetle bite can be treated by radical necrectomy and vacuum suction-assisted closure", J. Cutan. Med. Surg., 4(4):219-222 (Oct. 2000). NPL-424.

Wilhelmi, B.J., et al., "Creep vs. stretch: a review of the viscoelastic properties of skin", Ann. Plast. Surg., 41 (2):215-219, (Aug. 1998). NPL-436.

Wiseman, J., et al., "Aesthetic aspects of neurofibromatosis reconstruction with the vacuum-assisted closure system", Aesth. Plast. Surg., 25:326-31 (Sep.-Oct. 2001). NPL-440.

Young, T., "Common problems in wound care: overgranulation", Br. J. Nursing, 4(3):169-170, (Feb. 9-22, 1995). NPL-451.

Ziegler, U.E., et al., "Skin substitutes in chronic wounds", Zentralbl. Chir., (English abstract on first page; 1 sheet printout from PubMed); 126 Suppl 1:71-4 (2001). NPL-454.

Stannard, J., "Complex orthopaedic wounds: prevention and treatment with negative pressure wound therapy", Orthop. Nurs., 23 Suppl 1:3-10 (10 sheets) (Mar.-Apr. 2004), presented at the 17th Annual Clinical Symposium on Advances in Skin & Wound Care, Dallas, TX (Sep. 23, 2002). NPL-588.

Patel, C.T.C., et al., "Vacuum-assisted wound closure: changing atmospheric pressure assists wound healing," AJN, 100:45-47 (2000). NPL-598.

Masters, J., "Reliable, inexpensive and simple suction dressings", Letters to the Editor, p. 267, labeled 1998. NPL-602.

Hazelbag, S., et al., "Cytokine profile of cervical cancer cells", Gynecol. Oncol., 83(2):235-243, (Nov. 2001). NPL-613.

Beitz, J.M., et al., "Abdominal wound with enterocutaneous fistula: a case study", J. Wound Ostomy Continence Nurs., 25(2):102-6, (Mar. 1998). NPL-614.

Baxandall, T., "Healing cavity wounds with negative pressure", Elderly Care, 9(1):20, 22 (Feb.-Mar. 1997) NPL-615.

McKinney, P.E., "Out-of-hospital and interhospital management of crotaline snakebite", Ann. Emerg. Med., 37 (2):168-174, (Feb. 2001). NPL-616.

Leroy, S.C., et al., "Severe penile erosion after use of a vacuum suction device for management of erectile dysfunction in a spinal cord injured patient. Case report", Paraplegia, 32(2):120-123 (Feb. 1994). NPL-617.

Banwell, P.E., et al., "Topical negative pressure (TNP): the evolution of a novel wound therapy," J. Wound Care, 12 (1):22-8 (Jan. 2003). NPL-035.

Cardozo, M., "A case study of holistic wound management in intensive care", Br. J. Nurs., 12(11 Suppl):S35-37, S40-42 (Jun. 2003). NPL-069.

Collier, M., "Topical negative pressure therapy", Nurs. Times, 99(5):54-5 (Feb. 4-10, 2003). NPL-091.

Domkowski, P.W., et al., "Evaluation of vacuum-assisted closure in the treatment of poststerotomy mediastinitis," J. Thorac. Cardiovasc. Surg., 126(2):386-90 (Aug. 2003). NPL-119.

Eginton, M.T., et al., "A prospective randomized evaluation of negative-pressure wound dressings for diabetic foot wounds", Ann. Vasc. Surg., 17(6):645-9 (2003). NPL-132.

Ferreira, M.C., et al., "The vacuum assisted closure of complex wounds: report of three cases", Rev. Hosp. Clin. Fac. Med. S. Paulo, 58(4):227-30 (2003). NPL-151.

Fisher, a., et al., "Vacuum assisted wound closure therapy", Issues Emerg. Health Technol., Issue 44, 6 pp. (Mar. 2003). NPL-154.

Hallberg, H., et al., "Vaginal construction with skin grafts and vacuum-assisted closure", Scancl. J. Plast. Reconstr. Surg. Hand Surg., 37(2):97-101 (2003). NPL-184.

Hess, C.L., et al., "A review of mechanical adjuncts in wound healing: hydrotherapy, ultrasound, negative pressure therapy, hyperbaric oxygen, and electrostimulation", Ann. Plast. Surg., 51(2):210-8 (Aug. 2003). NPL-204.

Hodzic, J., et al., "Vacuum sealing of extensive wound healing disorders after kidney transplantation," Urologe A., (6 sheets in German, English abstract on p. 2 and 1 sheet printout from PubMed); 42(8):1097-100 (Aug. 2003) (Epub Apr. 3, 2003). NPL-208.
Kaufman, M.W., et al., "Vacuum-assisted closure therapy: wound care and nursing implications", Dermatol. Nurs., 15 (4):317-20, 323-236 (Aug. 2003). NPL-232.
Luckraz, H., et al., "Vacuum-assisted closure as a treatment modality for infections after cardiac surgery", J. Thorac. Cardiovasc. Surg., 125(2):301-5 (Feb. 2003). NPL-260.
McGuinness, J.G., et al., "Vacuum-assisted closure of a complex pilonidal sinus", Dis. Colon Rectum, 46(2):274-6 (Feb. 2003). NPL-272.
Moran, S.G., et al., "Vacuum-assisted complex wound closure with elastic vessel loop augmentation: a novel technique", J. Wound Care, 12(6):212-3 (Jun. 2003). NPL-298.
Schipper, J., et al., "The preconditioning and prelamination of pedicled and free microvascular anastomised flaps with the technique of vacuum assisted closure", Laryngorhinootologie, (English abstract on first page, and 2 sheets printout from PubMed); 82(6):421-7, (Jun. 2003). NPL-364.
Shi, B., et al., "Effects of vacuum-assisted closure (VAC) on the expressions of MM-1, 2, 13 in human granulation wound", Zhonghua Zheng Xing Wai Ke Za Zhi, (English abstract on first page and 1 sheet printout from PubMed); 19 (4):279-81 (Jul. 2003). NPL-366.
Silver, F.H., et al., "Mechanobiology of force transduction in dermal tissue", Skin Res. Technol., 9(1):3-23 (Feb. 2003). NPL-372.
Silver, F.H., et al., "Mechanosensing and mechanochemical transduction: how is mechanical energy sensed and converted into chemical energy in an extracellular matrix?" Crit. Rev. Biomed. Eng., 31(4):255-331 (2003). NPL-373.
Skillman, J., et al., "Vacuum assisted closure (VAC) dressing for skin graft application following exenteration of the orbit", Orbit, 22(1):63-5 (Mar. 2003). NPL-375.
Song, D.H., et al., "Vacuum assisted closure for the treatment of sternal wounds: the bridge between debridement and definitive closure", Plast. Recontr. Surg., 111(1):92-7 (Jan. 2003). NPL-381.
Wanner, M.B., et al., "Vacuum-assisted wound closure for cheaper and more comfortable healing of pressure sores: a prospective study", Scand. J. Plast. Reconstruct. Surg. Hand Surg., 37(1):28-33 (2003). NPL-427.
Weaver, B. "The nursing needs of a patient with a complicated abdominal wound", Prof. Nurse, 18(5):269-73 (Jan. 2003). NPL-429.
Wongworawat, M.D., et al., "Negative pressure dressings as an alternative technique for the treatment of infected wounds", Clin. Orthop. Relat. Res., (414):45-8 (Sep. 2003). NPL-442.
Baker, E.A., et al., "Growth factor profiles in intraperitoneal drainage fluid following colorectal surgery: relationship to wound healing and surgery", Wound Rep. Reg., 11(4):261-267, (Jul.-Aug. 2003). NPL-612.
Request for Re-examination of U.S. Patent No. 5,645,081, control No. 90/008,692 requested Jun. 11, 2007.
Request for Re-examination of U.S. Patent No. 5,636,643, control No. 90/008,697 requested Jun. 11, 2007.
Request for Re-examination of U.S. Patent No. 7,198,046, control No. 90/008,711 requested Jun. 11, 2007.
Request for Re-examination of U.S. Patent No. 7,216,651, control No. 90/008,693 requested Jun. 11, 2007.
Request for Inter Partes Reexamination of U.S. Patent No. 7,216,651, requested May 30, 2008. IPRE-001.
Exhibits to Request for Inter Partes Reexamination of U.S. Patent No. 7,216,651, requested May 30, 2008. IPRE-002.
Bagautdinov, N.A., "Alternative method of external vacuum aspiration in the treatment of purulent soft tissue disease," Curr. Problems Contemporary Clin. Surg.: Interscholastic Collection, pp. 94-96, (6 sheets of English translation and certification dated May 30, 2008; four sheets of English translation, 6 sheets in Russian, and certification dated May 9, 2008; 1 sheet of English translation of alleged library index card, 1 sheet in Russian, and certification dated May, 7, 2008); I.N. Ulianov Chuvash State University, Cheboksary, (1986). NPL-690.
Zivadinovic, G., et al., "Vacuum therapy in the treatment of peripheral blood vessels," Conference Papers of the 5th Timok Medical Days, Majdanpek, No. 3-4, pp. 161-164, (5 sheets English translation; 5 sheets in Serbian, certification dated May 9, 2008) (1986). NPL-691.
Johnson, F.E., "An improved technique for skin graft placement using a suction drain", Surg. Gynecol. Obstet., 159 (6):584-585 (Dec. 1984). NPL-226.
Safronov, A.A., Dissertation Abstract, "Vacuum therapy of trophic ulcers of the lower leg with simultaneous autoplasty of the skin," (Central Scientific Research Institute of Traumatology and Orthopedics, Moscow, U.S.S.R.) (23 sheets English translation; 23 sheets in Russian; certification dated May 8, 2008; alleged index card(English translation; 1 sheet Russian; certification dated May 14, 2008), (1967). NPL-692.
Tribble, D.E., "An improved sump drain-irrigation device of simple construction," Arch. Surg., 105:511-513, (Sep. 1972). NPL-693.
Tennant, C.E., "The use of hyperemia in the postoperative treatment of lesions of the extremities and thorax," Jour. A.M.A., 64(19):1548-1549, (May 8, 1915). NPL-694.
Orgill, D.P., et al., "Microdeformational wound therapy—a new era in wound healing," Business Briefing: Global Surgery—Future Directions, pp. 22, 24-25 (2005). NPL-695.
"V.A.C.® Therapy Clinical Guidelines: A reference source for clinicians," KCI, The Clinical Advantage ® (Jul. 2007). NPL-696.
N A Bagautdinov, "Vanant of External Vacuum Aspiration in the Treatment of Purulent Diseases of Soft Tissue," in Current Problems of Modern Clinical Surgery Interdepartmental Collection, edited by V Ye Volkov et al (Chuvashia State University, Cheboksary, U S.S R 1986) pp. 94-96.
K.F. Jeter, T.E. Tintle, and M Chariker, "Managing Draining Wounds and Fistulae: New and Established Methods," in *Chronic Wound Care*, edited by D. Krasner (Health Management Publications, Inc., King of Prussia, PA 1990) pp. 240-246.
G. Živadinović, Ž. Dukić, Ž. Maksimovid, D. Radak, and P. Peška, "Vacuum Therapy in the Treatment of Peripheral Blood Vessels," *Timok Medical Journal* 11 (1986) 161-164.
F E. Johnson, "An Improved Technique for Skin Graft Placement Using a Suction Drain,"*Surgery, Gynecology, and Obstetrics* 159 (1984) 584-585.
A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U S S.R. 1967).
M Schein, R. Saadia, J R. Jamieson, and G.A.G. Decker, "The 'Sandwich Technique' in the Management of the Open Abdomen," British Journal of Surgery 73 (1986) 369-370.
D.E. Tribble, "An Improved Sump Drain-Irrigation Device of Simple Construction," *Archives of Surgery* 105 (1972) 511-513.
M J. Morykwas, L.C. Argenta, E.I. Shelton-Brown, and W. McGuirt, "Vacuum-Assisted Closure: A New Method for Wound Control and Treatment: Animal Studies and Basic Foundation,"*Annals of Plastic Surgery* 38 (1997) 553-562.
U.S. Appl. No. 07/792,001, Amendment and Reply under 37 C.F.R. § 1.111, mailed Apr. 29, 1996.
U.S. Appl. No. 09/863,234, Amendment and Reply under 37 C.F R. § 1.111, mailed Apr. 20, 2004.
In re U.S. Patent No. 7,216,651, Control No. 90/008,693, Reply and Request for Reconsideration under 37 C.F.R. § 1.111, filed Apr. 28, 2008, in the U S. Patent and Trademark Office.
*Kinetic Concepts, Inc.* v. *BlueSky Med. Corp.*, No. 2:07-CV-00188, Plaintiffs' Original Complaint.(E D. Tex. May 14, 2007).
*Kinetic Concepts, Inc.* v. *BlueSky Med. Group, Inc*, Nos. 2007-1340, -1341, -1342, Brief of Appellants, Medela AG and Medela, Inc. (Fed. Cir. May 23, 2007).
*Kinetic Concepts, Inc.* v. *BlueSky Med Group, Inc*, Nos. 2007-1340, -1341, -1342, Brief of Kinetic Concepts, Inc., KCI Licensing, Inc., KCI USA, Inc., and Wake Forest University Health Sciences (Fed. Cir. Mar 3, 2008).
*Kinetic Concepts, Inc.* v. *BlueSky Med. Group, Inc*, Nos. 2007-1340, -1341, -1342, Reply Brief of Appellants, Medela AG and Medela, Inc. (Fed Cir May 16, 2008).

Selections from *Kinetic Concepts, Inc.* v. *BlueSky Med. Corp*, No. SA-03-CA-0832, in the U S.District Court for the Western District of Texas.

D.P. Orgill, L.R. Bayer, J. Neuwalder, and R.C. Felter, "Microdeformational Wound Therapy—A New Era in Wound Healing," in *Global Surgery: Future Directions in Surgery* (Touch Briefings, London, U.K. 2005) pp. 22-25.

M J. Morykwas, B.J. Faler, D J Pearce, and L.C. Argenta, "Effects of Varying Levels of Subatmospheric Pressure on the Rate of Granulation Tissue Formation in Experimental Wounds in Swine," *Annals of Plastic Surgery* 47 (2001) 457-551.

V.A C Therapy Clinical Guidelines A Reference Source for Clinicians (KCI Licensing Inc., San Antonio, TX 2007).

C.E. Tennant, "The Use of Hyperemia in the Postoperative Treatment of Lesions of the Extremities and Thorax," *Journal of the American Medical Association* 64 (1915) 1548-1549.

Selections from W. Meyer and V. Schmieden, *Bier's Hyperemic Treatment in Surgery, Medicine, and the Specialties A Manual of Its Practical Application* (W.B. Saunders Co., Philadelphia, PA 1909) pp. 17-25, 44-64, 90-96, 167-170, and 210-211.

Declaration of Dr. Ian L. Gordon, M.D , Ph.D.

Declaration of Dr Kenneth R. Diller, Sc.D.

Request for Ex Parte Reexamination of U.S. Patent No. 5,645,081, requested Jun. 3, 2008. EPRE-001.

Exhibits to Request for Ex Parte Reexamination of U.S. Patent No. 5,645,081, requested Jun. 3, 2008. EPRE-002.

Bagautdinov, N.A., "Variant of external vacuum aspiration in the treatment of purulent diseases of soft tissues," Current Problems in Modern Clinical Surgery, Interdepartmental Collection, Cheboksary, (4 pages of English translation, 6 sheets in Russian, certification dated May 22, 2008, English translation of index card, 1 sheet Russian, certification dated May 7, 2008) (1986). NPL-697.

Chardak, W.M., et al., "Experimental studies on synthetic substitutes for skin and their use in the treatment of burns," Ann. Surg., 155(1):127-139, (Jan. 1962). NPL-698.

Fujimori, R., et al., "Sponge fixation method for treatment of early scars," Plast. & Reconst. Surg., 42(4):322-326, (Oct. 1968). NPL-699.

Kirk-Othmer, Encyclopedia of Chemical Technology, 2nd completely revised edition, vol. 14, pp. 227, John Wiley & Sons, Inc., (1967). NPL-700.

Meyer, W., et al., excerpts from "Bier's Hyperemic Treatment", W.B. Saunders and Co., (47 sheets) (1908). NPL-702.

N.A. Bagautdinov, "Variant of External Vacuum Aspiration in the Treatment of Purulent Diseases of Soft Tissue," in Current Problems of Modern Clinical Surgery: Interdepartmental Collection, edited by V.Ye. Volkov et al. (Chuvashia State University, Cheboksary, U.S.S. R. 1986) pp. 94-96.

G. Živadinović, V. Dukić, Ž. Maksimović, D. Radak, and P. Peška, "Vacuum Therapy in the Treatment of Peripheral Blood Vessels," *Timok Medical Journal* 11 (1986) 161-164.

Selections from W. Meyer and V. Schmieden, *Bier's Hyperemic Treatment in Surgery, Medicine, and the Specialties: A Manual of Its Practical Application* (W.B. Saunders Co., Philadelphia, PA 1909) pp. 17-25, 44-64, 90-96, 167-170, and 210-211.

W.M. Chardak, D.A. Brueske, A.P. Santomaurio, and G. Fazekas, "Experimental Studies on Synthetic Substitutes for Skin and Their Use in the Treatment of Burns,"*Annals of Surgery* 155 (1962) 127-139.

In re U.S. Patent No. 5 645,081, Control No. 90/008,692, Reply and Request for Reconsideration under 37 C.F.R. § 1.111, filed Apr. 28, 2008, in the U.S. Patent and Trademark Office.

*Kinetic Concepts, Inc.* v. *BlueSky Med. Corp.*, No. SA-03-CA-0832, Plaintiffs' Fourth Amended.Complaint (W.D. Tex. Jun. 30, 2005) ("Amended Complaint").

*Kinetic Concepts. Inc.* v. *BlueSky Med. Group, Inc.*, Nos. 2007-1340, -1341, -1342, Brief of Kinetic Concepts, Inc., KCI Licensing, Inc., KCI USA, Inc., and Wake Forest University Health Sciences (Fed. Cir. Mar. 3, 2008).

*Kinetic Concepts, Inc.* v. *BlueSky Med. Group, Inc.*, Nos. 2007-1340, -1341, -1342, Reply Brief of Appellants, Medela AG and Medela, Inc. (Fed. Cir. May 16, 2008).

Selections from *Kinetic Concepts, Inc.* v. *BlueSky Med. Corp.*, No. SA-03-CA-0832, in the U.S.District Court for the Western District of Texas.

M.J. Morykwas, B.J. Faler, D.J. Pearce, and L.C. Argenta, "Effects of Varying Levels of Subatmospheric Pressure on the Rate of Granulation Tissue Formation in Experimental Wounds in Swine," *Annals of Plastic Surgery* 47 (2001) 457-551.

V.A.C. Therapy Clinical Guidelines: A Reference Source for Clinicians (KCI Licensing Inc., San Antonio, TX 2007).

R. Fujimori, M. Hiramoto, and S. Qfuji, "Sponge Fixation Method for Treatment of Early Scars," Plastic & Reconstructive Surgery 47 (1968) 322-327.

*Kirk-Othmer Encyclopedia of Chemical Technology*, edited by A. Standen (John Wiley & Sons, Inc., 2$^{nd}$ ed., vol. 14 1967) p. 227.

Declaration of Dr. Ian L. Gordon, M.D., Ph.D.

Declaration of Dr. Kenneth R. Diller, Sc.D.

Request for Ex Parte Reexamination of U.S. Patent No. 5,636,643, requested Jun. 3, 2008. EPRE-003.

Exhibits to Request for Inter Partes Reexamination of U.S. Patent No. 5,636,643, requested Jun. 3, 2008. EPRE-002.

Westaby, S., et al., "A wound irrigation device," Lancet, pp. 503-504, (Sep. 2, 1978). NPL-701.

N.A. Bagautdinov, "Variant of External Vacuum Aspiration in the Treatment of Purulent Diseases of Soft Tissue," in Current Problems of Modern Clinical Surgery: Interdepartmental Collection, edited by V.Ye. Volkov et al. (Chuvashia State University, Cheboksary, U.S.S. R. 1986) pp. 9496.

F.E. Johnson, "An Improved Technique for Skin Graft Placement Using a Suction Drain," *Surgery, Gynecology, and Obstetrics* 159 (1984) 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967).

S. Westaby and W.G. Everett, "A Wound Irrigation Device," *The Lancet* 312 (1978) 503-504.

In re U.S. Patent No. 5,636.643, Control No. 90/008,697, Reply and Request for Reconsideration under 37 C.F.R. § 1.111, filed Apr. 28, 2008, in the U.S. Patent and Trademark Office.

*Kinetic Concepts, Inc.* v. *BlueSky Med. Corp.*, No. 5:03-CV-00832, Plaintiffs' Original Complaint (W.D. Tex. Aug. 28, 2003).

*Kinetic Concepts, Inc.* v. *BlueSky Med. Group, Inc.*, Nos. 2007-1340, -1341, -1342, Brief of Appellants,.Medela AG and Medela, Inc. (Fed. Cir. May 23, 2007).

*Kinetic Concepts, Inc.* v. *BlueSkv Med. Group, Inc.*, Nos. 2007-1340, -1341, 1342, Brief of Kinetic Concepts, Inc., KCI Licensing, Inc., KCI USA, Inc., and Wake Forest University Health Sciences (Fed. Cir. Mar. 3, 2008).

*Kinetic Concepts, Inc.* v. *BlueSkv Med. Group, Inc.*, Nos. 2007-1340, -1341, -1342, Reply Brief of Appellants, Medela AG and Medela, Inc. (Fed. Cir. May 16, 2008).

Selections from *Kinetic Concepts, Inc.* v. *BlueSky Med. Corp.*, No. SA-03-CA-0832, in the U.S. District Court for the Western District of Texas.

R. Fujimori, M. Hiramoto, and S. Ofuji, "Sponge Fixation Method for Treatment of Early Scars," *Plastic & Reconstructive Surgery* 47 (1968) 322-327.

Reexam of US 5,645,081, Reexam No. 90/008,692, "Decision granting reexamination" dated Sep. 4, 2007. RE-006.

Reexam of US 5,636,643, Reexam No. 90/008,697, "Decision sua sponte vacating ex parte reexamination filing date," dated Sep. 5, 2007. RE-005.

Reexam of US 7,198,046, Reexam No. 90/008,711, "Decision sua sponte vacating ex parte reexamination filing date," dated Sep. 5, 2007. RE-007.

Reexam of US 7,216,651, Reexam No. 90/008,693, "Decision sua sponte vacating ex parte reexamination filing date," dated Sep. 5, 2007. RE-008.

Reexam of US 7,216,651, Reexam No. 90/008,693, "Resubmission of reexamination request in response to decision sua sponte vacating ex parte reexamination filing date," "Explicit withdraw of documents and new listing confined to documents for which a discussion required by 37 CFR 1.510(b)(2) has been provided via the request papers," and "Information Disclosure Statement," dated Oct. 5, 2007. RE-009.

Reexam of US 7,198,046, Reexam No. 90/008,711, "Resubmission of reexamination request in response to decision sua sponte vacating ex parte reexamination filing date," "Explicit withdraw of documents and new listing confined to documents for which a discussion required by 37 CFR 1.510(b)(2) has been provided via the request papers," and "Information Disclosure Statement," dated Oct. 5, 2007. RE-010.

Reexam of US 5,636,643, Reexam No. 90/008,697, "Resubmission of reexamination request in response to decision sua sponte vacating ex parte reexamination filing date," "Explicit withdraw of documents and new listing confined to documents for which a discussion required by 37 CFR 1.510(b)(2) has been provided via the request papers," and "Information Disclosure Statement," dated Oct. 5, 2007. RE-011.

Morykwas, M.J., "Use of sub-atmospheric pressure to prevent adriamycin extravasation ulcers in a pig model", first presented at the 44th Annual Meeting of Plastic Surgery Research Council, Pittsburg, PA, (May 22-26, 1999). WFU-73.

"The Remington Report: Business and clinical strategies for home care executives", containing articles by J.A. Molnar, D.G. Armstrong, et al., and S. Mendez-Eastman; (Nov. / Dec. 2004). WFU-76.

*Wake Forest University Health Sciences, et al.* v. *Innovative Therapies, Inc.*, Case No. 1:08-cv-32 in the Middle District of North Carolina, Plaintiffs' Original Complaint and Request for Preliminary and Permanent Injunctive Relief, with Patent Form A0120, filed by Wake Forest University on Jan. 10, 2008. MDNC32-001.

EP 0 620 720 (DE 692 24 847) Nullity Action filed by Molnlycke Health Care AB at the German Federal Patent Court to nullify EP 0 620 720 (DE 692 24 847) (EP equivalent of US 5645081) and English translation, dated Mar. 10, 2008. MolnlyckeDEWH1-001.

Classification of features of Claim 1 of EP 0 620 720 B2 (EP equivalent of US 5645081) labeled as "Anlage MFP1" in German with English translation (attachment to Nullity Action filed by Molnlycke on Mar. 10, 2008). MolnlyckeDEWH1-002.

Thomas, S., "Wound management and dressings," cover sheet, preface, sheet labeled "Chapter 5" and pp. 36-39 (1990). MolnlyckeDEWH1-003.

EP 0 620 720 Revocation Proceeding filed by Molnlycke Health Care AB at the UK High Court of Justice Chancery Division, Patents Court, Royal Courts of Justice, to revoke EP 0 620 720 (EP equivalent of US 5645081), dated Mar. 14, 2008. MolnlyckeUKWH1-001.

U.S. Appl. No. 10/161,076—Applicants' response (Mar. 14, 2008).
U.S. Appl. No. 10/227,161—Applicants' response (Jan. 30, 2007).
U.S. Appl. No. 10/647,068—Applicants' response (Jan. 30, 2007).
U.S. Appl. No. 10/647,068—Official Action (Jan. 17, 2008).
Official Action issued by USPTO dated Dec. 19, 2007 in U.S. Appl. No. 10/227,161 (7 pages including cover sheet).
U.S. Appl. No. 10/161,076—Final official action (Jun. 20, 2008).

Conquest, A.M., et al., "Hemodynamic effects of the vacuum-assisted closure device on open mediastinal wounds,"J. Surg. Res., 115(2):209-13 (Dec. 2003). NPL-093.

Copson, D., "Topical negative pressure and necrotising fasciitis", Nurs. Stand., 18(6):71-2, 74, 76, 78, 80 (Oct. 22, 2003). NPL-100.

Demaria, R.G., et al., "Topical negative pressure therapy. A very useful new method to treat severe infected vascular approaches in the groin,"J. Cardiovascular Surg., 44(6):757-61 (Dec. 2003). NPL-112.

De Vooght, A., et al., "Vacuum-assisted closure for abdominal wound dehiscence with prosthesis exposure in hernia surgery,"Plast. Recontr. Surg., 112(4):1188-9 (Sep. 15, 2003). NPL-115.

Duxbury, M.S., et al., "Use of a vacuum assisted closure device in pilonidal disease," J. Wound Care, 12(9):355 (Oct. 2003). NPL-127.

Eldad, A., et al., "Vacuum—a novel method for treating chronic wounds", Harefuah, (English abstract on last 2 pp. and 1 sheet printout from PubMed); 142(12):834-6, 878, 877 (Dec. 2003). NPL-135.

Evans, D., et al., "Topical negative pressure for treating chronic wounds", Cochrane Database Syst. Rev., vol. (3), accession No. 00075320-100000000-01309 (2005). NPL-143.

Fuchs, U., et al., "Clinical outcome of patients with deep sternal wound infection managed by vacuum-assisted closure compared to conventional therapy with open packaging: a retrospective analysis", Ann. Thorac. Surg., 79:526-31 (2005). NPL-168.

Gustafsson, R.I., et al., "Deep sternal wound infection: a sternal-sparing technique with vacuum-assisted closure therapy"Ann. Thorac. Surg., 76(6):2048-53 (Dec. 2003). NPL-182.

Herscovici Jr., D., et al., "Vacuum-assisted wound closure (VAC therapy) for the management of patients with high-energy soft tissue injuries", J. Orthop. Trauma, 17(10):683-8 (Nov.-Dec. 2003). NPL-201.

Huang, J., et al., "Treatment of open fracture by vacuum sealing technique and internal fixation", Zhongguo Xiu Fu Chong Jian Wai Ke Za Zhi, (English abstract on first page and 2 sheets printout from PubMed); 17(6):456-8 (Nov. 2003). NPL-213.

Jones, E.G., et al., "Management of an ileostomy and mucous fistula located in a dehisced wound in a patient with morbid obesity", J. Wound Ostomy Continence Nurs., 30(6):351-356 (Nov. 2003). NPL-227.

Langley-Hawthorne, C., "Economics of negative pressure wound therapy", Ostomy Wound Manage., 50(4A suppl):35, 36, C3 (Apr. 2004). NPL-250.

Neubauer, G., et al., "The cost-effectiveness of topical negative pressure versus other wound-healing therapies", J. Wound Care, 12(10):392-3 (Nov. 2003). NPL-312.

Orgill, D.P., et al., "Functional reconstruction following electrical injury", Ann. N.Y. Acad. Sci., 888:96-104 (Oct. 30, 1999). NPL-321.

Salameh, J.R., et al., "Laparoscopic harvest of omental flaps for reconstruction of complex mediastinal wounds", JSLS, 7(4):317-22 (Oct.-Dec. 2003). NPL-352.

Shoufani, A., et al., "Vacuum assisted closure—a new method for wound control and treatment", Harefuah, (English abstract on last page; 1 sheet printout from PubMed); 142(12):837-40, 877 (Dec. 2003). NPL-367.

Shvartsman, H.S., et al., "Use of vacuum-assisted closure device in the treatment of recurrent Paget's disease of the vulva", Obstet. Gynecol., Supplement, 102(5, part 2):1163-6 (Nov. 2003). NPL-368.

Sibbald, R.G., et al., "A consensus report on the use of vacuum-assisted closure in chronic, difficult-to-heal wounds", Ostomy Wound Manage., 49(11):52-66 (Nov. 2003). NPL-369.

Wagner, S., et al., "Comparison of inflammatory and systemic sources of growth factors in acute and chronic human wounds", Wound Rep. Reg., 11:253-260 (Jul.-Aug. 2003). NPL-426.

Wild, T., "Consensus of the German and Austrian Societies for wound healing and wound management on vacuum closure and the VAC treatment unit", MMW Fortschr. Med., (English abstract on p. 100; 1 sheet printout from PubMed); 145 Suppl. 3:97-101 (Oct. 9, 2003). NPL-435.

Chen, S.Z., et al., "Effect of vacuum-assisted closure on the expression of proto-oncogenes and its significance during wound healing", Zhonghua Zheng Xing Wai Ke Za Zhi, (English abstract on first page, 2 sheets printout from PubMed); 21:197-200 (May 2005). NPL-456.

Immer, F.F., et al., "Deep sternal wound infection after cardiac surgery: modality of treatment and outcome", Ann. Thorac. Surg., 80(3):957-61 (Sep. 2005; available online Aug. 23, 2005). NPL-457.

Saltzman, C.L., "Salvage of diffuse ankle osteomyelitis by single-stage resection and circumferential frame compression arthrodesis", Iowa Orthop. J., 25:47-52 (2005). NPL-458.

Bogart, L., "A summary of posters presented at the symposium on Advanced Wound Care: 2003 and 2004", Ostomy Wound Manage., 51(4):88-91 (Apr. 2005). NPL-459.

Chen, S.Z., et al., "Effects of vacuum-assisted closure on wound microcirculation: an experimental study", Asian J. Surg., 28(3):211-7 (Jul. 2005). NPL-460.

Paul, J.C., "Vacuum assisted closure therapy: a must in plastic surgery", Plastic Surg. Nurs., 25(2):61-5 (Apr.—Jun. 2005). NPL-462.

Winter, D., "Perspectives on vacuum-assisted closure therapy in pilonidal sinus surgery", Dis. Colon Rectum, 48 (9):1829-30, (Sep. 2005). NPL-463.

Arca, M.J., et al., "Use of vacuum-assisted closure system in the management of complex wounds in the neonate", Pediatr. Surg. Int., 21(7):532-5, 8 sheets, (published online Jun. 17, 2005). NPL-464.

Adamkova, M., et al., "First experience with the use of vacuum assisted closure in the treatment of skin defects at the burn center", Acta. Chir. Plast., 47(1):24-7 (2005). NPL-465.

Venturi, M.L., et al., "Mechanisms and clinical applications of the vacuum-assisted closure (VAC) device: a review", Am. J. Clin. Dermatol., 6(3):185-94 (2005). NPL-466.

Noel, B., "Management of venous leg ulcers", Rev. Med. Suisse, (English abstract on first page, 1 sheet printout from PubMed); 1(16):1062-6, 1068 (Apr. 20, 2005). NPL-467.

Riccio M. et al., "Delayed microsurgical reconstruction of the extremities for complex soft-tissue injuries", Microsurgery, 25:272-83 (2005). NPL-468.

Sjogren, J., et al., "Clinical outcome after poststernotomy mediastinitis: vacuum-assisted closure versus conventional treatment", Ann. Thorac. Surg., 79(6):2049-55 (Jun. 2005). NPL-469.

Dainty, L.A., et al., "Novel techniques to improve split-thickness skin graft viability during vulvo-vaginal reconstruction", Gynecol. Oncol., 97(3):949-52 (Jun. 2005). NPL-470.

Clubley, L., et al., "Using negative pressure therapy for healing of a sternal wound", Nurs. Times, 101(16):44-6 (Apr. 19, 2005). NPL-471.

Caniano, D.A., et al., "Wound management with vacuum-assisted closure: experience in 51 pediatric patients", J. Pediatr. Surg., 40(1):128-32 (Jan. 2005). NPL-472.

Steenvoorde, P., et al., "Deep infection after ilioinguinal node dissection: vacuum-assisted closure therapy?"Low. Extern. Wounds, 3(4):223-226 (Dec. 2004). NPL-473.

Ryan, T.J., "Evans (1966) exchange and the skin in the light of vacuum-assisted closure, yoga, and maggots", Low. Extrem. Wounds, 3(3):121-2 (Sep. 2004). NPL-474.

Armstrong, D.G., et al., "Decreasing foot pressures while implementing topical negative pressure (vacuum-assisted closure) therapy", Low. Extrem. Wounds, 3(1):12-15 (Mar. 2004). NPL-475.

Wackenfors, A., et al., "Blood flow responses in the peristernal thoracic wall during vacuum-assisted closure therapy", Ann. Thorac. Surg., 79(5):1724-31 (May 2005). NPL-476.

Whelan, C., et al., "Mechanics of wound healing and importance of vacuum-assisted closure® in urology", J. Urol., 173:1463-70 (May 2005). NPL-477.

O'Connor, J., et al., "Vacuum-assisted closure for the treatment of complex chest wounds", Ann. Thorac. Surg., 79 (4):1196-200 (Apr. 2005). NPL-478.

Nugent, N., et al., "Vacuum-assisted closure—A management option for the burns patients with exposed bone", Burns, 31(3):390-393 (May 2005) (Epub Jan. 22, 2005). NPL-479.

Lambert, K.V., et al., "Vacuum assisted closure: a review of development and current applications", Eur. J. Vasc. Endovasc. Surg., 29(3):219-226 (Mar. 2005). NPL-480.

Smith, N., "The benefits of VAC Therapy in the management of pressure ulcers", Br. J. Nurs., 13(22):1359-60, 1362, 1364-65 (Dec. 9, 2004-Jan. 12, 2005). NPL-481.

White, R.A., et al., "Vacuum-assisted closure complicated by erosion and hemorrhage of the anterior tibial artery", J. Orthop. Trauma, 19(1):56-59 (Jan. 2005). NPL-482.

De Geus, H.R.H., et al., "Vacuum-assisted closure in the treatment of large skin defects due to necrotizing fasciitis", Intensive Care Med., 31(4): 601 (1 page) (Apr. 2005) (Epub Jan. 22, 2005). NPL-483.

Samson, D., et al., "Wound-healing technologies: low level laser and vacuum-assisted closure", Evid. Rep. Technol. Assess. (Summ.), (111):1-6, (Dec. 2004). NPL-484.

Gibson, K., "Vacuum-assisted closure", Am. J. Nurs., 104(12):16 (1 page) (Dec. 2004). NPL-485.

Polly Jr., D.W., et al., "Advanced medical care for soldiers injured in Iraq and Afghanistan", Minn. Med., 87(11):42-4 (Nov. 2004). NPL-486.

Stone, P.A., et al., "Vacuum-assisted fascial closure for patients with abdominal trauma", J. Trauma, 57:1082-6 (Nov. 2004). NPL-487.

Connolly, T.P., "Necrotizing surgical site infection after tension-free vaginal tape", Obstet. Gynecol., 104(6):1275-6 (4 pages) (Dec. 2004). NPL-488.

Wackenfors, A., et al., "Effects of vacuum-assisted closure therapy on inguinal wound edge microvascular blood flow", Wound Rep. Regen., 12(6):600-6 (Nov.-Dec. 2004). NPL-489.

Schaffzin, D.M., et al., "Vacuum-assisted closure of complex perineal wounds", Dis. Colon Rectum, 47:1745-8 (Oct. 2004) (Published online Aug. 24, 2004). NPL-490.

Yousaf, M., et al., "Use of vacuum-assisted closure for healing of a persistent perineal sinus following panproctocolectomy: report of a case", Dis. Colon Rectum, 47(8):1403-8 (Aug. 2004) (Published online Aug. 12, 2004). NPL-491.

Fox, A., et al., "An unusual complication of vacuum assisted closure in the treatment of a pressure ulcer", J. Wound Care, 13(8):344-5 (Sep. 2004). NPL-492.

Saxena, V., et al., "Vacuum-assisted closure: microdeformations of wounds and cell proliferation", Plast. Reconstruct. Surg., 114(5):1086-96 (Oct. 2004). NPL-493.

Scholl, L., et al., "Sternal osteomyelitis: use of vacuum-assisted closure device as an adjunct to definitive closure with sternectomy and muscle flap reconstruction", J. Card. Surg., 19(5):453-61 (Sep.-Oct. 2004). NPL-495.

Ohye, R.G., et al. "Primary closure for postoperative mediastinitis in children", J. Thorac. Cardiovasc. Surg., 128 (3):480-6 (Sep. 2004). NPL-496.

Tang, S.Y., et al., "Influence of vacuum-assisted closure technique on expression of Bcl-2 and NGF/NGFmRNA during wound healing", Zhonghua Zheng Xing Wai Ke Za Zhi, (English abstract on first page 1 sheet printout from PubMed); 20(2):139-42 (Mar. 2004). NPL-497.

Armstrong, D.G., et al., "Guidelines regarding negative wound therapy (NPWT) in the diabetic foot", Ostomy Wound Manage., 50(4B Suppl.):3S-27S (Apr. 2004). NPL-498.

Shilt, J.S., et al., "Role of vacuum-assisted closure in the treatment of pediatric lawnmower injuries", J. Pediatr. Orthop., 24(5):482-7 (Sep.-Oct. 2004). NPL-499.

Antony, S., et al., "A retrospective study: clinical experience using vacuum-assisted closure in the treatment of wounds", J. Natl. Med. Assoc., 96(8):1073-7 (Aug. 2004). NPL-500.

Steenvoorde, P., et al., "Vacuum-assisted closure therapy and oral anticoagulation therapy", Plast. Reconstruct. Surg., 113(7):2220-1 (Jun. 2004). NPL-501.

Oczenski, W., et al., "Vacuum-assisted closure for the treatment of cervical and mediastinal necrotizing fasciitis", J. Cardiothorac. Vasc. Anesth., 18(3):336-8 (Jun. 2004). NPL-502.

Carson, S.N., et al., "Vacuum-assisted closure used for healing chronic wounds and skin grafts in the lower extremities", Ostomy Wound Manage., 50(3):52-8 (9 sheets) (Mar. 2004). NPL-503.

Marathe, U.S., et al., "Use of the vacuum-assisted closure device in enhancing closure of a massive skull defect", Laryngoscope, 114(6):961-4 (8 sheets) (Jun. 2004). NPL-504.

Schintler, M.V., et al., "The impact of the VAC-treatment for locally advanced malignancy of the scalp", Zentralbl. Chir., (English abstract on first page, 1 sheet printout from PubMed); 129 Suppl 1:S141-S146 (May 2004). NPL-505.

Querings, K., et al., "Revitalization of a gluteal abscesses with V.A.C. therapy (vacuum assisted closure)", Zentralbl. Chir, (English abstract on first page, 1 sheet printout from PubMed); 129 Suppl 1:S138-S140 (May 2004). NPL-506.

Kall, S., et al., "Influence of foam- and tubing material of the vacuum assisted closure device (V.A.C.) on the concentration of transforming growth factor beta 1 in wound fluid", Zentralbl. Chir., (English abstract on first page, 2 sheets printout from PubMed); 129 Suppl 1: S113-S115 (May 2004). NPL-507.

Mang, R., et al., "Vacuum therapy in a pre- and postsurgical ulcera crurum", Zentralbl. Chir., (English abstract on first page, 1 sheet printout from PubMed); 129 Suppl 1:S101-S103 (May 2004). NPL-508.

Steiert, A.E., et al., "The V.A.C. system (vacuum assisted closure) as bridging between primary osteosynthesis in conjunction with functional reconstructed of soft tissue—open fractures type 2 and type 3", Zentralbl. Chir., (English abstract on first page, 2 sheets printout from PubMed); 129 Suppl 1:S98-100 (May 2004). NPL-509.

Karl, T., et al., "Indications and results of V.A.C. therapy treatments in vascular surgery—state of the art in the treatment of chronic wounds", Zentralbl. Chir., (English abstract on first page, 1 sheet printout from PubMed); 129 Suppl 1:S74-S79 (May 2004). NPL-510.

Ferbert, T., et al., "Treatment of soft tissue defects on hand and forearm with vacuum assisted closure", Zentralbl. Chir, (English abstract on first page, 1 sheet printout from PubMed); 129 Suppl 1:857-858 (May 2004). NPL-511.

Halama, D., et al., "Intraoral application of vacuum-assisted closure in the treatment of an extended mandibular keratocyst", Zentralbl. Chir., (English abstract on first page, 1 sheet printout from PubMed); 129 Suppl 1:S53-S56 (May 2004). NPL-512.

Fleck, T., et al., "Early treatment of sternal wound infections with vacuum assisted closure therapy reduces involvement of the mediastinum and further diminishes the need of plastic reconstructive surgery", Zentralbl. Chir., (1 sheet printout from PubMed); 129 Suppl 1:S35-S37 (May 2004). NPL-513.

Kutschka, I., et al., "Vacuum assisted closure therapy improves early postoperative lung function in patients with large sternal wounds", Zentralbl. Chir., (English abstract on first page, 1 sheet printout from PubMed); 129 Suppl 1: S33-S34 (May 2004). NPL-514.

Labler, L., et al., "New application of V.A.C. (vacuum assisted closure) in the abdominal cavity in case of open abdomen therapy", Zentralbl. Chir., (English abstract on first page, 2 sheets printout from PubMed); 129 Suppl 1:S14-S19 (May 2004). NPL-515.

Wild, T., et al., "Consensus of the German and Austrian Societies for Wound Healing and Wound Management on vacuum closure and the V.A.C. treatment unit", Zentralbl. Chir., (English abstract on first page, 2 sheet printout from PubMed and 1 sheet of erratum); 129 Suppl 1:S7-S11 (May 2004). NPL-516.

Weed, T., et al., "Quantifying bacterial bioburden during negative pressure wound therapy. Does the wound VAC enhance bacterial clearance?"Ann. Plast. Surg., 52(3):276-80 (Mar. 2004). NPL-517.

Mustoe, T., "Understanding chronic wounds: a unifying hypothesis on their pathogenesis and implications for therapy", Am. J. Surg., 187(5A):65S-70S (May 2004). NPL-518.

Tzeng, Y.J., et al., "Using vacuum-assisted closure (VAC) in wound management", Hu Li Za Zhi, (English abstract on last page, 1 sheet printout from PubMed); 51(2):79-83 (Apr. 2004). NPL-519.

Quah, H.M., et al., "Vacuum-assisted closure in the management of the open abdomen: a report of a case and initial experiences", J. Tissue Viability, 14(2):59-62 (Apr. 2004). NPL-521.

Emohare, O., et al., "Vacuum-assisted closure use in calciphylaxis", J. Burn Care Rehabil., 25(2):161-4 (Mar.-Apr. 2004). NPL-522.

Wackenfors, A., et al., "The effect of vacuum-assisted closure therapy on the pig femoral artery vasomotor responses", Wound Repair Regen., 12(2):244-51 (Mar.-Apr. 2004). NPL-523.

Sjogren, J., et al., "Vacuum-assisted closure therapy in mediastinitis after heart transplantation", J. Heart Lung Transplant., 23(4):506-7 (Apr. 2004). NPL-524.

Miller, Q., et al., "Effect of subatmospheric pressure on the acute healing wound", Curr. Surg., 61(2):205-8 (Mar.-Apr. 2004). NPL-525.

Penn, E., et al., "Management of a dehisced abdominal wound with VAC therapy", Br. J. Nurs., 13(4):194, 196, 198-201 (Feb. 26-Mar. 10, 2004). NPL-526.

Moues, C.M., et al., "Bacterial load in relation to vacuum-assisted closure wound therapy: a prospective randomized trial", Wound Repair Regen., 12(1):11-7 (Jan.-Feb. 2004). NPL-527.

Schimp, V.L., et al., "Vacuum-assisted closure in the treatment of gynecologic oncology wound failures", Gynecol. Oncol., 92(2):586-91 (Feb. 2004). NPL-528.

Aru, G.M., et al., "Limitations on the role of vacuum-assisted closure in cardiac surgery", J. Thorac. Cardiovasc. Surg., 127(2):604-5 (Feb. 2004). NPL-529.

Bihariesingh, V.J., et al., "Plastic solutions for orthopaedic problems", Arch. Orthop. Trauma. Surg., 124(2):73-6 (Mar. 2004) (Epub Jan. 17, 2004). NPL-530.

Kaplan, M., "Managing the open abdomen", Ostomy Wound Manage., 50(1A suppl):C2, 1-8, and 1 sheet of quiz (Jan. 2004). NPL-531.

Colwell, A.S., et al., "Management of early groin vascular bypass graft infections with sartorius and rectus femoris flaps", Ann. Plast. Surg., 52(1):49-53 (Jan. 2004). NPL-532.

Evidence Report/Technology Assessment, No. 111, "Wound healing technologies: low-level laser and vacuum-assisted closure", prepared for Agency for Healthcare Research and Quality by the Blue Cross and Blue Shield Association Technology Evaluation Center Evidence-based Practice Center, under Contract No. 290-02-0026, AHRQ Publications Clearinghouse, Available Dec. 2004. NPL-533.

Wolvos, T., "Wound instillation—the next step in negative pressure wound therapy. Lessons learned from initial experiences", Ostomy Wound Manage., 50(11):56-58, 60-66 (Nov. 2004). NPL-534.

Bluman, E.M., et al., "Subatmospheric pressure-induced compartment syndrome of the entire upper extremity. A case report", J. Bone Joint Surg. (Am.), 86-A(9):2041-4 (Sep. 2004). NPL-535.

Kamolz, L.P., et al., "Use of subatmospheric pressure therapy to prevent burn wound progression in human: first experiences", Burns, 30(3):253-8 (May 2004) (Available online Mar. 16, 2004). NPL-536.

Jones, S.M., et al., "Advances in wound healing: topical negative pressure therapy", Postgrad. Med. J., 81 (956):353-7 (Jun. 2005). NPL-537.

Stone, P., et al., "Bolster versus negative pressure wound therapy for securing split-thickness skin grafts in trauma patients", Wounds, 16(7):219-23 (5 sheets) (2004) (Posted Aug. 4, 2004). NPL-589.

Wolvos, T., "Wound instillation with negative pressure wound therapy", Ostomy Wound Manage., 51(2A suppl):21S-26S (Feb. 2005) NPL-590.

Jeter, K., "Closed suction wound drainage system", JWOCN, 31(2):51 (1 sheet) (Mar.-Apr. 2004). NPL-591.

Agarwal, J.P., et al., "Vacuum-assisted closure for sternal wounds: a first-line therapeutic management approach", Plast. Reconstr. Surg., 116(4):1035-1040 (Sep. 15, 2005). NPL-592.

Sjogren, J., et al., "The impact of vacuum-assisted closure on long-term survival after post-sternotomy mediastinitis", Ann. Thorac. Surg., 80(4):1270-5, (Oct. 2005). NPL-593.

Mendez-Eastman, S., "New advances in wound therapy", printout from Wounds1.com; 7 sheets (Apr. 15, 2005). NPL-594.

"Promoting wound healing", Nurses-Digest, 2(3), 6 sheets, Mar. 2005. NPL-595.

Roylance, L., "Nancy Sujeta, Amanda Clark,"Dome, vol. 55, Mar. 2004, 2 sheets of website printout www.hopkinsmedicine.orgidome/0405/feature4.cfm. NPL-596.

Agarwal, J.P., et al., "Vacuum assisted closure™ for sternal wounds: a first line therapeutic management", ASPS, Plastic Surgery 2004, Philadelphia, PA, abstract (2 sheets) (Wednesday Oct. 13, 2004). NPL-597.

Gomoll, A.H., et al., "Incisional vacuum-assisted closure therapy", J. Orthop. Trauma, 20(10):705-709, (Nov.-Dec. 2006). NPL-599.

Leininger, B.E., et al., "Experience with wound VAC and delayed primary closure of contaminated soft tissue injuries in Iraq", J. Trauma, 61(5):1207-1211 (Nov. 2006). NPL-600.

Gupta, S., ed., "Differentiating negative pressure wound therapy devices: an illustrative case series", Wounds, 19(1 suppl):1-9, (Jan. 2007). NPL-603.

Korasiewicz, L.M., "Abdominal Wound With a Fistula and Large Amount of Drainage Status After Incarcerated Hernia Repair", Journal of Wound, Ostomy & Continence Nursing. 31(3):150-153, (May-Jun. 2004). NPL-610.

Guntinas-Lichius, O., et al., "The role of growth factors for disease and therapy in diseases of the head and neck", DNA and Cell Biol., 22(9):593-606, (Sep. 2003). NPL-611.

Goldman, R., "Growth factors and chronic wound healing: past, present, and future", Adv. Skin Wound Care, 17 (1):24-35, (Jan.-Feb. 2004). NPL-618.

Malli, S., "Keep a close eye on vacuum-assisted wound closure", Nursing, 35(7):25 (Jul. 2005). NPL-622.

Lynch, J.B., et al., "Vacuum-assisted closure therapy: a new treatment option for recurrent pilonidal sinus disease. Report of three cases", Dis. Colon Rectum, 47(6):929-32 (Jun. 2004) (Published online May 4, 2004). NPL-520.

MX: Business Strategies for Medical Technology Executives, (Mar. / Apr. 2005). NPL-624.

Niezgoda, J.A., "Incorporating negative pressure therapy into the management strategy for pressure ulcers", Ostomy Wound Manage., 50(11A suppl.):5S-8S, (Nov. 2004). NPL-625.

Banwell, Re., "Topical negative pressure therapy: advances in burn wound management", Ostomy Wound Manage., 50(11A suppl.):9S-14S, (Nov. 2004). NPL-630.

Kaplan, M., "Negative pressure wound therapy in the management of abdominal compartment syndrome", Ostomy Wound Manage., 50(11A suppl):20S-25S, (Nov. 2004). NPL-626.

Gupta, S., et al., "The perioperative use of negative pressure wound therapy in skin grafting", Ostomy Wound Manage., 50(11A suppl.):26S-28S, (Nov. 2004). NPL-627.

Schoemann, M.B., et al., "Treating surgical wound dehiscence with negative pressure dressings", Ostomy Wound Manage., 51(2A suppl.):15S-20S, (Feb. 2005). NPL-628.

Bookout, K., et al., "Case studies of an infant, a toddler, and an adolescent treated with a negative rpessure wound treatment system", J. Wound OstomyContinence Nurs., 31(4):184-192, (8 pp.) (Jul. / Aug. 2004). NPL-629.

Borkowski, S., "G tube care: managing hypergranulation tissue", Nursing, 35(8):24 (Aug. 2005). NPL-639.

Machen, M. S., "Management of traumatic war wounds using vacuum-assisted closure dressings in an austere environment," Army Medical Department J., pp. 17-23, (Jan.-Mar. 2007). NPL-688.

Peck, M.A., et al., "The complete management of extremity vascular injury in a local population: a wartime report from the 332nd Expeditionary Medical Group/Air Force Theater Hospital, Balad Air Base, Iraq," J. Vasc. Surg., pp. 1-9, (2007), (Presented at the Plenary Session of the Eastern Vascular Society's Twentieth Annual Meeting, Washington D. C., Sep. 30, 2006). NPL-689.

Giovannini, U.M., et al., "Topical negative therapy and vacuum assisted closure. New strategies and devices in surgical reconstruction", Minerva Chir., 60(3):191-4 (Jun. 2005). NPL-461.

Moues, C.M., et al., "An economic evaluation of the use of TNP on full-thickness wounds", J. Wound Care, 14 (5):224-7 (May 2005). NPL-538.

Lee, S.S., et al., "Management of intractable sternal wound infections with topical negative pressure dressing", J. Card. Surg., 20(3):218-22 (May-Jun. 2005). NPL-539.

Jethwa, P., et al., "Using topical negative pressure therapy to resolve wound failure following perineal resection", J. Wound Care, 14(4):166-7 (Apr. 2005). NPL-540.

Banwell, P.E., et al., "Topical negative pressure therapy: mechanisms and indications", Int. Wound J., 1(2):95 (15 pages) (Jun. 2004). NPL-541.

Melano, E., et al., "The effects of Panafil when using topical negative pressure to heal an infected sternal wound,"J. Wound Care, 13(10):425-6 (Nov. 2004). NPL-542.

Morton, N., "Use of topical negative pressure therapy in postoperative dehisced or infected wounds", J. Wound Care, 13(8):346-8 (Sep. 2004). NPL-543.

Moisidis, E., et al., "A prospective, blinded, randomized, controlled clinical trial of topical negative pressure use in skin grafting", Plast. Reconstr. Surg., 114(4):917-22 (7 sheets) (Sep. 15, 2004). NPL-544.

Tachi, M., et al., "Topical negative pressure using a drainage pouch without foam dressing for the treatment of undetermined pressure ulcers", Ann. Plast. Surg., 53(4):338-42 (7 sheets) (Oct. 2004). NPL-545.

Jones, S.M., et al., "Complications of topical negative pressure therapy in small-diameter wounds", Plast. Reconstr. Surg., 114(3):815-817 (5 sheets) (Sep. 1, 2004). NPL-546.

Loree, S., et al., "Is vacuum assisted closure a valid technique for debriding chronic leg ulcers?" J. Wound Care, 13 (6):249-52 (Jun. 2004). NPL-547.

Vogt, P.M., et al., "Several aspects of foam materials and their possible interactions with the wound surface in the vacuum therapy", Zentralbl. Chir., (English abstract on first page, 1 sheet printout from PubMed); 129 Suppl 1:S92-S94 (May 2004). NPL-548.

Haslik, W., et al., "The use of subatmospheric pressure to prevent burn wound progression: first experiences in burn wound treatment", Zentralbl. Chir., (English abstract on first page, and 1 sheet printout from PubMed); 129 Suppl. 1: S62-63 (May 2004). NPL-549.

Steenvoorde, P., et al., "Combining topical negative pressure and a Bogota bag for managing a difficult laparostomy", J. Wound Care, 13(4):142-3 (Apr. 2004). NPL-550.

Pullen, R., "Treatment of pressure sores in elderly patients", Z. Genrontol. Geriatr., (English abstract on first page, 1 sheet printout from PubMed); 37(2):92-9 (Apr. 2004). NPL-551.

Gottrup, F., "Optimizing wound treatment through health care structuring and professional education", Wound Repair Regen., 12(2):129-33 (Mar.-Apr. 2004). NPL-552.

(Anon.) "New best practice guidelines for managing pressure ulcers with negative pressure wound therapy published", Home Healthcare Nurse, 23(7):469 (one sheet) (Jul. 2005). NPL-553.

Stechmiller, J.K., et al., "Effect of negative pressure wound therapy on the expression of TNF-alpha, IL-1beta, MMP-2, MMP-3, and TIMP-1 in wound fluids of adults with pressure ulcers", Wound Repair Regen., 13(2):A16 (Mar.-Apr. 2005). NPL-554.

Snyder, R.J., "Negative pressure wound therapy (NPWT)/ vacuum-assisted closure® (VAC®) as an adjunct in the treatment of pyoderma gangrenosum", Wound repair and regeneration, 13:A29 (Mar. 2005). NPL-555.

Armstrong, D.G., et al., "Negative pressure wound therapy in treatment of diabetic foot wounds: a marriage of modalities", Ostomy Wound Manage., 50(4A suppl):9-12 (Apr. 2004). NPL-556.

Armstrong, D.G., et al., "Plantar pressure changes using novel negative pressure wound therapy technique", J. Am. Podiatr. Med. Assoc., 94(5):456-60 (Sep.-Oct. 2004). NPL-557.

Baharestani, M.M., "Negative pressure wound therapy: An examination of cost-effectiveness", Ostomy Wound Manage., 50(11A suppl):29S-33S (Nov. 2004). NPL-558.

Bernstein, B.H., et al., "Combination of subatmospheric pressure dressing and gravity feed antibiotic instillation in the treatment of post-surgical diabetic foot wounds: a case series,"parts 1 and 2, Wounds, 17(2):37-48 (23 sheets) (Feb. 2005). NPL-559.

Datiashvili, R.O., et al., "Negative pressure dressings: An alternative to free tissue transfers?" Wounds, 17 (8):206-212 (Aug. 2005). NPL-560.

De Leon, J., "Negative pressure wound therapy in pressure ulcer management", Ostomy Wound Manage., 51(2A suppl):3S-8S (Feb. 2005). NPL-561.

Dobke, M.K., et al., "A novel approach to acute infection of the glenohumeral joint following rotator cuff repair—a case series", Wounds, 17(6):137-40 (6 sheets) (Jun. 2005). NPL-562.

Dunbar, A., et al., "Addressing the pain: Silicone net dressings as an adjunct with negative pressure wound therapy", Ostomy Wound Manage., 51(4):18-20 (4 sheets) (Apr. 2005). NPL-563.

Etoz, A., et al., "The use of negative pressure wound therapy on diabetic foot ulcers: a preliminary controlled trial", Wounds, 16(8):264-9 (Aug. 2004). NPL-564.

Fife, C.E., et al., "Healing dehisced surgical wounds with negative pressure wound therapy", Ostomy Wound Manage., 50(4A suppl):28-31 (Apr. 2004). NPL-565.

Geller, S.M., et al., "Ulceration of pyoderma gangrenosum treated with negative pressure wound therapy", J. Am. Podiatr. Med. Assoc., 95(2):171-4 (Mar.-Apr. 2005). NPL-566.

Gray, M., et al., "Is negative pressure wound therapy effective for the management of chronic wounds?"J. Wound Ostomy Continence Nurs., 31(3):101-5 (May-Jun. 2004). NPL-567.

Gupta, S., et al., "A literature review of negative pressure wound therapy", Ostomy Wound Manage., 50(11A suppl):2S-4S (Nov. 2004). NPL-568.

Gupta, S., et al., "The perioperative use of negative pressure wound therapy in skin grafting", Ostomy Wound Mangage., 50(4A suppl):32-4 (Apr. 2004). NPL-569.

Gupta, S., et al., "Guidelines for managing pressure ulcers with negative pressure wound therapy", Adv. Skin Wound Care, 17(Suppl 2):1-16 (Nov.-Dec. 2004). NPL-570.

Huljev, D., et al., "Necrotizing fasciitis of the abdominal wall as a post-surgical complication: a case report", Wounds, 17(7):169-77 (10 sheets) (2005) (Posted Aug. 11, 2005). NPL-571.

Kaplan, M., "Negative pressure wound therapy in the management of abdominal compartment syndrome", Ostomy Wound Manage., 51(2A suppl):29S-35S (Feb. 2005). NPL-572.

Mendez-Eastman, S., "Determining the appropriateness of negative pressure wound therapy for pressure ulcers", Ostomy Wound Manage., 50(4A suppl):13-16 (Apr. 2004). NPL-573.

Mendez-Eastman, S., "Using negative-pressure for positive results", Nursing, 35(5):48-50 (May 2005). NPL-574.

Miller, M.S., et al., "Negative pressure wound therapy: 'A rose by any other name'", Ostomy Wound Manage., 51 (3):44-9 (11 sheets) (Mar. 2005). NPL-575.

Niezgoda, J.A., et al., "The economic value of negative pressure wound therapy", Ostomy Wound Manage., 51 (2A suppl):44S-47S (Feb. 2005). NPL-576.

Niezgoda, J.A., "Combining negative pressure wound therapy with other wound management modalities", Ostomy Wound Manage., 51(2A suppl):S36-8 (Feb. 2005). NPL-577.

Orgill, D.P., et al., "Guidelines for treatment of complex chest wounds with negative pressure wound therapy", Supplement B to Wounds: a Compendium of Clinical Research and Practice, (24 sheets) (Dec. 2004). NPL-578.

Orgill, D.P., "Utilizing negative pressure wound therapy on open chest/sternotomy wounds", Ostomy Wound Manage., 50(11A suppl):15S-17S (Nov. 2004). NPL-579.

Orgill, D.P., "Advancing the treatment options of chest wounds with negative pressure wound therapy", Ostomy Wound Manage., 51(2A suppl):39S-43S (Feb. 2005). NPL-580.

Page, J.C., et al., "Retrospective analysis of negative pressure wound therapy in open foot wounds with significant soft tissue defects", Adv. Skin Wound Care, 17(7):354, 356, 358-60, 362-64 (Sep. 2004). NPL-581.

Page, J.C., et al., "Negative pressure wound therapy in open foot wounds with significant soft tissue defects", Ostomy Wound Manage., 51(2A suppl):9S-14S (Feb. 2005); excerpted from page, J.C., et al., "Retrospective analysis of negative pressure wound therapy in open foot wounds with significant soft tissue defects", Adv. Skin & Wound Care, 17(7):354-364, (2004). NPL-582.

Pattison, P.S., et al., "Case report: Using dual therapies—Negative pressure wound therapy and modified silicone gel liner—to treat a limb postamputation and dehiscence", Wounds, 17(8):233-40 (11 sheets) (Aug. 2005). NPL-583.

Ratliff, C.R., "Negative-pressure wound therapy. Adjunct relief for chronic wounds", Adv. Nurs. Pract., 12(7):47-9 (3 sheets) (Jul. 2004) (Issue date: Jul. 1, 2004). NPL-584.

Sarsam, S.E., et al., "Management of wound complications from cesarean delivery,"Obstet. Gynecol. Surv., 60 (7):462-73 (Jul. 2005). NPL-585.

Schaum, K.D., "Payment perspective: Negative pressure wound therapy pumps and ostomy supplies", Ostomy Wound Manage., 51(3):20-22 (2 sheets) (Mar. 2005). NPL-586.

Simman, R., et al., "A comparative histological study of skin graft take with tie-over bolster dressing versus negative pressure wound therapy in a pig model: a preliminary study [brief communication]", Wounds, 16(2):76-80 (7 sheets) (Feb. 2004). NPL-587.

PCT/US07184962—Written Opinion and International Search Report P04232W00—ISR (Apr. 18, 2008).

Reexam of US 5,636,643, Reexam No. 90/008,697, Final office action, mailed Jul. 24, 2008. RE-027.

Inter Partes Reexam of US 7,216,651, Order granting request for reexamination, mailed Aug. 4, 2008. IPRE-003.

PCT/US08/50584—Written Opinion and International Search Report (Jul. 25, 2008).

Inter Partes Reexam of US 7,216,651, Reexam No. 95/001,048, Order granting request for reexamination, mailed Aug. 4, 2008. IPRE-003.

Ex Parte Reexam of US 5645081, Reexam No. 90/010,186, Order granting request for reexamination, mailed Aug. 28, 2008. EPRE-005.

Ex Parte Reexam of US 5636643, Reexam No. 90/010,187, Order granting request for reexamination, mailed Aug. 28, 2008. EPRE-006.

Reexam of US 7,198,046, Reexam No. 90/008,711, Notice of Intent to Issue Ex Parte Reexamination Certificate, mailed Aug. 20, 2008. RE-028.

U.S. Appl. No. 10/227,161—Final Official action (Sep. 10, 2008).

Reexam of US 5,636,643, Reexam No. 90/008,697, Response to final office action, mailed Sep. 24, 2008. RE-029.

Peacock, Jr., E.E., Wound Repair, 3d edition, W.B. Saunders Company pp. 12-14, pp. 38-51, Chapter 6 Repair of skin wounds, (1984). NPL-721.

Spartanburg Regional Medical Center Operative reports, 35 sheets, dated 1989. NPL-747.

Johnson, F.E., "Expanded use of suction drains," pp. 469 and 1 sheet of drawings (allegedly dated 1985). NPL-748.

Brossy, J.-J., "Foam elastomer dressings in surgery," SA Medical Journal, 59:559-560, (Apr. 1981). NPL-749.

Groves, A.R., et al., "Silastic foam dressing: an appraisal," Annals of the Royal College of Surgeons of England, vol. 67, pp. 117-118 and additional page, (1985). NPL-750.

Harding, K.G., et al., "Silastic foam dressing for skin graft donor sites—a preliminary report," Br. J. Plast. Surg., 33:418-421, (1980). NPL-751.

Malone, W.D., "Wound dressing adherence: a clinical comparitive study," Archives of Emergency Medicine, 4:101-105, (1987). NPL-752.

Moblvac II advertising materials, 4 sheets, allegedly dated 1984. NPL-753.

Bucknall, T.E. ed., et al., "Wound healing for surgeons," Introduction, Chapter 1 the healing wound, Chapter 2 Wound strength, Chapter 3 Factors affecting healing, Chapter 4 Sutures and dressings, Chapter 5 Clinical trials, Chapter 6 Skin healing and burns, and Chapter 7 the abdominal wall, (1984). NPL-754.

Brubacher, L.L., "To heal a draining wound," RN, 45(3):30-36 (Mar. 1982). NPL-755.

Dahlin, P.A., et al., "Cerebrospinal fluid leak because of pressure sore fistula in a quadriplegic," Spine, 12(1):72-75, (1987). NPL-756.

Downie, P.A., ed., Cash's textbook of medical conditions for physiotherapists, Chapter 1 Inflammation and healing, Chapter 2 Oedema, Chapter 19 Skin conditions, Chapter 20 Burns, B. Lippincott Co., (1979). NPL-757.

Ersh, Z. Ya., "Use of polyurethane foam for cleaning of purulent cavities and wounds,"I.I. Grekov J. Of Surg., 133 (9):134-135 and additional sheets (10 sheets in English and 5 sheets in Russian) (1984). NPL-758.

Fasol, R, et al., "The foil vacuum dressing for the treatment of infected skin defects," Acta Chir. Austriaca 116-118, (2 sheets English and 3 sheets German) (1976). NPL-759.

"Heparin use may reduce restenosis risk," AORN J., 46(3):456, (Sep. 1987). NPL-760.

Gruendemann, B.J., et al., Alexander's Care of the patient in surgery, 8th ed., C.V. Mosby Co., pp. 138-139 (1987). NPL-761.

Kirk-Othmer Encyclopedia of chemical technology, 3d ed., vol. 8, pp. 201-203 (1979). NPL-762.

Kostyuchenok, B.M., et al., "Vacuum treatment of purulent wounds," Soviet Medicine, pp. 18-21, (4 sheets English, 4 sheets Russian, with English abstract on last page), (1984). NPL-763.

Kuzin, M.I., et al., "Method of vacuum treatment of wounds," Wounds and Wound Infection, pp. 348-350, (2 sheets) (1981). NPL-764.

Kuzin, M.I., ed., et al., "Vacuum treatment of a purulent wound," Wounds and Wound Infection, Handbook for Physicians, 2nd revised and supplemented ed., pp. 243-246, (3 sheets) (1990). NPL-765.

Tranchell, H.G., et al., Circulatory Ulcers a Physicial Approach, John Wright & Sons Ltd., Bristol, Foreword, I. Ulcers: a comparison, II. The ulcer, pp. 44-47, and 54-55, (1960). NPL-766.

Parish, L.C., et al., "The infected decubitus ulcer," Int. J. Dermatol., 28:643-647 (Dec. 1989). NPL-768.

Davydov, Y.A., et al., "Device and method for vacuum therapy of purulent lactation mastites," Khirurgiya, (4):131-132, (Apr. 1988). DV15.

Davidov, Y.A., et al., "Justifying the usage of forced early secondary sutures in treatment of purulent wounds by the vacuum therapy," Vestnik Chirugia 126-129, (2 sheets in English and 3 sheets in Russian) (Mar. 1990). DV16.

Davydov, Y.A., et al., "Pathogenic mechanisms of the effect of vacuum therapy on the course of the wound process," Khirurgiya, 6:42-47 (7 sheets English and 8 sheets Russian, with English abstract on pp. 46-47) (1990). DV17.

Davydov, Y.A., et al., "Bacteriological and cytological evaluation of vacuum therapy of purulent wounds", Vestnik khirurgii, 10:48-52, (5 sheets English, 5 sheets Russian, English abstract on pp. 52) (Received 1987). DV18.

Davydov, Y.A., et al., "Vacuum therapy in the treatment of purulent lactation mastitis," pp. 66-70 (5 sheets English, 5 sheets Russian, English abstract on pp. 70) (Received 1986). DV19.

Davydov, Y.A., et al., "Vacuum therapy in the treatment of acute purulent diseases of soft tissues and purulent wounds", Vest. Khir. 141(9):43-46 (6 sheets English, 6 sheets Russian, English abstract on pp. 46) (1988). DV20.

EP 0 620 720 (DE 692 24 847), English translation of the Decision of the Federal Patent Court dated Mar. 17, 2009, full translation by Vossius & Partner. DENA-WH1-019.

Excerpts from Biers Hyperemic Treatment, pp. 17-25, 44-46, 90-96, 167-170, 210-211 (1909). NPL-767.

EP 03756228.7 Supplemental European Search Report—(May 26, 2009).

*Wfu & KCI v. S&N*, VID 143, (Regarding AU 674837) Federal Court of Australia, Order by Judge Ryan, including reasons for judgment, dated Jun. 15, 2009. AU143-001.

Solovev, V.A., "Treatment and prevention of suture failures after gastric resection," Dissertation abstract, with alleged index card, S.M. Kirov Gorky State Medical Institute, Gorky, U.S.S.R., (Exhibit I of Third party comments) (1988). NPL-769.

Solovev, V.A., "The method of treatment of immature external fistulas in the upper gastrointestinal tract," S.M. Kirov Gorky State Medical Institute, Gorky, U.S.S.R., (Exhibit J of Third party comments) (1987). NPL-770.

EP 0 620 720 (De 692 24 847), Decision of Federal Patent Court, in German with English translation, dated Mar. 17, 2009. DENA-WH1-018.

Demorest, R.L., "New standards in water vapour permeability testing," British Plastics & Rubber, 3 sheets, (handwritten label on first sheet shows "Exhibit TT"), (May 1995). NPL-789.

3M™ Inzisionsfolien—Produktubersicht, by 3M Medica, 6 annotated sheets. NPL-772.

Application for rationalization proposal, proposal entitled "Variant for vacuum treatment of purulent wounds," (4 sheets in English, 4 sheets in Russian, certificate of translation dated May 8, 2009), proposal allegedly executed Dec. 25, 1985 (Bagautdinov III). NPL-773.

Buschbaum, H.J., ed., et al., Strategies in Gynecologic Surgery, pp. 203, Springer-Verlag, NY, (1986). NPL-774.

Flynn, J-B. McC., et al., Technological Foundations in Nursing, pp. 506-507, Appleton & Lange, Norwalk, CT, (1990). NPL-775.

GOMCO Mobile constant and intermittent model 6030 & 6031, Operation, Maintenance and Service Manual, with annotations, 21 sheets, (Jan. 1987). NPL-776.

Kahlson, G., et al., "Wound healing as dependent on rate of histamine formation," The Lancet, pp. 230-234, (Jul. 30, 1960). NPL-777.

Karev, I.D., et al., "Foam drainage system for treating purulent wounds," pp. 87-88, (2 sheets English translation, 2 sheets Russian and certifcation of translation dated Apr. 6, 2009) (allegedly dated 1986). NPL-778.

Kozier, B., et al., Techniques in Clinical Nursing, 3d ed., pp. 559-560, pp. 603-605, Addison-Wesley Publishing Company, Inc., Health Sciences, Redwood City, CA, (1989). NPL-779.

McLean, W. C., "The role of closed wound negative pressure suction in radial surgical procedures of the head and neck," The Laryngoscope, 74(1)70-94, (Jan. 1964). NPL-780.

Norton, B.A., et al., Skills for Professional Nursing Practice: communication, physical appraisal, and clinical techniques, pp. 298-302, pp. 328-329, Appleton-Century-Crofts, Norwalk, CT (1986). NPL-781.

Bagautdinov, N.A., Report on Practical Application entitled "Variant of vacuum treatment of purulent wounds," Kazan Municipal Hospital No. 8, (1 sheet in English, 1 sheet in Russian and certificate of translation dated May 8, 2009) (allegedly dated Dec. 24, 1985). (Practical Report I) NPL-782.

Kuznetsov, V.A. et al., Report on Practical Application entitled "Method of vacuum-sorption treatment of purulent wounds," Kazan Municipal Hospital No. 8, (1 sheet in English, 1 sheet in Russian and certificate of translation dated Apr. 28, 2009) (allegedly dated May 19, 1986). (Practical Report II) NPL-783.

Bagautdinov, N.A., Report on Practical Application entitled "Method of vacuum treatment of open purulent wounds," Medical-Sanitary Ward of the Arzamas Instrument Plant, (1 sheet in English, 1 sheet in Russian and certificate of translation dated Apr. 27, 2009) (allegedly dated 1986).(Practical Report III) NPL-784.

Roth, B., et al., "Ubersichtsarbeit: Indication for suction-rinse drainage and hygienic certainty in drainages," GMS Krankenhaushyg. Interdiszip, 1(1):Doc27 (7 sheets in German with English abstract on first sheet) (2006). NPL-785.

Schneider, F.R., Handbook for the Orthopaedic Assistant, 2nd ed., pp. 185, The C.V. Mosby Company, St. Louis, (1976). NPL-786.

Thomas, S., Wound Management and Dressings, Chapter 4: Semipermeable film dressings (continued onto pp. 26-34), Chapter 5: Foam dressings (continued onto pp. 36-42), and pp. 166, The Pharmaceutical Press, London, (1990). NPL-787.

Witkowski, J.A., et al., "Synthetic dressings: wound healing in the 80's," (5 sheets), Hospital Therapy, (Nov. 1986). NPL-788.

Thomas, S., "Wound Management and Dressings," The Pharmaceutical Press, London, 223 sheets, (1990). NPL-793.

Wood, R.A.B., et al., "A new method for treatment of open granulating wounds," Surgical Dressings in the Hospital Environment, T.D. Turner, ed., et al., Surgical Dressings Research Unit, Welsh School of Pharmacy, Uwist, Cardiff, 8 sheets, (1975). NPL-797.

Turner, T.D., ed., et al., Advances in Wound Management, including "The role of foam dressings in wound management" by S. Thomas, "Clinical aspects of Synthaderme" by T. Martin, et al., "Lyofoam®— Used in the treatment of leg ulcers" by J. Creevy, and "Clinical experience of Silastic® foam dressing," by K.G. Harding; John Wiley & Sons, 17 sheets, (Proceedings dated Mar. 20-21, 1985) (1986). NPL-798.

Kuznetsov, V.A., et al., Report on Practical Application entitled "Method of vacuum-sorption treatment of purulent wounds," Kazan Municipal Hospital No. 8, (1 sheet in English, 1 sheet in Russian and certificate of translation dated Apr. 28, 2009), (allegedly dated May 19, 1986). NPL-800.

*KCI et al.* v. *Blue Sky Medical Group et al.*, Case No. 2007-1340, -1341, -1342, Federal Circuit Decision dated Feb. 2, 2009. CAFC1340-008.

*WFU* v. *S&N* (UK) Case No. HC08 C03563, Approved judgment dated Jul. 31, 2009. SNUK-030.

British Pharmacopoeia, vol. II, pp. 903-940, London (1980). NPL-801.

British Pharmacopoeia 1980, pp. A81, 542, 546-549, with annotations, London—Addendum (1986). NPL-802.

*KCI et al.* v. *Blue Sky Medical Group et al.*, Petition for a Writ of Certiorari before the Supreme Court of the United States, filed by Medela (Appeal from Case No. 2007-1340, -1341, -1342 before the CAFC), dated Aug. 13, 2009. CAFC1340-011.

*Medela* v. *KCI*, et al., U.S.Supreme Court Case No. 09-198 (Appeal from Case No. 2007-1340, -1341, -1342 before the CAFC) Denial of writ of certiorari, dated Nov. 16, 2009. CAFC1340-012.

Thomas, S., "Pain and wound management," Community Outlook, pp. 11-13, 15 and one extra sheet, (Jul. 1989). NPL-803.

Livshits, V.S., "Polymer dressings for wounds and burns (review)," All-Union Scientific-Research Institute for Medical Polymers, Moscow, pp. 515-522, (allegedly published in Pharmaceutical Chemical Journal, 22(7):790-798, translated from Russian (allegedly dated Jul. 1988)), Plenum Publishing Corp., (1989). NPL-804.

Calne, S., ed., Position Document: Pain at wound dressings changes, pp. 1-17 and 3 additional sheets, supported by Molnlycke Health Care, (allegedly dated 2002). NPL-805.

Skover, G., et al., "45: New Technologies: An Overview," Chronic Wound Care, pp. 425-430 (allegedly dated 1990). NPL-806.

2 sheets of documents, the citation is alleged to be: David JA, Wound Management: A Comprehensive Guide to Dressing and Healing, pp. 51-51 (allegedly dated 1986). NPL-807.

Thomas, S., "Selecting dresssings," Community Outlook, vol. 6, 4 sheets, (Jun. 1991). NPL-796.

1 sheet document, the citation is alleged to be: David J., Extract from Practical Nursing Handbook: Wound Management: a Comprehensive Guide to Dressing and Healing, pp. 166-167, (allegedly dated 1986). NPL-799.

EP 0 620 720 (DE 692 24 847), Ref. No. K113179N11, Appeal Reasoning and Exhibit BK1 as filed with the Federal Supreme Court, filed by Wake Forest Sep. 4, 2009. DENA-WH1-020.

*Mölnlycke Health Care AB* v. *Wake Forest University* (UK), Case No: HC 08 C00744, Approved udgment, dated Aug. 28, 2009. MolnlyckeUKWH1-002.

Dunphy, J.E., ed., et al., "Current Surgical Diagnosis & Treatment" 5th ed., pp. 946-951, with 5 additional sheets, Lange Medical Publications, Los Altos, CA (1981). NPL-809.

Wagner, D.R., et al., "Combined parenteral and enteral nutrition in severe trauma," Nutrition in Clinical Practice, 7:113-116 with additional sheet, (1992). NPL-810.

Krizek, T.J., et al., "The use of prophylactic antibacterials in plastic surgery: A 1980s update," Plast. Reconstr. Surg., 76(6): 953-962, (Dec. 1985). NPL-811.
Orgill, D.P., et al., "The mechanisms of action of vacuum assisted closure: More to learn," Surgery, 146(1):40-51, (Jul. 2009). WFU-98.
Defranzo, A., et al., "4: Vacuum-assisted closure in extremity trauma," in Soft Tissue Surgery, S.L. Moran et al., p. 49-60 and additional sheet, Lippincott Williams & Wilkins (Pub. Apr. 1, 2008). WFU-96.
Stoeckel, W.T., et al., "30: Vacuum assisted devices for difficult wounds of the face and neck," Essential Tissue Healing of the Face and Neck, p. 399-408, and additional sheet, Hom, et al., (Pub. Jan. 28, 2009). WFU-95.
Proto, Massachusetts General Hospital Dispaches from the Frontiers of Medicine, 2 sheets, (Winter 2006). NPL-813.
Powell, E.T., "The role of negative pressure wound therapy with reticulated open cell foam in the treatment of war wounds," J. Orthop. Trauma, vol. 22(10) Supp.: S138-S141, (Nov./Dec. 2008). NPL-814.
"Negative pressure wound therapy devices," Technology assessment report; Agency for Healthcare Research and Quality, with annotations, website dated May 26, 2009, printed Jun. 26, 2009 and Jun. 28, 2009. NPL-812.
Thomas, S., "Atraumatic dressings," World Wide Wounds, sponsored by Molnylcke Health Care, 11 sheets, published Jan. 2003, website printout dated Jun. 29, 2009. NPL-808.
Marks, M.W., et al., "Principles & Applications of Vacuum Assisted Closure (Vac)" Plastic Surgery Secrets, 2nd ed., Mosby Elsevier, (2010). WFU-97.
Bonnamy, C., et al., "Use of the vacuum-assisted closure system for the treatment of perineal gangrene involving the abdominal wall", Ann. Chir., (English abstract on first page and 1 sheet PubMed abstract) 125(10):982-4 (Dec. 2000). NPL-054.
Kumar, A.R., "Standard wound coverage techniques for extremity war injury," J. Am. Acad. Orthop. Surg., 14:S62-S65, (2006). NPL-827.
McGee, M.P., et al., "Swelling and pressure-volume relationships in the dermis measured by osmotic-stress technique," Am. J. Physiol. Regul. Integr. Comp. Physiol., 296:R1907-R1913, (Mar. 25, 2009). WFU-90.
Morykwas, M., "Vacuum assisted closure," 91 sheets of slides. WFU-91, (Mar. 2006).
Morykwas, M., et al., "El uso de la plantilla de regeneracion integra en la cirugia reconstructiva," 121 sheets of slides. WFU-92, (2001).
Morykwas, M., et al., "Aplicaciones de tratamientos con presion sub-atmosferica en el cuidado de quemaduras," 140 sheets of slides. WFU-93, (2000).
Argenta, A., et al., "Deformation of superficial and deep abdominal tissues with application of a controlled vacuum", 1 sheet. WFU-94, (2000).
Bagautdinov, N.A., "Variant of external vacuum aspiration in the treatment of purulent diseases of soft tissues," Current Problems in Modern Clinical Surgery, Interdepartmental Collection, Cheboksary, pp. 94-96, and library card, in English and Russian, (KCI_Con00220647-59) (1986). NPL-841.
Kuznetsov, V.A., et al., "Vacuum and vacuum-sorption treatment of open purulent wounds," II All-Union Conference "Wounds and Wound Infections" Moscow, pp. 91-92, with library card and table of contents, in English and Russian, (KCI_Con00220660-89) (1986). NPL-842.
Williams, R.S., "A simple technique for successful primary closure after excision of pilonidal sinus disease," Ann. R. Coll. Surg. England, 72:313-315, (only 2 sheets provided), (1990). NPL-820.
Gray, A.J., et al., "Small bowel perforation following vacuum suction drainage," J. R. Coll. Surg. Edinb. 30(5):324-5 and additional sheet, (Oct. 1985). NPL-819.
Kumar, A.R., "Standard wound coverage techniques for extremity war injury," J. Am. Acad. Orthop. Surg., 14:S62- S65, (2006). NPL-827.
Helgeson, M.D., et al., "Bioartificial dermal substitute: A preliminary report on its use for the management of complex combat-related soft tissue wounds," J. Orthop. Trauma, 21(6):394-399, (Jul. 2007). NPL-828.
Ingari, J.V., et al., "Civilian and detainee orthopaedic surgical care at an air force theater hosptial," Tech. Hand Upper Extr. Surg., 11(2):130-134, (2007). NPL-829.
Covey, D.C., "Combat orthopaedics: A view from the trenches," J. Am. Acad. Orthop. Surg., 14:S10-S17, (2006). NPL-830.

Andersen, R.C., et al., "Definitive treatment of combat casulties at military medical centers," J. Am. Acad. Orthop. Surg., 14:S24-S31, (2006). NPL-831.
Wagner, D. R., et al., "Bioelectrical impedance as a discriminator of pressure ulcer risk," Adv. Wound Care, 9 (2):30-37, (1996). NPL-834.
Mulder, G.D., et al., "Prospective randomized study of the efficacy of hydrogel, hydrocolloid, and saline solution-moistened dressings on the management of pressure ulcers," Wound Rep. Reg., 1:213-218, (1993). NPL-836.
Tintle, T.E., et al., "Early experience with a calcium alginate dressing," Ostomy/Wound Management, pp. 74-81, (May/Jun. 1990). NPL-839.
Jeter, K.F., et al., "Comprehensive wound management with a starch-based copolymer dressing," J. Enterostom. Ther., 13(6):217-225, (Nov.-Dec. 1986). NPL-840.
Winter, G.D., "Formation of the scab and the rate of epithelization of superficial wounds in the skin of the young domestic pig," Nature, No. 4812, p. 293-294 (Jan. 20, 1962). NPL-816.
Robson, M.C., et al., "Bacterial quantification of open wounds," Military Medicine, pp. 19-24, (Jan. 1969). NPL-817.
Jackson, D.M., "The diagnosis of the depth of burning," Br. J. Surgery, 40(164):588-596 and 7 additional sheets, (May 1953). NPL-818.
Morykwas, M.J., "38: Vacuum-assisted closure of wounds" in "Wound Healing," A. Falabella et al., eds., Taylor & Francis, NY, pp. 503-515, (2005). WFU-77.
DeFranzo, A.J., et al., "Vacuum assisted closure for the treatment of abdominal wounds," Clin. Plast. Surg. 33(2): 213-224 (Apr. 2006). WFU-78.
Defranzo, A.J., et al., "Vacuum-assisted closure for defects of the abdominal wall," Plast. Reconstr. Surg., 121 (3):832-839, (Mar. 2008). WFU-79.
Park, C.A., et al., "Breast asymmetry: presentation of a giant fibroadenoma," Breast J., 12(5):451-461, (2006). WFU-80.
Zannis, J., et al., "Comparison of fasciotomy wound closures using traditional dressing changes and the Vacuum-Assisted Closure device," Ann. Plast. Surg., 62(4):407-409, (Apr. 2009). WFU-81.
Thompson, J.T., et al., "Outcome analysis of helmet therapy for positional plagiocephaly using a three-dimensional surface scanning laser," J. Craniofasc. Surg., 20(2):362-365, (Mar. 2009). WFU-82.
Argenta, L.C., et al., "Advances in hemangioma evaluation and treatment," J. Craniofac. Surg., 17(4):748-755 (Jul. 2006). WFU-83.
Plikaitis, C.M., et al, "Neurocutaneous melanosis: clinical presentations," J. Craniofac. Surg., 16(5):921-925 (Sep. 2005). WFU-84.
David, L.R., et al., "Proboscis lateralis: a rare craniofacial anomaly, reconstruction, and long-term evaluation," J. Craniofac. Surg., 19(4):1107-1113, (Jul. 2008). WFU-85.
Sanger, C., et al., "Dynamic spring mediated cranioplasty in an experimental model with resorbable foot plates," J. Craniofac. Surg., 18(1):54-59, (Jan. 2007). WFU-87.
Morykwas, M.J., et al., "Vacuum-assisted closure: state of basic research and physiologic foundation," Plast. Reconstr. Surg., 117(7) (Suppl): 121S-126S, (Jun. 2006). WFU-88.
Hill, C.A., et al. "Superior sternal cleft repair using autologous rib grafts in an infant with complex congenital heart disease," Ann. Thorac. Surg., 84:673-4, (2007). WFU-89.
McGee, M.P., et al., "Swelling and pressure-vol. relationships in the dermis measured by osmotic-stress technique," Am. J. Physiol. Regul. Integr. Comp. Physiol., 296:R1907-R1913, (Mar. 25, 2009). WFU-90.
Morykwas, M., "Vacuum assisted closure," 91 sheets of slides. WFU-91.
Morykwas, M., et al., "El use de la plantilla de regeneracion integra en la cirugia reconstructiva," 121 sheets of slides. WFU-92.
Morykwas, M., et al., "Aplicaciones de tratamientos con presion sub-atmosferica en el cuidado de quemaduras," 140 sheets of slides. WFU-93.
Argenta, A., et al., "Deformation of superficial and deep abdominal tissues with application of a controlled vacuum", 1 sheet. WFU-94.

* cited by examiner

APPARATUS AND METHOD FOR WOUND TREATMENT EMPLOYING PERIODIC SUB-ATMOSPHERIC PRESSURE

FIELD OF THE INVENTION

The present invention relates generally to an apparatus and method for treating tissue using time-varying sub-atmospheric pressure, and more particularly, but not exclusively, to an apparatus and method for treating wounds using sinusoidally varying sub-atmospheric pressure.

BACKGROUND OF THE INVENTION

The field of medicine has long been concerned with healing tissue damage such as that which may be brought on by disease or trauma. Numerous treatment modalities have been introduced over the years, including more recently the development of wound treatment through the use of negative (or sub-atmospheric) pressure, pioneered by Drs. Argenta and Morykwas and set forth in U.S. Pat. Nos. 5,645,081 and 5,636,643, as well as US Published Application Nos. 2003/0225347, 2004/0039391, and 2004/0122434, the contents of which are incorporated herein by reference. Although the application of either continuous or intermittent negative pressure wound therapy as specified in the aforementioned patents demonstrates an increased rate of healing as compared to traditional methods, an enduring goal of medical treatment remains healing of wounded or damaged tissue as quickly as possible. Consequently, there remains a need in the field of medicine for devices and techniques that expedite the healing of injured or wounded tissue.

SUMMARY OF THE INVENTION

In accordance with the present invention, a tissue treatment apparatus is provided for treating tissue by application of time-varying sub-atmospheric pressure. Tissues that may be treated by the apparatus of the present invention include wounded tissues, such as those present in chronic wounds, acute wounds, open wounds, closed wounds, and so forth, for example. Such wounds may be created by a variety of causes, such as trauma, disease, thermal injury (e.g., burns or hypothermia), surgical complications, and other factors.

In order to administer sub-atmospheric pressure treatment to damaged or wounded tissue, the apparatus of the present invention includes a cover adapted to cover a wound and adapted to maintain sub-atmospheric pressure at the site of the wound. The cover may be conveniently provided in the form of a flexible sheet or drape capable of conforming to tissue surrounding the wound. Alternatively, the cover may be provided in the form of a rigid or semi-rigid structure capable of supporting itself out of contact with the tissue to be treated. The apparatus also includes a seal configured to seal the cover to tissue surrounding the wound, so that the sealed cover provides an enclosure above the wound in which sub-atmospheric pressure may be maintained. Optionally, the apparatus may include a screen disposed between the cover and the wound for promoting the distribution of sub-atmospheric pressure under the cover and/or stimulating growth of tissue at the wound site. The apparatus further includes a source of suction configured to generate a time-varying sub-atmospheric pressure having a periodic or other variable increasing and/or decreasing waveform comprising a gradual change in pressure. The suction source cooperates with the cover to supply the time-varying sub-atmospheric pressure under the cover to the wound. The cooperation between the cover and the suction source may be provided in the form of a tube that communicates via a port in the cover to deliver the periodic time-varying sub-atmospheric pressure under the cover.

In an additional aspect of the present invention, the time-varying sub-atmospheric pressure may desirably vary between a first pressure value below the inherent tissue tension of the wound tissue and a second pressure value above the inherent tissue tension of the wound tissue. Such a variation can provide gross deformation of the wound margin, which may accelerate tissue growth. For example, the time-varying sub-atmospheric pressure may have a minimum value of 25 mm Hg below atmospheric pressure and a maximum value of 100 mm Hg below atmospheric pressure.

In addition, the present invention provides a method for administering sub-atmospheric pressure to a wound. The method includes covering a wound with a wound cover configured to maintain sub-atmospheric pressure at the site of the wound. The cover is then sealed to tissue surrounding the wound to provide an enclosure for maintaining sub-atmospheric pressure under the cover about the wound. A time-varying sub-atmospheric pressure is then applied under the cover to the wound, where the sub-atmospheric pressure has a periodic or other variable increasing and/or decreasing waveform comprising a gradual change in pressure.

BRIEF DESCRIPTION OF THE DRAWINGS

The foregoing summary and the following detailed description of the preferred embodiments of the present invention will be further understood when read in conjunction with the appended drawings, in which.

DETAILED DESCRIPTION OF THE INVENTION

Figure 1:
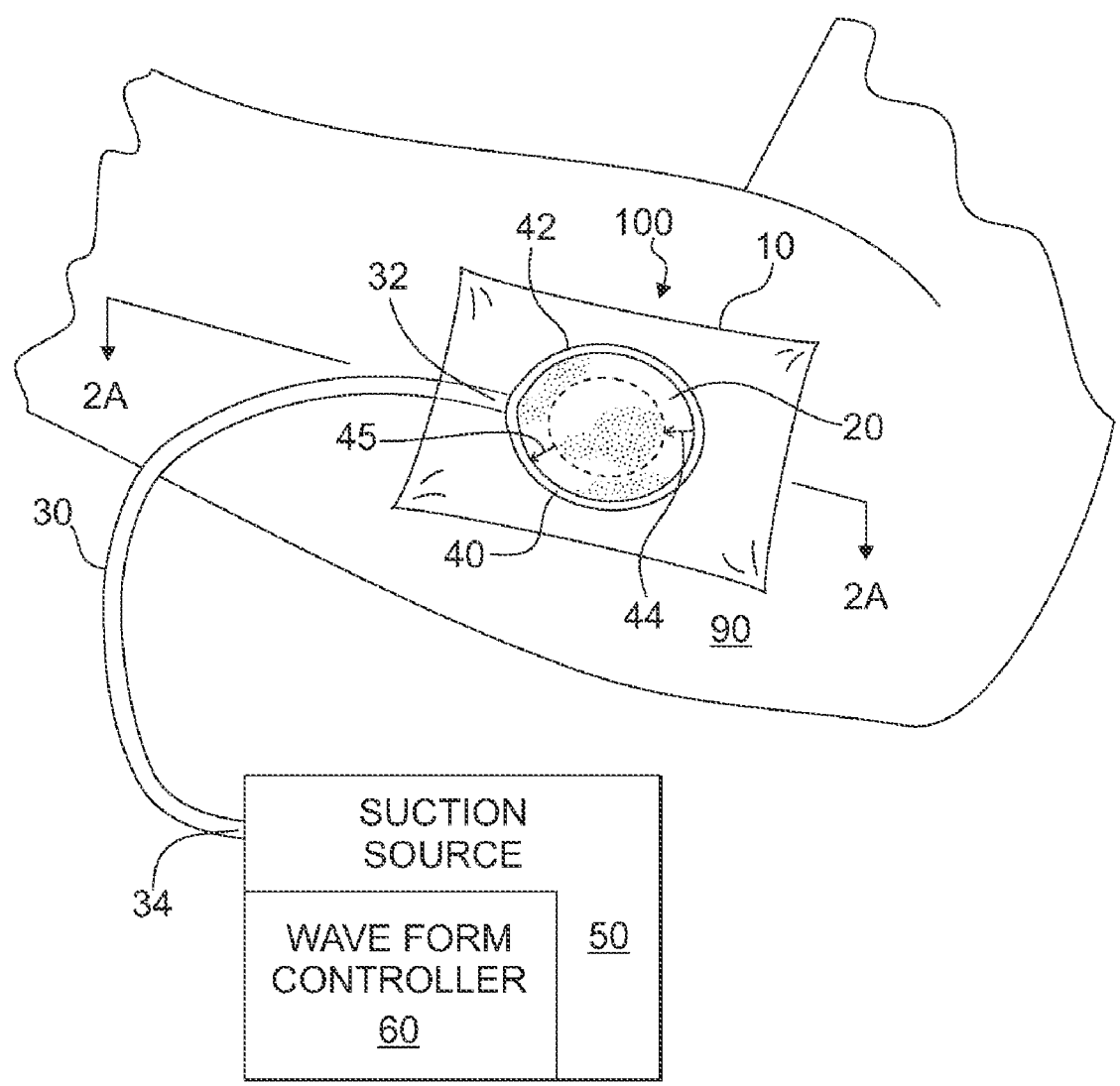
FIG. 1 schematically illustrates a top view of an apparatus in accordance with the present invention, showing the apparatus in situ on wound tissue to be treated prior to the application of sub-atmospheric pressure to the apparatus.
Figure 3A:
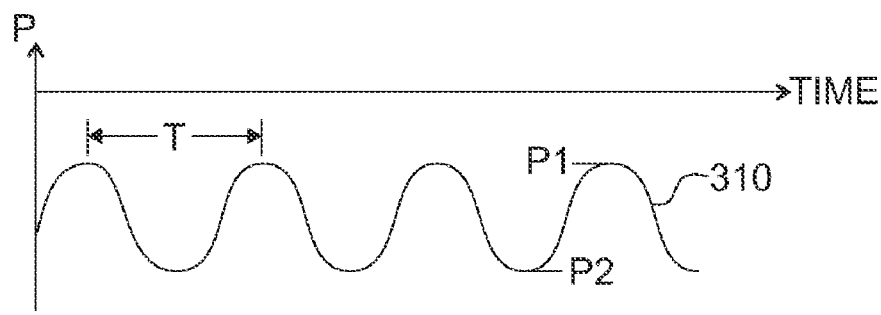
FIGS. 3A-3D schematically illustrate waveforms of cyclically varying sub-atmospheric pressures of the present invention having a gradual change in pressure, with FIG. 3A showing a sinusoidal waveform, FIG. 3B showing a triangular waveform, FIG. 3C showing a sawtooth waveform, and FIG. 3D showing a digitized sinusoidal waveform.
Figure 3B:
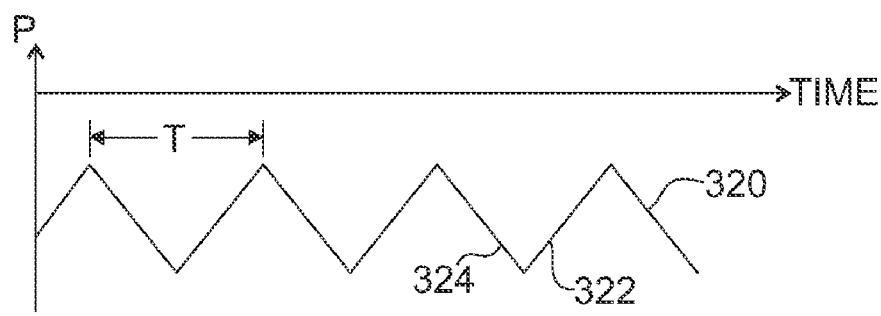
Figure 3C:
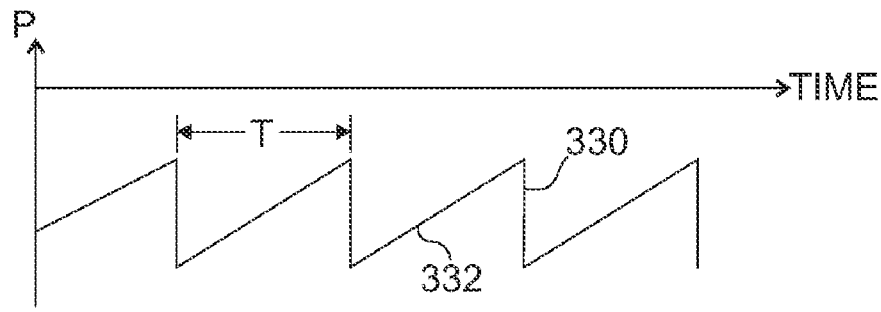
Figure 3D:
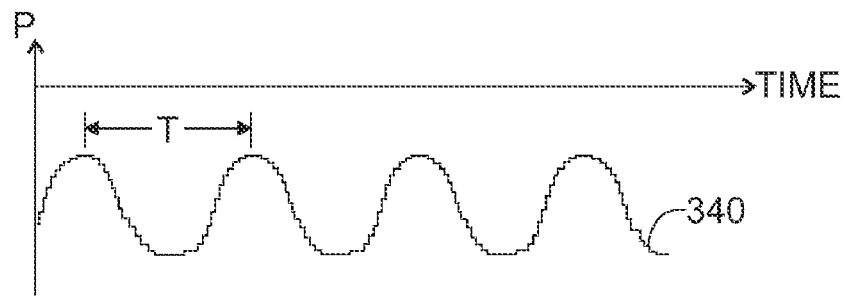
Figure 3E:
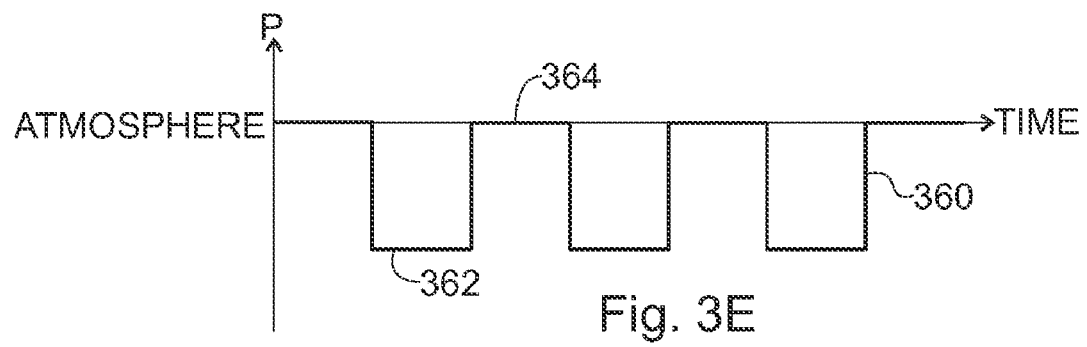
FIG. 3E schematically illustrates intermittent sub-atmospheric pressure having a square waveform.

Referring now to the figures, wherein like elements are numbered alike throughout, a sub-atmospheric treatment apparatus, generally designated 100, is provided for applying a sub-atmospheric pressure comprising a gradual change in pressure to a tissue to be treated, FIG. 1. As used herein, a "gradual" change in pressure is defined to be a change between two pressure values that is quasi-continuous or continuous, i.e., not instantaneous. In particular, sub-atmospheric pressure waveforms of the present invention comprising a gradual change in pressure desirably have a periodic, or cyclically-varying, waveform. For example, a gradual change in sub-atmospheric pressure in accordance with the present invention may be provided in the form of a sinusoidal waveform 310, FIG. 3A. Other exemplary waveforms of the present invention having a gradual or continuous change in pressure include a triangular waveform 320 and sawtooth waveform 330, each of which include a ramp-up 322, 332 and/or ramp-down 324 in pressure, FIGS. 3B and 3C. (To be continuous, a waveform need not be continuous with respect to its first and/or higher order derivatives, e.g. FIGS. 3B and 3C, though it may be, e.g. FIG. 3A.) In addition, as used herein, the definition of a gradual change in pressure also includes a quasi-continuous waveform, e.g., a digitized form of a waveform having a continuous gradual change in pressure, such as, a digitized sine wave 340, FIG. 3D. For a digitized waveform to comprise a gradual change in pressure, the digitization must comprise at least two (and preferably more) steps between the minimum and maximum value of the waveform. A gradual change in pressure does not include a pressure waveform that contains only an instantaneous change between the minimum and maximum pressures of the waveform, e.g., does not include a square or rectangular waveform 360, FIG. 3E. The term "intermittent" pressure as used herein refers to a square or rectangular waveform 360 in which the sub-atmospheric pressure is applied in alternating periods of application 362 and non-application 364, i.e., "on/off" pressure. Intermittent pressure, by definition, does not include a gradual change in pressure. Sub-atmospheric pressure having a gradual change in pressure, e.g., a sinusoidal waveform 310, provides an increased rate of healing when compared with either continuous sub-atmospheric pressure or intermittent sub-atmospheric pressure 360.

To administer a gradually changing sub-atmospheric pressure 310, 320, 330, 340 to tissue to be treated, such as a wound 40, the apparatus of the present invention includes a cover 10 for placement over the wound 40 to provide an environment about the wound 40 in which sub-atmospheric pressure may be maintained. An optional screen 20 may be provided under the cover 10 over the wound 40 to assist in the healing of the wound tissue. Sub-atmospheric pressure may be delivered under the cover 10 via a tube 30, which communicates at one end with the space under the cover 10 and at the other end with a suction source 50. The suction source 50 generates a sub-atmospheric pressure having a gradual change in pressure, which desirably has a periodic waveform. In this regard, the suction source 50 may comprise a waveform controller 60 for generating a sub-atmospheric pressure waveform.

Figure 2A:
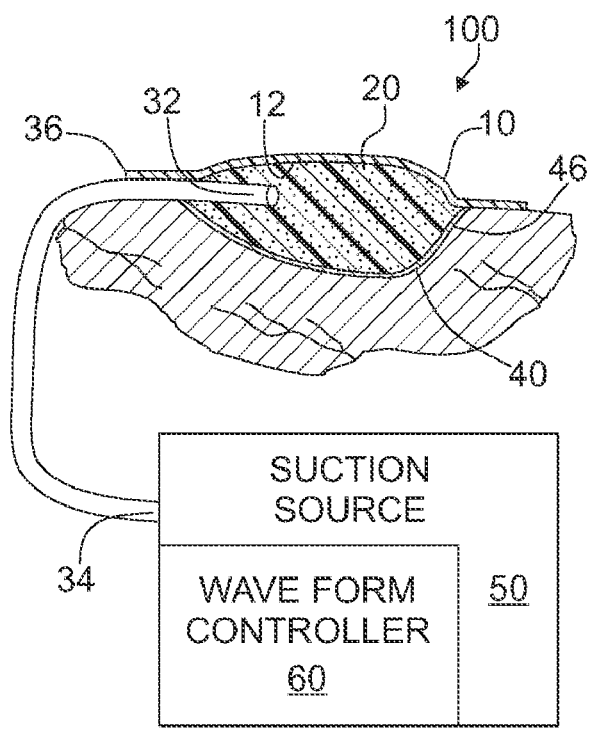
FIG. 2A schematically illustrates a side elevational view of the apparatus of FIG. 1, shown in partial section, taken along the sectioning line 2A-2A of FIG. 1.
Figure 2B:
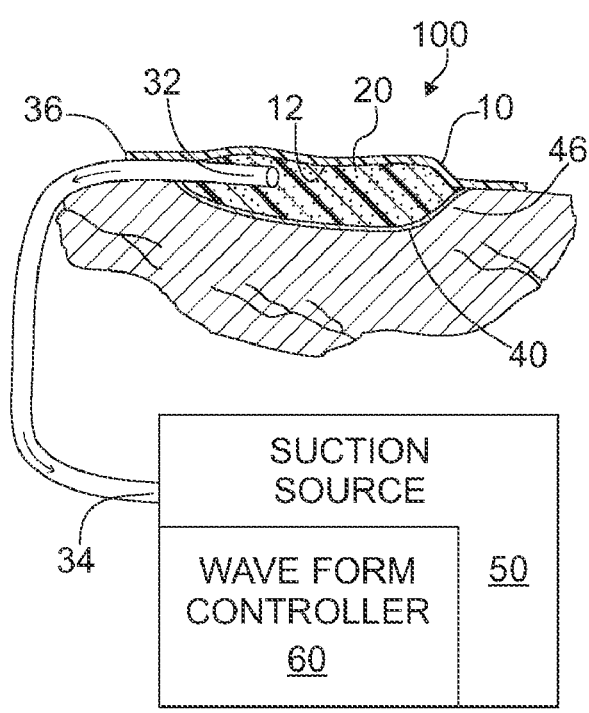
FIG. 2B schematically illustrates the apparatus of FIG. 2A with the wound surface and surrounding tissue drawn inward towards the center of the wound after the application of sub-atmospheric pressure to the wound tissue sufficient to overcome the inherent tissue tension of the wound tissue.

Turning now to the figures in more detail, FIG. 1 schematically illustrates a top view of an exemplary configuration of an apparatus 100 in accordance with the present invention applied to a treatment location 90, and FIG. 2A schematically illustrates a side elevational view in partial cross-section of the apparatus of FIG. 1 taken along the sectioning lines 2A-2A. The apparatus 100 includes a cover 10 sealed over tissue to be treated, such as a wound 40. A suitable cover 10 is one which is appropriate for medical application and capable of maintaining a sub-atmospheric pressure about the wound 40 under the cover 10. The cover 10 may be conveniently provided in the form of a self-adhesive (or non-adhesive) cover 10, such as a flexible polymer sheet or surgical drape, for example. Exemplary self-adhesive drapes include Ioban® drape (3M Corporation, St. Paul, Minn.), OpSite® drape (Smith & Nephew, Largo, Fla.), and so forth. Providing the cover 10 in the form of a flexible sheet or surgical drape may be particularly desirable for use in applications where the cover 10 should conform to the treatment site 90. Further, the use of a flexible sheet or drape may be particularly desirable in weight dependent locations. In addition, providing a self-adhesive cover 10 may simplify the application of the cover 10 to the tissue surrounding the wound 40 and may conveniently permit the cover 10 to be attached to and/or immobilize other components of the apparatus 100 which the cover adhesive contacts, such as suction tube 30 or optional screen 20. Alternatively, the cover 10 may be provided as a self-supporting rigid or semi-rigid material, which may be particularly desirable for configurations of the apparatus 100 which do not include optional screen 20 so that the cover 10 does not come in contact with the wound surface 46.

To provide an enclosure under the cover 10 in which sub-atmospheric pressure may be maintained, the cover 10 may be sealed to tissue surrounding the wound using an adhesive. For example, if a self-adhesive flexible sheet or surgical drape is used as the cover 10, the adhesive backing may be secured to the tissue surrounding the wound 40 to provide a seal about the wound 40. Instead, if a non-adhesive cover 10 is used, a separately applied adhesive or other suitable material may be used to secure the cover 10 to the treatment site 90 to provide an enclosure about the wound 40 in which sub-atmospheric pressure may be maintained. Still further, for a rigid or semi rigid cover 10, the seal may be provided by cooperation between an edge of the cover contacting the treatment site 90 and the action of sub-atmospheric pressure under the cover 10 to create sealing contact between the cover edge and the treatment site 90.

An optional screen 20 may be provided between the cover 10 and the wound surface 46 to provide various functions, such as preventing the cover 10 from contact in the wound surface 46, promoting even distribution of sub-atmospheric pressure under the cover 10, assisting in drawing of liquid away from the wound surface 46, stimulating growth of tissue (e.g., granulation tissue) at the wound surface 46, and preventing loculation of the wound 40, for example. In this regard, the screen may comprise a variety of materials such as a synthetic polymer material, open-cell polymer foam, a non-adherent material, a polymer mesh, and combinations thereof, for example. The composition and structural properties, such as reticulation, for example, are selected with regard to the function(s) to be provided by the screen 20. For instance, the degree of reticulation (or porosity) of the screen 20 may be selected to deter growth of tissue within the screen 20. Conversely, the degree of reticulation of the screen 20 may be selected to promote tissue growth therein, which may be particularly desirable if the screen 20 comprises a bio-absorbable material.

The screen 20 may be provided as a unitary structure or as a composite of separate components assembled upon application to the tissue to be treated. Exemplary materials that may be used for the screen 20, alone or in combination with other materials, include V.A.C.® GranuFoam® and V.A.C.® WhiteFoam™ dressings (Kinetic Concepts Inc, San Antonio, Tex.), Prolene® Mesh (New Brunswick, N.J.), and the like. Exemplary non-adherent materials that may be used for the screen 20, alone or in combination with other materials, include Aquaphor® Gauze (Smith & Nephew, Largo, Fla.), Adaptic® Non-Adherent Dressing (New Brunswick, N.J.), and so forth. In addition, the non-adherent material may be provided as a coating disposed on or throughout the volume of the screen 20, such as an ointment, gel, natural or synthetic polymer, or other suitable materials. For example, the non-adherent material may be provided as part of the foam screen 20, either as a one-piece screen 20, with a non-adherent material integral to the screen 20, or as a two-piece screen 20, with the screen and a non-adherent material as separate pieces. Further, for the rigid or semi rigid cover 10 it may be desirable to draw the screen 20 taut across the opening of the cover 10 above the wound 40 and to optionally attach the screen 20 to the cover 10 to provide a barrier that impedes the growth of tissue into the cavity of the cover 10.

The screen 20 is desirably cut and shaped to fit into and fill the wound 40. As the wound 40 heals and becomes smaller in size, the size of the screen 20 may be decreased accordingly. The screen 20 may be held in place by contacting an adhesive coated under surface 12 of the cover 10 to assist in securing the screen 20 in a fixed position and to assist in the removal of the screen 20 when the cover 10 is removed. One particularly convenient configuration of cover 10 and screen 20 is the combination of a flexible self-adhesive polymer sheet or drape used in conjunction with an open-cell polymer foam.

Delivery of sub-atmospheric pressure to wound 40 may be provided via a tube 30, or other suitable structure, that gaseously communicates with the enclosure under the cover 10 via a port 36. The port 36 may comprise an edge of the cover 10 under which the tube 30 passes, such as a mesentery, for example, to communicate with the space under the cover 10. Alternatively, the port 36 may be provided as an opening, or a nipple, disposed at the surface of the cover 10, or other suitable structure. The distal end of the tube 32 disposed under the cover 10 may be located above or below the optional screen 20 or may be embedded within the screen 20. In addition to having an opening at the distal end 32, the tube 30 may be fenestrated along the portion of the tube 30 in communication with the enclosure under the cover 10 to deliver sub-atmospheric pressure along the fenestrated portion of the tube 30. For example, the tube 30 may comprise a Jackson-Pratt drain.

Sub-atmospheric pressure is provided to the wound 40 by a suction source 50 via the tube 30, which is in gaseous communication with the suction source 50 at the tube's proximal end 34. The suction source 50, which may comprise a vacuum pump, includes a waveform controller 60 for controlling the time-varying properties of the pressure waveform created by the suction source 50, so that the suction source 50 produces a time-varying sub-atmospheric pressure having a gradual change in pressure (a gradually changing sub-atmospheric pressure). Sub-atmospheric pressure having a gradual change in pressure is desirably provided in the form of a periodic, or cyclically-varying, waveform that is continuous over at least a portion of the period, T, of the waveform. For example, the gradually varying sub-atmospheric pressure may take the form of a sinusoidal waveform 310, a triangular waveform 320, a sawtooth waveform 330, or a digitized waveform, such as a digitized sinusoid 340, as illustrated in FIGS. 3A-3D, respectively.

In particular applications, it may be desirable that the maximum sub-atmospheric pressure, P2, and minimum sub-atmospheric pressure, P1, be selected to induce gross tissue deformation (e.g., radial inward and outward movement 44, 45 of the wound margin 42 as illustrated in FIG. 1). The minimum sub-atmospheric pressure P1 is defined to be the pressure closest to atmospheric pressure, and the maximum sub-atmospheric pressure P2 is defined to be the pressure furthest from atmospheric pressure (i.e., stronger suction or vacuum). As the sub-atmospheric pressure varies between its maximum and minimum values P2, P1 the wound margin 42 may contract and relax, respectively. Such gross contraction and relaxation may lead to an increased rate of tissue formation as compared to application of sub-atmospheric pressure that does not provide gross deformation and relaxation. For example, gross deformation of the wound tissue may not occur if the maximum sub-atmospheric pressure P2 is large enough to cause wound margin contraction. Similarly, gross relaxation of the wound tissue may not occur if the minimum sub-atmospheric pressure P1 is not sufficiently low to permit the wound margin 42 to relax.

One such choice of minimum and maximum sub-atmospheric pressures P1, P2 for inducing gross tissue deformation are pressures that span the inherent tissue tension of the tissue or wound 40 to be treated. (Tissues have an inherent tension—if an incision is made the wound gapes open. Inherent tissue tension may be observed by the deformation of a circular defect into an elliptical shape after the tissue is removed. A mapping of these lines in humans is often referred to as 'Langer Lines'.) If the maximum sub-atmospheric pressure P2 is sufficiently large, the maximum sub-atmospheric pressure P2 can provide a radial inwardly directed force that creates radially inward movement 44 of the wound margin 42. When such radially inward movement 44 is achieved, the value of the sub-atmospheric pressure is above the inherent tissue of the wound tissue. After the wound margin 42 has contracted inwardly due to the application of sub-atmospheric pressure, the wound margin 42 can relax and approach its original rest position if the minimum sub-atmospheric pressure P1 is sufficiently small (close to atmospheric pressure). In such a case, the time-varying sub-atmospheric pressure is said to vary between a first (minimum) pressure value P1 below the inherent tissue tension of the wound tissue and a second (maximum) pressure value P2 above the inherent tissue tension of the wound tissue. Thus, the cyclic variation in the sub-atmospheric pressure can create an accompanying cyclic radial inward and outward movement 44, 45 of the wound margin 42.

In addition to an apparatus as described above, the present invention provides a method for administering sub-atmospheric pressure to a wound 40. The method includes covering a wound 40 with a wound cover 10 configured to maintain sub-atmospheric pressure at the site of the wound 40, and sealing the cover 10 to tissue surrounding the wound 40 to provide an enclosure for maintaining sub-atmospheric pressure under the cover 10 about the wound 40. The method continues with the application of time-varying sub-atmospheric pressure under the cover 10 to the wound 40, where the sub-atmospheric pressure has a periodic waveform comprising a gradual change in pressure. The gradual change in pressure may extend over a portion of the period of the periodic waveform, or may extend over the full period of the periodic waveform. In addition, the time-varying sub-atmospheric pressure may vary between a first pressure value below the inherent tissue tension of the wound tissue and a second pressure value above the inherent tissue tension of the wound tissue.

Example 1

A pilot study was performed on two pigs to compare the effects of sine wave application of sub-atmospheric pressure to continuous sub-atmospheric pressure, intermittent sub-atmospheric pressure, and wet-to-moist gauze dressings. The pigs were procured and allowed to acclimate to the new housing conditions for one week. The animals were transported to the operating room and the backs of the animals shaved and prepped for surgery. On the first animal four full thickness wounds, 5 cm in diameter and extending to the fascia covering the spine and deep back muscles, were created over the spine (midline). On the second animal, two pairs of wounds were created lateral to the spine, two on each side of the spine. One treatment was applied to each wound: 1) sine wave sub-atmospheric pressure varying from 50 mm Hg below atmospheric pressure to 150 mm Hg below atmospheric pressure; 2) continuous sub-atmospheric pressure at 125 mm Hg below atmospheric pressure; 3) intermittent sub-atmospheric pressure on for 5 minutes at 125 mm Hg below atmospheric pressure and off for 2 minutes (i.e., no sub-atmospheric pressure applied); and 4) wet-to-moist gauze dressings. The volume of the wounds was measured by taking alginate impressions, then submersing the cast impression into a water filled graduated cylinder. The volume of fluid displacement equaled the volume of the defect.

The first animal was euthanized after seven days as all wounds became infected. The second animal was treated for 10 days. It was noted for the first animal, prior to becoming infected, that the sine wave sub-atmospheric pressure treated wound appeared 'grayish' in color, perhaps due to the sub-atmospheric pressure level being too high (i.e., too far below atmospheric pressure). The sine wave sub-atmospheric pressure treated wounds produced new granulation tissue faster than the continuously treated wounds, but less rapidly than the intermittent sub-atmospheric pressure treated wounds. All three sub-atmospheric pressure applications caused formation of granulation tissue faster than wet-to-moist gauze dressing changes. It was also noted during the study that the wound edges of the intermittent sub-atmospheric pressure treated wounds grossly moved with each cycle of sub-atmospheric pressure application and cessation. The edges of the sine wave and continuous sub-atmospheric pressure treated wounds grossly moved only on initial application of the sub-atmospheric pressure. It was determined that the amplitude of the sine wave, even at the low end (i.e., end closest to atmospheric pressure, was too great (greater than the inherent tissue tension). It was concluded from this pilot study that a further study needed to be undertaken in which the level of sub-atmospheric pressure of the sine wave application should oscillate above and below the inherent tissue tension of full thickness pig skin.

In preparation for the second study, a test was conducted to determine the correlation between vacuum level and force. A 10 ml syringe was fixed vertically with the tip up and the plunger down. A tube was connected to the tip of the syringe, with the other end of the tube connected to a vacuum pump. The plunger was withdrawn. A predetermined sub-atmospheric pressure level was applied, which resulted in the

TABLE 1

| Animal | Pressure Type | Initial Wound Volume (cc) | Final Wound Volume (cc) | Days from initial to final | Fill Rate (cc/day) |
|---|---|---|---|---|---|
| 1 | None (gauze) | 12 | 8 | 7 | 0.57 |
|   | Continuous | 14 | 9 | 7 | 0.71 |
|   | Intermittent | 18 | 7 | 7 | 1.57 |
|   | Sine-wave | 27 | 19 | 7 | 1.14 |
| 2 | None (gauze) | 9 | 4 | 10 | 0.5 |
|   | Continuous | 8.5 | 2 | 10 | 0.65 |
|   | Intermittent | 11 | 2 | 10 | 0.9 |
|   | Sine-wave | 9 | 2 | 10 | 0.7 | plunger being drawn into the barrel of the syringe. Weights were applied to the plunger until the plunger stopped moving. (Increased weight would have drawn the plunger back out of the barrel of the syringe.) A linear response was determined for sub-atmospheric pressure versus applied force (F=ma). The static friction of the system was measured by having the plunger fully inserted into the barrel of the syringe, then applying weights until the plunger started to move down. The static friction was subtracted from the measurements to determine the relationship between sub-atmospheric pressure and force. The resulting relationship between force in Newtons, F, and sub-atmospheric pressure in mm Hg, P, was found to be F=0.0214 P−0.1372. According to an article by Ksander, et al. (Plastic and Reconstructive Surgery, 59(3): 398-406, 1977), wounds created on the back (dorsal surface) of young swine require approximately 50 grams of force to grossly displace the edges of the wound (Ksander, FIG. 1). Thus, we concluded that 30 mm Hg below atmospheric pressure would create a force equal to 50 grams, which should be the level above and below which sub-atmospheric pressure should oscillate to cause gross tissue (and hence cellular) deformation.

Example 2

Six 25 kg white feeder swine were used as the animal models in this study. Each pig was acclimated to the environment for a full week before the study began. At the outset, each animal was sedated via intramuscular injection of a 10 ml ketamine, 2 ml acepromazine and 1 ml xylazine cocktail. Once sedated, the pig was transferred to the animal surgery suite, shaved, prepped for surgery and anesthetized with halothane and oxygen. Under sterile conditions two 5 cm diameter, circular, full-thickness wounds were created, 5 cm apart, on the animal's dorsal midline, extending down to the deep postural back muscles. A GranuFoam® sponge (Kinetic Concepts Inc, San Antonio, Tex.) was then cut into two circles of 5 cm diameter to fit the two wounds. Evacuation tubes were connected to each sponge and the whole area was draped with an Ioban® drape (3M Corporation, St. Paul, Minn.). A heavy plastic harness was then placed over the dressing, and two stockinette t-shirts were positioned over the harness, to stabilize dressings and tubing. The pig was then returned to its housing and one evacuation tube was connected to a V.A.C.® pump delivering 5 minute on/2 minute off intermittent square wave application of 100 mm Hg below atmospheric pressure and the other evacuation tube was connected to a vacuum pump delivering a sine wave application varying between 25 and 100 mm Hg below atmospheric pressure with a 60 second periodicity. The subjects were staggered such that if the square wave was applied to the front wound and sine wave applied to the back wound, then the next subject would have opposite application, to control for the influence of the wound's anatomic position on wound healing.

Daily dressing changes and volume measurements were made by making impressions of the wounds using Jeltrate® Alginate (DENTSPLY International, York, Pa.) impression material. The volume was measured by water displacement in a 100 ml graduated cylinder.

Data from six 25 kg white feeder swine demonstrate a 19% increase in the rate of granulation tissue formation in the sine wave sub-atmospheric pressure (mean rate 1.354 cc/day) when compared with square wave intermittent sub-atmospheric pressure (mean rate 1.141 cc/day) (p=0.12). If this data were extrapolated and compared with prior studies, then sine wave sub-atmospheric pressure demonstrates roughly 122% acceleration in granulation tissue formation when compared with standard moist gauze application to the wound bed. In addition to providing for an increased rate of healing as compared to intermittent sub-atmospheric pressure, sine wave sub-atmospheric pressure appears to reduce problems associated with air leaks. Sine wave sub-atmospheric pressure is thought to prevent air leaks, because the sub-atmospheric pressure is applied and removed more gradually. Further, unlike intermittent sub-atmospheric pressure, leaks may be deterred by providing a gradually varying pressure that does not return to atmospheric pressure during the pressure variation cycle.

TABLE 2

| Animal | Pressure Type | Initial Wound Volume (cc) | Final Wound Volume (cc) | Days from initial to final | Fill Rate (cc/day) |
|---|---|---|---|---|---|
| 1 | Intermittent | 10 | 0 | 10 | 1 |
|   | Sine-wave | 10 | 0 | 10 | 1 |
| 2 | Intermittent | 12 | 6 | 8 | 0.75 |
|   | Sine-wave | 12 | 1 | 8 | 1.375 |
| 3 | Intermittent | 10 | 0 | 8 | 1.25 |
|   | Sine-wave | 11 | 0 | 8 | 1.375 |
| 4 | Intermittent | 17 | 4 | 9 | 1.444 |
|   | Sine-wave | 13 | 2 | 9 | 1.222 |
| 5 | Intermittent | 13 | 0 | 10 | 1.3 |
|   | Sine-wave | 16 | 0 | 9 | 1.778 |
| 6 | Intermittent | 10 | 1.5 | 8 | 1.1 |
|   | Sine-wave | 11 | 0 | 8 | 1.375 |
| Mean | Intermittent |   |   |   | 1.141 |
|   | Sine-wave |   |   |   | 1.354 |

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. An apparatus for administering sub-atmospheric pressure to a wound, comprising:
   (a) a cover adapted to cover a wound and adapted to maintain sub-atmospheric pressure at the site of the wound;
   (b) a seal configured to seal the cover to tissue surrounding the wound; and
   (c) a source of suction configured to generate a time-varying sub-atmospheric pressure having a periodic waveform comprising a gradual change in pressure, the suction source cooperating with the cover to supply the time-varying sub-atmospheric pressure under the cover to the wound,
   wherein the source of suction is configured to generate a triangular-waveform variation in pressure between a first pressure value below atmospheric pressure and a second pressure value below atmospheric pressure.

2. An apparatus for administering sub-atmospheric pressure to a wound, comprising:
   (a) a cover adapted to cover a wound and adapted to maintain sub-atmospheric pressure at the site of the wound;
   (b) a seal configured to seal the cover to tissue surrounding the wound; and
   (c) a source of suction configured to generate a time-varying sub-atmospheric pressure having a periodic waveform comprising a gradual change in pressure, the suction source cooperating with the cover to supply the time-varying sub-atmospheric pressure under the cover to the wound,
   wherein the source of suction is configured to generate a sinusoidal-waveform variation in pressure between a first pressure value below atmospheric pressure and a second pressure value below atmospheric pressure.

3. The apparatus of claim 2, wherein the first pressure value is 25 mm Hg below atmospheric pressure and the second pressure value is 100 mm Hg below atmospheric pressure.

4. The apparatus of claim 2, wherein the first pressure value is below the inherent tissue tension of the wound tissue and the second pressure value is above the inherent tissue tension of the wound tissue.

5. The apparatus of claim 1, wherein the first pressure value is 25 mm Hg below atmospheric pressure and the second pressure value is 100 mm Hg below atmospheric pressure.

6. The apparatus of claim 1, wherein the first pressure value is below the inherent tissue tension of the wound tissue and the second pressure value is above the inherent tissue tension of the wound tissue.

7. An apparatus for administering sub-atmospheric pressure to a wound, comprising:
   (a) a cover adapted to cover a wound and adapted to maintain sub-atmospheric pressure at the site of the wound;
   (b) a seal configured to seal the cover to tissue surrounding the wound; and
   (c) a source of suction configured to generate a time-varying sub-atmospheric pressure having a periodic waveform comprising a gradual change in pressure, the suction source cooperating with the cover to supply the time-varying sub-atmospheric pressure under the cover to the wound,
   wherein the source of suction is configured to generate a sawtooth-waveform variation in pressure between a first pressure value below atmospheric pressure and a second pressure value below atmospheric pressure.

8. The apparatus of claim 7, wherein the first pressure value is 25 mm Hg below atmospheric pressure and the second pressure value is 100 mm Hg below atmospheric pressure.

9. The apparatus of claim 7, wherein the first pressure value is below the inherent tissue tension of the wound tissue and the second pressure value is above the inherent tissue tension of the wound tissue.

10. The apparatus of claim 1, wherein the source of suction comprises a vacuum pump.

11. The apparatus of claim 1, wherein the cover comprises a flexible sheet.

12. The apparatus of claim 11, wherein the seal includes an adhesive on a sheet surface facing the wound to attach and seal the sheet to tissue surrounding the wound.

13. The apparatus of claim 11, comprising a screen for placement at the wound between the cover and the wound.

14. The apparatus of claim 1, comprising a screen for placement at the wound between the cover and the wound.

15. The apparatus of claim 14, wherein the screen comprises open-cell foam.

16. The apparatus of claim 14, wherein the screen comprises a synthetic polymer material.

17. The apparatus of claim 14, wherein the screen comprises a non-adherent material.

18. The apparatus of claim 14, wherein the screen comprises a polymer mesh.

19. The apparatus of claim 18, wherein the screen comprises a synthetic polymer material.

20. The apparatus of claim 19, wherein the screen comprises an ointment.

21. The apparatus of claim 14, wherein the screen is configured to promote the formation of tissue of the type with which the screen is in contact.

22. The apparatus of claim 14, wherein the screen is configured to promote the formation of granulation tissue.

23. The apparatus of claim 14, wherein the screen is configured to promote tissue growth therein.

24. The apparatus of claim 14, wherein the screen is configured to deter tissue growth therein.

25. The apparatus of claim 14, wherein the screen comprises a bio-absorbable material.

26. The apparatus of claim 1, comprising a port at the cover configured to deliver the sub-atmospheric pressure under the cover.

27. The apparatus of claim 26, wherein port comprises a tube in gaseous communication with the source of suction.

28. The apparatus of claim 27, wherein the tube extends under an edge of the cover.

29. An apparatus for administering sub-atmospheric pressure to a wound, comprising:
(a) a self-adhesive cover adapted to cover and form a seal about a wound to maintain sub-atmospheric pressure at the site of the wound;
(b) port at the cover configured to deliver the sub-atmospheric pressure under the cover; and
(c) a source of suction for gaseous communication with the port, the source of suction configured to generate a sinusoidally varying sub-atmospheric pressure under the cover to the wound,
wherein the source of suction is configured to generate a sinusoidal-waveform variation in pressure between a first pressure value below atmospheric pressure and a second pressure value below atmospheric pressure under the cover of the wound.

30. The apparatus of claim 29, wherein sinusoidally varying sub-atmospheric pressure has a minimum value of 25 mm Hg below atmospheric pressure and a maximum value of 100 mm Hg below atmospheric pressure.

31. The apparatus of claim 29, wherein the sub-atmospheric pressure varies between a first pressure value below the inherent tissue tension of the wound tissue and a second pressure value above the inherent tissue tension of the wound tissue.

32. The apparatus of claim 29, wherein the source of suction comprises a vacuum pump.

33. The apparatus of claim 29, wherein the cover comprises a flexible sheet.

34. The apparatus of claim 33, comprising a screen for placement at the wound between the cover and the wound.

35. The apparatus of claim 29, comprising a screen for placement at the wound between the cover and the wound.

36. The apparatus of claim 35, wherein the screen comprises open-cell foam.

37. The apparatus of claim 35, wherein the screen comprises a synthetic polymer material.

38. The apparatus of claim 35, wherein the screen comprises a non-adherent material.

39. The apparatus of claim 35, wherein the screen comprises a polymer mesh.

40. The apparatus of claim 39, wherein the screen comprises a synthetic polymer material.

41. The apparatus of claim 40, wherein the screen comprises an ointment.

42. The apparatus of claim 35, wherein the screen is configured to promote the formation of tissue of the type with which the screen is in contact.

43. The apparatus of claim 35, wherein the screen is configured to promote the formation of granulation tissue.

44. The apparatus of claim 35, wherein the screen is configured to promote tissue growth therein.

45. The apparatus of claim 35, wherein the screen is configured to deter tissue growth therein.

46. The apparatus of claim 35, wherein the screen comprises a bio-absorbable material.

47. The apparatus of claim 29, wherein the port comprises a tube in gaseous communication with the source of suction.

48. The apparatus of claim 47, wherein the tube extends under an edge of the cover.

49. An apparatus for administering sub-atmospheric pressure to a wound, comprising:
(a) a cover adapted to cover a wound to provide an enclosure above the wound in which sub-atmospheric pressure may be maintained;
(b) a screen configured to overlie the wound under the cover; and
(c) a vacuum means in gaseous communication with the cover to supply sub-atmospheric pressure within the enclosure, the vacuum means configured to generate a cyclically-varying sub-atmospheric pressure comprising a gradual change in pressure,
wherein the vacuum means is configured to generate a sinusoidal-waveform variation in pressure between a first pressure value below atmospheric pressure and a second pressure value below atmospheric pressure.

50. The apparatus of claim 1, wherein the first pressure value is 25 mm Hg below atmospheric pressure and the second pressure value is 100 mm Hg below atmospheric pressure.

51. The apparatus of claim 1, wherein the first pressure value is below the inherent tissue tension of the wound tissue and the second pressure value is above the inherent tissue tension of the wound tissue.

52. An apparatus for administering sub-atmospheric pressure to a wound, comprising:
(a) a cover adapted to cover a wound to provide an enclosure above the wound in which sub-atmospheric pressure may be maintained;
(b) a screen configured to overlie the wound under the cover; and
(c) a vacuum means in gaseous communication with the cover to supply sub-atmospheric pressure within the enclosure, the vacuum means configured to generate a cyclically-varying sub-atmospheric pressure comprising a gradual change in pressure,
wherein the vacuum means is configured to generate a triangular-waveform variation in pressure between a first pressure value below atmospheric pressure and a second pressure value below atmospheric pressure.

53. The apparatus of claim 52, wherein the first pressure value is 25 mm Hg below atmospheric pressure and the second pressure value is 100 mm Hg below atmospheric pressure.

54. The apparatus of claim 52, wherein the first pressure value is below the inherent tissue tension of the wound tissue and the second pressure value is above the inherent tissue tension of the wound tissue.

55. An apparatus for administering sub-atmospheric pressure to a wound, comprising:
(a) a cover adapted to cover a wound to provide an enclosure above the wound in which sub-atmospheric pressure may be maintained;
(b) a screen configured to overlie the wound under the cover; and
(c) a vacuum means in gaseous communication with the cover to supply sub-atmospheric pressure within the enclosure, the vacuum means configured to generate a cyclically-varying sub-atmospheric pressure comprising a gradual change in pressure,
wherein the vacuum means is configured to generate a sawtooth-waveform variation in pressure between a first pressure value below atmospheric pressure and a second pressure value below atmospheric pressure.

56. The apparatus of claim 55, wherein the first pressure value is 25 mm Hg below atmospheric pressure and the second pressure value is 100 mm Hg below atmospheric pressure.

57. The apparatus of claim 55, wherein the first pressure value is below the inherent tissue tension of the wound tissue and the second pressure value is above the inherent tissue tension of the wound tissue.

58. The apparatus of claim 49, wherein the vacuum means comprises a vacuum pump.

59. The apparatus of claim 49, wherein the cover comprises a flexible self-adhesive sheet for sealing to tissue about the wound.

60. The apparatus of claim 49, wherein the screen comprises open-cell foam.

61. The apparatus of claim 49, wherein the screen comprises a synthetic polymer material.

62. The apparatus of claim 49, wherein the screen comprises a non-adherent material.

63. The apparatus of claim 49, wherein the screen comprises a polymer mesh.

64. The apparatus of claim 63, wherein the screen comprises a synthetic polymer material.

65. The apparatus of claim 64, wherein the screen comprises an ointment.

66. The apparatus of claim 49, wherein the screen is configured to promote the formation of tissue of the type with which the screen is in contact.

67. The apparatus of claim 49, wherein the screen is configured to promote the formation of granulation tissue.

68. The apparatus of claim 49, wherein the screen is configured to promote tissue growth therein.

69. The apparatus of claim 49, wherein the screen is configured to deter tissue growth therein.

70. The apparatus of claim 49, wherein the screen comprises a bio-absorbable material.

71. The apparatus of claim 49, comprising a port at the cover configured to deliver the sub-atmospheric pressure under the cover.

72. The apparatus of claim 71, wherein the port comprises a tube in gaseous communication with the vacuum means.

73. The apparatus of claim 72, wherein the tube extends under an edge of the cover.

74. An apparatus for administering sub-atmospheric pressure to a wound, comprising:
a) a cover adapted to cover a wound to provide an enclosure above the wound in which sub-atmospheric pressure may be maintained;
(b) a port disposed at the cover configured to deliver the sub-atmospheric pressure under the cover; and
(c) a vacuum means in gaseous communication with the port to supply sub-atmospheric pressure within the enclosure, the vacuum means configured to generate a cyclically-varying sub-atmospheric pressure comprising a gradual change in pressure over at least a portion of the cycle, the change ranging from first pressure value below the inherent tissue tension of the wound tissue to a second pressure value above the inherent tissue tension of the wound tissue,
wherein the vacuum means is configured to generate a sawtooth-waveform variation in pressure between a first pressure value below atmospheric pressure and a second pressure value below atmospheric pressure.

75. An apparatus for administering sub-atmospheric pressure to a wound, comprising:
a) a cover adapted to cover a wound to provide an enclosure above the wound in which sub-atmospheric pressure may be maintained;
(b) a port disposed at the cover configured to deliver the sub-atmospheric pressure under the cover; and
(c) a vacuum means in gaseous communication with the port to supply sub-atmospheric pressure within the enclosure, the vacuum means configured to generate a cyclically-varying sub-atmospheric pressure comprising a gradual change in pressure over at least a portion of the cycle, the change ranging from first pressure value below the inherent tissue tension of the wound tissue to a second pressure value above the inherent tissue tension of the wound tissue,
wherein the vacuum means is configured to generate a sinusoidal-waveform variation in pressure between a first pressure value below atmospheric pressure and a second pressure value below atmospheric pressure.

76. The apparatus of claim 75, wherein the first pressure value is 25 mm Hg below atmospheric pressure and the second pressure value is 100 mm Hg below atmospheric pressure.

77. An apparatus for administering sub-atmospheric pressure to a wound, comprising:
(a) a cover adapted to cover a wound to provide an enclosure above the wound in which sub-atmospheric pressure may be maintained;
(b) a port disposed at the cover configured to deliver the sub-atmospheric pressure under the cover; and
(c) a vacuum means in gaseous communication with the port to supply sub-atmospheric pressure within the enclosure, the vacuum means configured to generate a cyclically-varying sub-atmospheric pressure comprising a gradual change in pressure over at least a portion of the cycle, the change ranging from first pressure value below the inherent tissue tension of the wound tissue to a second pressure value above the inherent tissue tension of the wound tissue,
wherein the vacuum means is configured to generate a triangular-waveform variation in pressure between a first pressure value below atmospheric pressure and a second pressure value below atmospheric pressure.

78. The apparatus of claim 77, wherein the first pressure value is 25 mm Hg below atmospheric pressure and the second pressure value is 100 mm Hg below atmospheric pressure.

79. The apparatus of claim 74, wherein the first pressure value is 25 mm Hg below atmospheric pressure and the second pressure value is 100 mm Hg below atmospheric pressure.

80. The apparatus of claim 74, wherein the vacuum means comprises a vacuum pump.

81. The apparatus of claim 74, wherein the cover comprises a flexible self-adhesive sheet for sealing to tissue about the wound.

82. The apparatus of claim 81, comprising a screen for placement at the wound between the cover and the wound.

83. The apparatus of claim 74, comprising a screen for placement at the wound between the cover and the wound.

84. The apparatus of claim 83, wherein the screen comprises open-cell foam.

85. The apparatus of claim 83, wherein the screen comprises a synthetic polymer material.

86. The apparatus of claim 83, wherein the screen comprises a non-adherent material.

87. The apparatus of claim 83, wherein the screen comprises a polymer mesh.

88. The apparatus of claim 87, wherein the screen comprises a synthetic polymer material.

89. The apparatus of claim 88, wherein the screen comprises an ointment.

90. The apparatus of claim 83, wherein the screen is configured to promote the formation of tissue of the type with which the screen is in contact.

91. The apparatus of claim 83, wherein the screen is configured to promote the formation of granulation tissue.

92. The apparatus of claim 83, wherein the screen is configured to promote tissue growth therein.

93. The apparatus of claim 83, wherein the screen is configured to deter tissue growth therein.

94. The apparatus of claim 83, wherein the screen comprises a bio-absorbable material.

95. The apparatus of claim 74, wherein the port comprises a tube in gaseous communication with the vacuum means.

96. The apparatus of claim 95, wherein the tube extends under an edge of the cover.

97. A method for administering sub-atmospheric pressure to a wound, comprising the steps of:
   (a) covering a wound with a wound cover configured to maintain sub-atmospheric pressure under the cover at the site of the wound;
   (b) sealing the cover to tissue surrounding the wound to provide an enclosure for maintaining sub-atmospheric pressure under the cover about the wound; and
   (c) applying time-varying sub-atmospheric pressure under the cover to the wound, the sub-atmospheric pressure having a periodic waveform comprising a gradual change in pressure,
   wherein the time-varying sub-atmospheric pressure comprises a sinusoidal-waveform variation in pressure that varies between a first pressure value below atmospheric pressure and a second pressure value below atmospheric pressure.

98. The method of claim 97, wherein the first pressure value is 25 mm Hg below atmospheric pressure and the second pressure value is 100 mm Hg below atmospheric pressure.

99. The method of claim 97, wherein the first pressure value is below the inherent tissue tension of the wound tissue and the second pressure value is above the inherent tissue tension of the wound tissue.

100. A method for administering sub-atmospheric pressure to a wound, comprising the steps of:
   (a) covering a wound with a wound cover configured to maintain sub-atmospheric pressure under the cover at the site of the wound;
   (b) sealing the cover to tissue surrounding the wound to provide an enclosure for maintaining sub-atmospheric pressure under the cover about the wound; and
   (c) applying time-varying sub-atmospheric pressure under the cover to the wound, the sub-atmospheric pressure having a periodic waveform comprising a gradual change in pressure,
   wherein the time-varying sub-atmospheric pressure comprises a triangular-waveform variation in pressure between a first pressure value below atmospheric pressure and a second pressure value below atmospheric pressure.

101. The method of claim 100, wherein the first pressure value is 25 mm Hg below atmospheric pressure and the second pressure value is 100 mm Hg below atmospheric pressure.

102. The method of claim 100, wherein the first pressure value is below the inherent tissue tension of the wound tissue and the second pressure value is above the inherent tissue tension of the wound tissue.

103. A method for administering sub-atmospheric pressure to a wound, comprising the steps of:
   (a) covering a wound with a wound cover configured to maintain sub-atmospheric pressure under the cover at the site of the wound;
   (b) sealing the cover to tissue surrounding the wound to provide an enclosure for maintaining sub-atmospheric pressure under the cover about the wound; and
   (c) applying time-varying sub-atmospheric pressure under the cover to the wound, the sub-atmospheric pressure having a periodic waveform comprising a gradual change in pressure,
   wherein the time-varying sub-atmospheric pressure comprises a sawtooth-waveform variation in pressure between a first pressure value below atmospheric pressure and a second pressure value below atmospheric pressure.

104. The method of claim 103, wherein the first pressure value is 25 mm Hg below atmospheric pressure and the second pressure value is 100 mm Hg below atmospheric pressure.

105. The method of claim 103, wherein the first pressure value is below the inherent tissue tension of the wound tissue and the second pressure value is above the inherent tissue tension of the wound tissue.

106. The method of claim 97, comprising placing a screen between the cover and the wound.

107. The method of claim 106, wherein the screen comprises open-cell foam.

108. The apparatus of claim 106, wherein the screen comprises a synthetic polymer material.

109. The method of claim 106, wherein the screen comprises a non-adherent material.

110. The apparatus of claim 106, wherein the screen comprises a polymer mesh.

111. The method of claim 110, wherein the screen comprises a synthetic polymer material.

112. The method of claim 111, wherein the screen comprises an ointment.

113. The method of claim 106, wherein the screen is configured to promote the formation of tissue of the type with which the screen is in contact.

114. The method of claim 106, wherein the screen is configured to promote the formation of granulation tissue.

115. The method of claim 106, wherein the screen is configured to promote tissue growth therein.

116. The apparatus of claim 106, wherein the screen is configured to deter tissue growth therein.

117. The method of claim 106, wherein the screen comprises a bio-absorbable material.

118. The apparatus according to any one of claims 1, 2, 7, 49, 52, 55, 74, 75, 77, 97, 100, or 103, wherein the gradual change in pressure comprises a digitized waveform.

* * * * *

UNITED STATES PATENT AND TRADEMARK OFFICE
CERTIFICATE OF CORRECTION

| | |
|---|---|
| PATENT NO. | : 8,377,016 B2 |
| APPLICATION NO. | : 11/621728 |
| DATED | : February 19, 2013 |
| INVENTOR(S) | : Louis C. Argenta et al. |

Page 1 of 1

It is certified that error appears in the above-identified patent and that said Letters Patent is hereby corrected as shown below:

On the Title Page of the patent, at item (75) Inventors, the name "Louis O. Argenta" should read --Louis C. Argenta--.

Signed and Sealed this
Ninth Day of April, 2013

Teresa Stanek Rea
*Acting Director of the United States Patent and Trademark Office*